United States Patent
Brown

(10) Patent No.: US 12,312,599 B2
(45) Date of Patent: *May 27, 2025

(54) METHODS, COMPOSITIONS, AND KITS FOR PRODUCING BEIGE ADIPOCYTES AND TREATING METABOLIC DISORDERS

(71) Applicant: MaineHealth, Scarborough, ME (US)

(72) Inventor: Aaron C. Brown, Portland, ME (US)

(73) Assignee: MaineHealth, Scarborough, ME (US)

( * ) Notice: Subject to any disclaimer, the term of this patent is extended or adjusted under 35 U.S.C. 154(b) by 465 days.

This patent is subject to a terminal disclaimer.

(21) Appl. No.: 17/667,934

(22) Filed: Feb. 9, 2022

(65) Prior Publication Data

US 2022/0162557 A1  May 26, 2022

Related U.S. Application Data

(63) Continuation of application No. 16/245,298, filed on Jan. 11, 2019, now Pat. No. 11,279,915.

(60) Provisional application No. 62/616,507, filed on Jan. 12, 2018.

(51) Int. Cl.
| | | |
|---|---|---|
| *A61K 35/35* | (2015.01) | |
| *A61K 38/20* | (2006.01) | |
| *A61K 45/06* | (2006.01) | |
| *A61P 3/04* | (2006.01) | |
| *A61P 3/06* | (2006.01) | |
| *A61P 3/10* | (2006.01) | |
| *C12N 5/077* | (2010.01) | |

(52) U.S. Cl.
CPC ............ *C12N 5/0653* (2013.01); *A61K 35/35* (2013.01); *A61K 38/2026* (2013.01); *A61K 45/06* (2013.01); *A61P 3/04* (2018.01); *A61P 3/06* (2018.01); *A61P 3/10* (2018.01); *C12N 2501/2304* (2013.01); *C12N 2501/999* (2013.01)

(58) Field of Classification Search
None
See application file for complete search history.

(56) References Cited

U.S. PATENT DOCUMENTS

| | | |
|---|---|---|
| 11,279,915 B2 | 3/2022 | Brown |
| 2016/0186140 A1 | 6/2016 | Dalton et al. |
| 2017/0009263 A1 | 1/2017 | Conradie et al. |
| 2018/0216070 A1* | 8/2018 | Deschaseaux ......... G01N 33/50 |
| 2019/0140151 A1 | 5/2019 | Kadan et al. |

FOREIGN PATENT DOCUMENTS

WO    WO-2017/009263 A1    1/2017

OTHER PUBLICATIONS

Berry et al., The developmental origins of adipose tissue. Development. Oct. 2013;140(19):3939-49.
Bonafoux et al., Strategies for TGF-beta modulation: a review of recent patents. Expert Opin Ther Pat. Dec. 2009;19(12):1759-69.
Breyer et al., The next generation of therapeutics for chronic kidney disease. Nat Rev Drug Discov. Aug. 2016;15(8):568-88.
Candelore et al., Potent and selective human beta(3)-adrenergic receptor antagonists. J Pharmacol Exp Ther. Aug. 1999;290(2):649-55.
Cannon et al., Brown adipose tissue: function and physiological significance. Physiol Rev. Jan. 2004;84(1):277-359.
Cao et al., p38 mitogen-activated protein kinase is the central regulator of cyclic AMP-dependent transcription of the brown fat uncoupling protein 1 gene. Mol Cell Biol. Apr. 2004;24(7):3057-67.
Chau et al., Visceral and subcutaneous fat have different origins and evidence supports a mesothelial source. Nat Cell Biol. Apr. 2014;16(4):367-75.
Chung et al., A self-sustained loop of inflammation-driven inhibition of beige adipogenesis in obesity. Nat Immunol. Jun. 2017;18(6):654-664.
Consoli et al., Behavioral effects of the beta3 adrenoceptor agonist SR58611A: is it the putative prototype of a new class of antidepressant/anxiolytic drugs? Eur J Pharmacol. Nov. 14, 2007;573(1-3):139-47.
Cordeiro, Technology evaluation: lerdelimumab, Cambridge Antibody Technology. Curr Opin Mol Ther. Apr. 2003;5(2):199-203.
Crisan et al., A perivascular origin for mesenchymal stem cells in multiple human organs. Cell Stem Cell. Sep. 11, 2008;3(3):301-13.
Cristancho et al., Forming functional fat: a growing understanding of adipocyte differentiation. Nat Rev Mol Cell Biol. Sep. 28, 2011;12(11):722-34.
Cypress et al., Activation of human brown adipose tissue by a beta3-adrenergic receptor agonist. Cell Metab. Jan. 6, 2015;21(1):33-8.
Cypress et al., Identification and importance of brown adipose tissue in adult humans. N Engl J Med. Apr. 9, 2009;360(15):1509-17.
Dressler, Advances in early kidney specification, development and patterning. Development. Dec. 2009;136(23):3863-74.
Edmondson et al., Discovery of Vibegron: A Potent and Selective ß3 Adrenergic Receptor Agonist for the Treatment of Overactive Bladder. J Med Chem. Jan. 28, 2016;59(2):609-23.
Esteve et al., Human white and brite adipogenesis is supported by MSCA1 and is impaired by immune cells. Stem Cells. Apr. 2015;33(4):1277-91.
Fischer et al., Alternatively activated macrophages do not synthesize catecholamines or contribute to adipose tissue adaptive thermogenesis. Nat Med. May 2017;23(5):623-630.
Fu et al., The effects of beta(3)-adrenoceptor agonist CL-316,243 on adiponectin, adiponectin receptors and tumor necrosis factor-alpha expressions in adipose tissues of obese diabetic KKAy mice. Eur J Pharmacol. Apr. 14, 2008;584(1):202-6.

(Continued)

*Primary Examiner* — Daniel C Gamett
(74) *Attorney, Agent, or Firm* — McCarter & English, LLP; David G. Conlin

(57) ABSTRACT

Provided herein are, inter alia, methods, compositions, and kits for producing adipocyte populations such as beige adipocyte populations. Also included are methods and compositions for increasing the level of adipocyte populations (e.g., beige adipocyte populations) in a subject, as well as methods and compositions for treating subjects who are overweight, obese, or who have diabetes.

17 Claims, 55 Drawing Sheets

Specification includes a Sequence Listing.

(56) References Cited

OTHER PUBLICATIONS

Giaccone et al., A phase III study of belagenpumatucel-L, an allogeneic tumour cell vaccine, as maintenance therapy for non-small cell lung cancer. Eur J Cancer. Nov. 2015;51(16):2321-9.

Graja et al., Mechanisms of aging-related impairment of brown adipocyte development and function. Gerontology. 2015;61(3):211-7.

Gras, Mirabegron for the treatment of overactive bladder. Drugs Today (Barc). Jan. 2012;48(1):25-32.

Guenantin et al., Functional Human Beige Adipocytes From Induced Pluripotent Stem Cells. Diabetes. Jun. 2017;66(6):1470-1478.

Hafner et al., Brown-like adipose progenitors derived from human induced pluripotent stem cells: Identification of critical pathways governing their adipogenic capacity. Sci Rep. Aug. 31, 2016;6:32490, 9 pages.

Hafner et al., Human induced pluripotent stem cells: A new source for brown and white adipocytes. World J Stem Cells. Sep. 26, 2014;6(4):467-72.

Harms et al., Brown and beige fat: development, function and therapeutic potential. Nat Med. Oct. 2013;19(10):1252-63.

Hassan et al., Adipose tissue: friend or foe? Nat Rev Cardiol. Dec. 2012;9(12):689-702. pre-publication edition.

Hicks et al., GW427353 (solabegron), a novel, selective beta3-adrenergic receptor agonist, evokes bladder relaxation and increases micturition reflex threshold in the dog. J Pharmacol Exp Ther. Oct. 2007;323(1):202-9.

Jaschinski et al., The antisense oligonucleotide trabedersen (AP 12009) for the targeted inhibition of TGF-beta2. Curr Pharm Biotechnol. Dec. 2011;12(12):2203-13.

Larsen et al., Effect of a 28-d treatment with L-796568, a novel beta(3)-adrenergic receptor agonist, on energy expenditure and body composition in obese men. Am J Clin Nutr. Oct. 2002;76(4):780-8.

Lee et al., Activated type 2 innate lymphoid cells regulate beige fat biogenesis. Cell. Jan. 15, 2015;160(1-2):74-87.

Lee et al., In vivo identification of bipotential adipocyte progenitors recruited by ß3-adrenoceptor activation and high-fat feeding. Cell Metab. Apr. 4, 2012;15(4):480-91.

Li et al., Mechanical stretch inhibits mesenchymal stem cell adipogenic differentiation through TGFbeta1/Smad2 signaling. J Biomech. Oct. 15, 2015;48(13):3665-71.

Lidell et al., Two types of brown adipose tissue in humans. Adipocyte. Jan. 1, 2014;3(1):63-6.

Liu et al., Brown adipose tissue transplantation improves whole-body energy metabolism. Cell Res. Jun. 2013;23(6):851-4.

Lizcano et al., Human ADMC-Derived Adipocyte Thermogenic Capacity Is Regulated by IL-4 Receptor. Stem Cells Int. 2017;2017:2767916, 10 pages.

Lumeng et al., Inflammatory links between obesity and metabolic disease. J Clin Invest. Jun. 2011;121(6):2111-7.

Luzzani et al., Pluripotent Stem Cells as a Robust Source of Mesenchymal Stem Cells. Stem Cell Rev Rep. Feb. 2017;13(1):68-78.

Mahlapuu et al., Haploinsufficiency of the forkhead gene Foxf1, a target for sonic hedgehog signaling, causes lung and foregut malformations. Development. Jun. 2001;128(12):2397-406.

Mahlapuu et al., The forkhead transcription factor Foxf1 is required for differentiation of extra-embryonic and lateral plate mesoderm. Development. Jan. 2001;128(2):155-66.

Malik et al., Global obesity: trends, risk factors and policy implications. Nat Rev Endocrinol. Jan. 2013;9(1):13-27.

Mohsen-Kanson et al., Differentiation of human induced pluripotent stem cells into brown and white adipocytes: role of Pax3. Stem Cells. Jun. 2014;32(6):1459-67.

Morris et al., Phase I study of GC1008 (fresolimumab): a human anti-transforming growth factor-beta (TGFß) monoclonal antibody in patients with advanced malignant melanoma or renal cell carcinoma. PLoS One. Mar. 11, 2014;9(3):e90353, 11 pages.

Necchi et al., PF-03446962, a fully-human monoclonal antibody against transforming growth-factor beta (TGFß) receptor ALK1, in pre-treated patients with urothelial cancer: an open label, single-group, phase 2 trial. Invest New Drugs. Jun. 2014;32(3):555-60.

Nishio et al., Production of functional classical brown adipocytes from human pluripotent stem cells using specific hemopoietin cocktail without gene transfer. Cell Metab. Sep. 5, 2012;16(3):394-406.

Ochner et al., Treating obesity seriously: when recommendations for lifestyle change confront biological adaptations. Lancet Diabetes Endocrinol. Apr. 2015;3(4):232-4.

Overstreet et al., Confirmation of antidepressant potential of the selective beta3 adrenoceptor agonist amibegron in an animal model of depression. Pharmacol Biochem Behav. Jun. 2008;89(4):623-6.

Patel et al., Role of subcutaneous adipose tissue in the pathogenesis of insulin resistance. J Obes. 2013;2013:489187, 5 pages.

Poleganov et al., Efficient Reprogramming of Human Fibroblasts and Blood-Derived Endothelial Progenitor Cells Using Nonmodified RNA for Reprogramming and Immune Evasion. Hum Gene Ther. Nov. 2015;26(11):751-66.

Qiu et al., Eosinophils and type 2 cytokine signaling in macrophages orchestrate development of functional beige fat. Cell. Jun. 5, 2014;157(6):1292-1308.

Ravussin et al., Effect of intermittent cold exposure on brown fat activation, obesity, and energy homeostasis in mice. PLoS One. Jan. 17, 2014;9(1):e85876, 9 pages.

Reitman, How Does Fat Transition from White to Beige? Cell Metab. Jul. 5, 2017;26(1):14-16.

Roberts et al., Development expression of Hox11 and specification of splenic cell fate. Am J Pathol. May 1995;146(5):1089-101.

Seale et al., Brown fat in humans: turning up the heat on obesity. Diabetes. Jul. 2009;58(7):1482-4.

Su et al., A Renewable Source of Human Beige Adipocytes for Development of Therapies to Treat Metabolic Syndrome. Cell Rep. Dec. 11, 2018;25(11):3215-3228.

Tan et al., Efficient derivation of lateral plate and paraxial mesoderm subtypes from human embryonic stem cells through GSKi-mediated differentiation. Stem Cells Dev. Jul. 1, 2013;22(13):1893-906.

Tang et al., White fat progenitor cells reside in the adipose vasculature. Science. Oct. 24, 2008;322(5901):583-6.

Timmons et al., Myogenic gene expression signature establishes that brown and white adipocytes originate from distinct cell lineages. Proc Natl Acad Sci U S A. Mar. 13, 2007;104(11):4401-6.

Tolcher et al., A phase 1 study of anti-TGFbeta receptor type-II monoclonal antibody LY3022859 in patients with advanced solid tumors. Cancer Chemother Pharmacol. Apr. 2017;79(4):673-680.

Tribioli et al., Bapx1: an evolutionary conserved homologue of the Drosophila bagpipe homeobox gene is expressed in splanchnic mesoderm and the embryonic skeleton. Mech Dev. Jul. 1997;65(1-2):145-62.

Van Den Berg et al., Immune Modulation of Brown(ing) Adipose Tissue in Obesity. Endocr Rev. Feb. 1, 2017;38(1):46-68.

Vishvanath et al., Pdgfrbeta+ Mural Preadipocytes Contribute to Adipocyte Hyperplasia Induced by High-Fat-Diet Feeding and Prolonged Cold Exposure in Adult Mice. Cell Metab. Feb. 9, 2016;23(2):350-9.

Wang et al., Brown adipose tissue activation is inversely related to central obesity and metabolic parameters in adult human. PLoS One. Apr. 20, 2015;10(4):e0123795, 13 pages.

Wang et al., Control of brown and beige fat development. Nat Rev Mol Cell Biol. Nov. 2016;17(11):691-702.

Wang et al., Ebf2 is a selective marker of brown and beige adipogenic precursor cells. Proc Natl Acad Sci U S A. Oct. 7, 2014;111(40):14466-71.

Wang et al., The brown fat secretome: metabolic functions beyond thermogenesis. Trends Endocrinol Metab. May 2015;26(5):231-7.

Wasteson et al., Developmental origin of smooth muscle cells in the descending aorta in mice. Development. May 2008;135(10):1823-32.

Xiao et al., Anti-obesity and metabolic efficacy of the beta3-adrenergic agonist, CL316243, in mice at thermoneutrality compared to 22° C. Obesity (Silver Spring). Jul. 2015;23(7):1450-9.

Yadav et al., Protection from obesity and diabetes by blockade of TGF-beta/Smad3 signaling. Cell Metab. Jul. 6, 2011;14(1):67-79.

(56) References Cited

OTHER PUBLICATIONS

Yadav et al., TGF-beta/Smad3 Signaling Regulates Brown Adipocyte Induction in White Adipose Tissue. Front Endocrinol (Lausanne). Mar. 14, 2012;3:35, 6 pages.

* cited by examiner

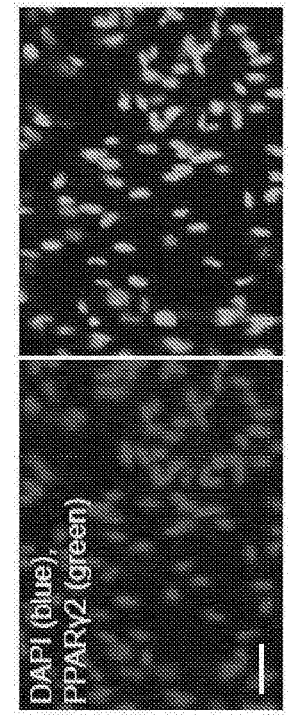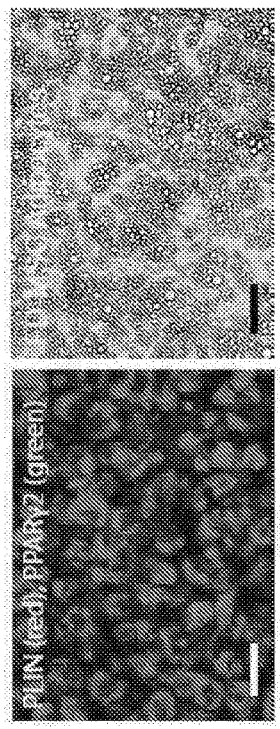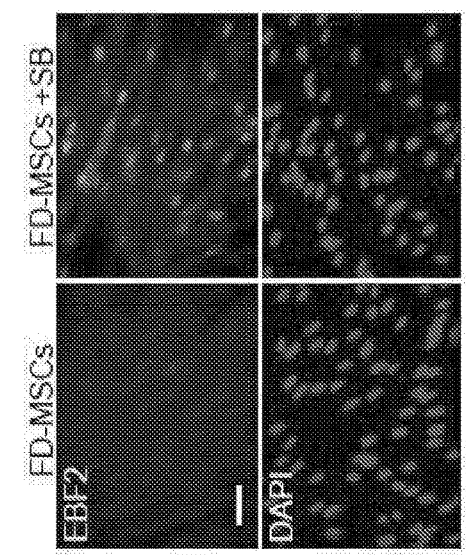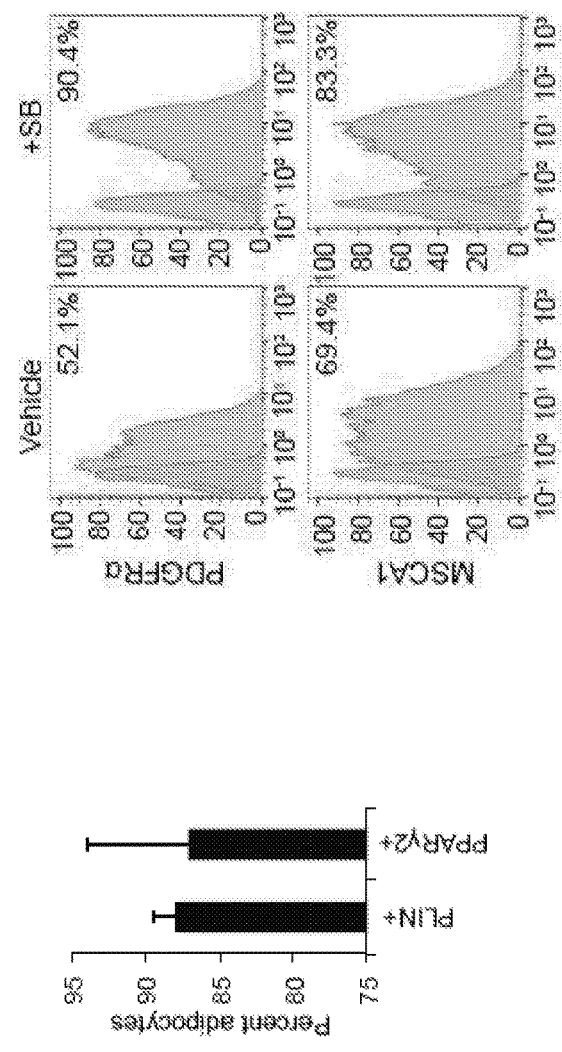
FIG. 3K
FIG. 3L
FIG. 3M
FIG. 3N
FIG. 3O

| | FD-MSCs | iPSC-beige | subQ |
|---|---|---|---|
| FGF21 (pg/ml) | N.D. | 174.0 ± 15.7 | 151.9 ± 24.8 |
| NRG4 (ng/ml) | N.D. | 1.3 ± 0.2 | N.D |
| IL6 (pg/ml) | N.D. | 15.6 ± 2.1 | 41.2 ± 7.7 |
| ADIPOQ (ug/ml) | N.D. | 13.8 ± 0.5 | 3.4 ± 0.7 |

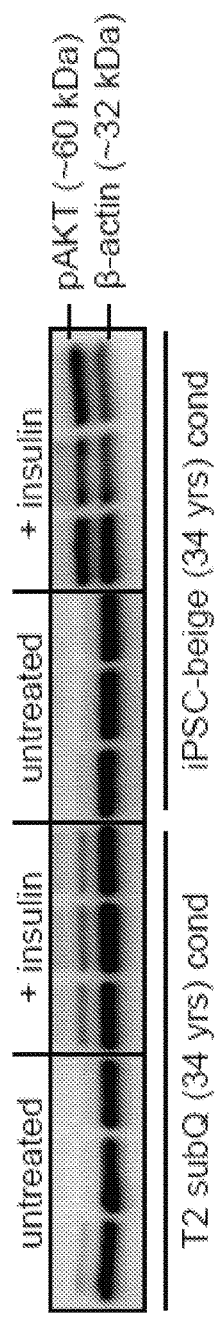
FIG. 16A
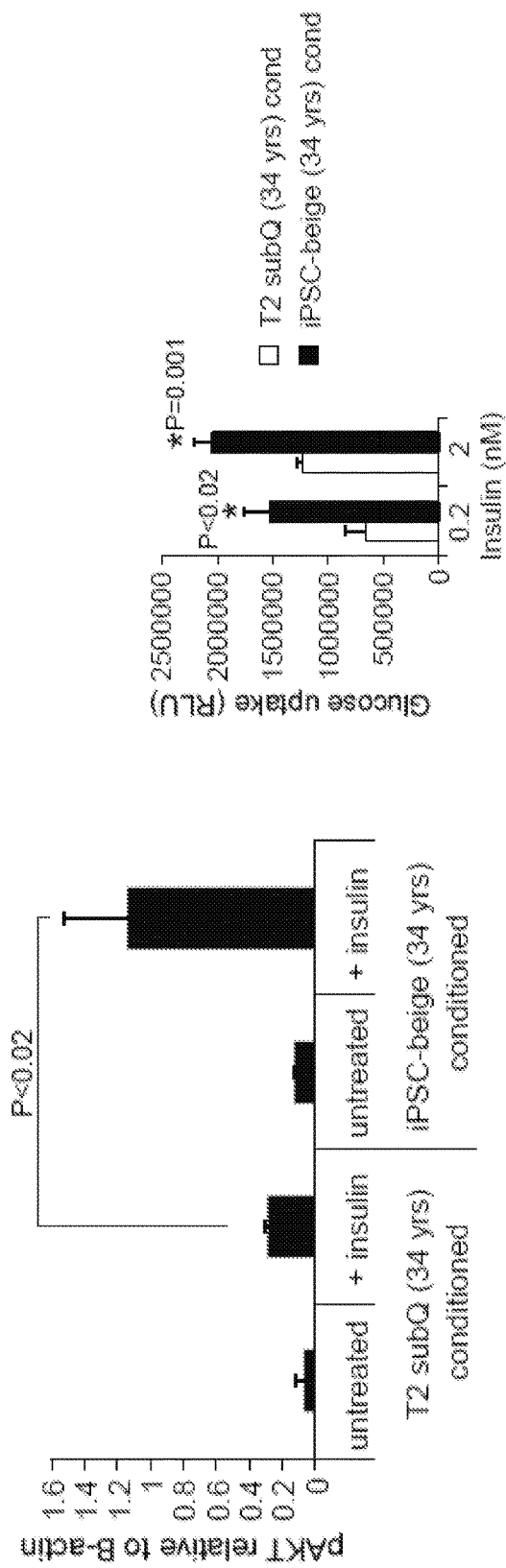
FIG. 16C
FIG. 16B

SEQUENCE LISTING

<160> NUMBER OF SEQ ID NOS: 74

<210> SEQ ID NO 1
<211> LENGTH: 22
<212> TYPE: DNA
<213> ORGANISM: Artificial Sequence
<220> FEATURE:
<223> OTHER INFORMATION: UCP1 Forward

<400> SEQUENCE: 1
agttcctcac cgcagggaaa ga     22

<210> SEQ ID NO 2
<211> LENGTH: 22
<212> TYPE: DNA
<213> ORGANISM: Artificial Sequence
<220> FEATURE:
<223> OTHER INFORMATION: UCP1 Reverse

<400> SEQUENCE: 2
gtagcgaggt ttgattccgt gg     22

<210> SEQ ID NO 3
<211> LENGTH: 22
<212> TYPE: DNA
<213> ORGANISM: Artificial Sequence
<220> FEATURE:
<223> OTHER INFORMATION: CEBPA Reverse

<400> SEQUENCE: 3
agtgcgcgat ctggaactgc ag     22

<210> SEQ ID NO 4
<211> LENGTH: 22
<212> TYPE: DNA
<213> ORGANISM: Artificial Sequence
<220> FEATURE:
<223> OTHER INFORMATION: CEBPA Reverse

<400> SEQUENCE: 4
agtgcgcgat ctggaactgc ag     22

<210> SEQ ID NO 5

```
<211> LENGTH: 22
<212> TYPE: DNA
<213> ORGANISM: Artificial Sequence
<220> FEATURE:
<223> OTHER INFORMATION: CEBPB Forward

<400> SEQUENCE: 5
agaagaccgt ggacaagcac ag                                          22

<210> SEQ ID NO 6
<211> LENGTH: 21
<212> TYPE: DNA
<213> ORGANISM: Artificial Sequence
<220> FEATURE:
<223> OTHER INFORMATION: CEBPB Reverse

<400> SEQUENCE: 6
ctccaggacc ttgtgctgcg t                                           21

<210> SEQ ID NO 7
<211> LENGTH: 22
<212> TYPE: DNA
<213> ORGANISM: Artificial Sequence
<220> FEATURE:
<223> OTHER INFORMATION: EBF2 Forward

<400> SEQUENCE: 7
gagcaagaag gcttgaccca tc                                          22

<210> SEQ ID NO 8
<211> LENGTH: 23
<212> TYPE: DNA
<213> ORGANISM: Artificial Sequence
<220> FEATURE:
<223> OTHER INFORMATION: EBF2 Reverse

<400> SEQUENCE: 8
ccaaacacaa cctggagacc atc                                         23

<210> SEQ ID NO 9
<211> LENGTH: 22
<212> TYPE: DNA
<213> ORGANISM: Artificial Sequence
<220> FEATURE:
<223> OTHER INFORMATION: PGC1A Forward

<400> SEQUENCE: 9
ccaaaggatg cgctctcgtt ca                                          22

<210> SEQ ID NO 10
<211> LENGTH: 22
<212> TYPE: DNA
<213> ORGANISM: Artificial Sequence
<220> FEATURE:
<223> OTHER INFORMATION: PGC1a Reverse

<400> SEQUENCE: 10
cggtgtctgt agtggcttga ct                                          22

<210> SEQ ID NO 11
<211> LENGTH: 22
<212> TYPE: DNA
<213> ORGANISM: Artificial Sequence
<220> FEATURE:
<223> OTHER INFORMATION: PRDM16 Forward

<400> SEQUENCE: 11
```

-continued cagccaatct caccagacac ct                                              22

<210> SEQ ID NO 12
<211> LENGTH: 22
<212> TYPE: DNA
<213> ORGANISM: Artificial Sequence
<220> FEATURE:
<223> OTHER INFORMATION: PRDM16 Reverse

<400> SEQUENCE: 12
gtggcacttg aaaggcttct cc                                              22

<210> SEQ ID NO 13
<211> LENGTH: 18
<212> TYPE: DNA
<213> ORGANISM: Artificial Sequence
<220> FEATURE:
<223> OTHER INFORMATION: PPARgamma Forward

<400> SEQUENCE: 13
cgaggacacc ggagaggg                                                   18

<210> SEQ ID NO 14
<211> LENGTH: 22
<212> TYPE: DNA
<213> ORGANISM: Artificial Sequence
<220> FEATURE:
<223> OTHER INFORMATION: PPARgammar Reverse

<400> SEQUENCE: 14
tgtggtttag tgttggcttc tt                                              22

<210> SEQ ID NO 15
<211> LENGTH: 22
<212> TYPE: DNA
<213> ORGANISM: Artificial Sequence
<220> FEATURE:
<223> OTHER INFORMATION: TMEM26 Forward

<400> SEQUENCE: 15
gcagtttcca cttgacctgg ca                                              22

<210> SEQ ID NO 16
<211> LENGTH: 23
<212> TYPE: DNA
<213> ORGANISM: Artificial Sequence
<220> FEATURE:
<223> OTHER INFORMATION: TMEM26 Reverse

<400> SEQUENCE: 16
gaagacgctg attccgatgt tcc                                             23

<210> SEQ ID NO 17
<211> LENGTH: 20
<212> TYPE: DNA
<213> ORGANISM: Artificial Sequence
<220> FEATURE:
<223> OTHER INFORMATION: CITED1 Forward

<400> SEQUENCE: 17
ccactagctc ctctggatcg                                                 20

<210> SEQ ID NO 18
<211> LENGTH: 20
<212> TYPE: DNA

```
<213> ORGANISM: Artificial Sequence
<220> FEATURE:
<223> OTHER INFORMATION: CITED1 Reverse

<400> SEQUENCE: 18
agccccttgg tactggctat                                              20

<210> SEQ ID NO 19
<211> LENGTH: 22
<212> TYPE: DNA
<213> ORGANISM: Artificial Sequence
<220> FEATURE:
<223> OTHER INFORMATION: CD137 Forward

<400> SEQUENCE: 19
tcttcctcac gctccgtttc tc                                           22

<210> SEQ ID NO 20
<211> LENGTH: 22
<212> TYPE: DNA
<213> ORGANISM: Artificial Sequence
<220> FEATURE:
<223> OTHER INFORMATION: CD137 Reverse

<400> SEQUENCE: 20
tggaaatcgg cagctacagc ca                                           22

<210> SEQ ID NO 21
<211> LENGTH: 22
<212> TYPE: DNA
<213> ORGANISM: Artificial Sequence
<220> FEATURE:
<223> OTHER INFORMATION: ZIC1 Forward

<400> SEQUENCE: 21
gatgtgcgac aagtcctaca cg                                           22

<210> SEQ ID NO 22
<211> LENGTH: 22
<212> TYPE: DNA
<213> ORGANISM: Artificial Sequence
<220> FEATURE:
<223> OTHER INFORMATION: ZIC1 Reverse

<400> SEQUENCE: 22
tggaggattc gtagccagag ct                                           22

<210> SEQ ID NO 23
<211> LENGTH: 22
<212> TYPE: DNA
<213> ORGANISM: Artificial Sequence
<220> FEATURE:
<223> OTHER INFORMATION: PDGFRa Forward

<400> SEQUENCE: 23
gactttcgcc aaagtggagg ag                                           22

<210> SEQ ID NO 24
<211> LENGTH: 22
<212> TYPE: DNA
<213> ORGANISM: Artificial Sequence
<220> FEATURE:
<223> OTHER INFORMATION: PDGFRa Reverse

<400> SEQUENCE: 24
agccaccgtg agttcagaac gc                                           22
```

<210> SEQ ID NO 25
<211> LENGTH: 18
<212> TYPE: DNA
<213> ORGANISM: Artificial Sequence
<220> FEATURE:
<223> OTHER INFORMATION: PPARgamma1 Forward

<400> SEQUENCE: 25
cgaggacacc ggagaggg                                                    18

<210> SEQ ID NO 26
<211> LENGTH: 22
<212> TYPE: DNA
<213> ORGANISM: Artificial Sequence
<220> FEATURE:
<223> OTHER INFORMATION: PPARgamma 1 Reverse

<400> SEQUENCE: 26
tgtggtttag tgttggcttc tt                                               22

<210> SEQ ID NO 27
<211> LENGTH: 22
<212> TYPE: DNA
<213> ORGANISM: Artificial Sequence
<220> FEATURE:
<223> OTHER INFORMATION: PPARgamma 2 Forward

<400> SEQUENCE: 27
ttttaacgga ttgatctttt gc                                               22

<210> SEQ ID NO 28
<211> LENGTH: 20
<212> TYPE: DNA
<213> ORGANISM: Artificial Sequence
<220> FEATURE:
<223> OTHER INFORMATION: PPARgamma 2 Reverse

<400> SEQUENCE: 28
aggagtggga gtggtcttcc                                                  20

<210> SEQ ID NO 29
<211> LENGTH: 20
<212> TYPE: DNA
<213> ORGANISM: Artificial Sequence
<220> FEATURE:
<223> OTHER INFORMATION: PPARgamma 3 Forward

<400> SEQUENCE: 29
ttctgcttaa ttccctttcc                                                  20

<210> SEQ ID NO 30
<211> LENGTH: 20
<212> TYPE: DNA
<213> ORGANISM: Artificial Sequence
<220> FEATURE:
<223> OTHER INFORMATION: PPARgamma 3 Reverse

<400> SEQUENCE: 30
aggagtggga gtggtcttcc                                                  20

<210> SEQ ID NO 31
<211> LENGTH: 22
<212> TYPE: DNA
<213> ORGANISM: Artificial Sequence
<220> FEATURE:

<223> OTHER INFORMATION: BAPX1 Forward

<400> SEQUENCE: 31
ccgcttccaa agacctagag ga          22

<210> SEQ ID NO 32
<211> LENGTH: 21
<212> TYPE: DNA
<213> ORGANISM: Artificial Sequence
<220> FEATURE:
<223> OTHER INFORMATION: BAPX1 Reverse

<400> SEQUENCE: 32
accgtcgtcc tcggtccttg g           21

<210> SEQ ID NO 33
<211> LENGTH: 22
<212> TYPE: DNA
<213> ORGANISM: Artificial Sequence
<220> FEATURE:
<223> OTHER INFORMATION: HOX11 Forward

<400> SEQUENCE: 33
tgtgccaggc tcttctggaa gg          22

<210> SEQ ID NO 34
<211> LENGTH: 21
<212> TYPE: DNA
<213> ORGANISM: Artificial Sequence
<220> FEATURE:
<223> OTHER INFORMATION: HOX11 Reverse

<400> SEQUENCE: 34
ctccgcacct gctgggactt c           21

<210> SEQ ID NO 35
<211> LENGTH: 22
<212> TYPE: DNA
<213> ORGANISM: Artificial Sequence
<220> FEATURE:
<223> OTHER INFORMATION: FOXF1 Forward

<400> SEQUENCE: 35
agcagccgta tctgcaccag aa          22

<210> SEQ ID NO 36
<211> LENGTH: 22
<212> TYPE: DNA
<213> ORGANISM: Artificial Sequence
<220> FEATURE:
<223> OTHER INFORMATION: FOXF1 Reverse

<400> SEQUENCE: 36
ctcctttcgg tcacacatgc tg          22

<210> SEQ ID NO 37
<211> LENGTH: 21
<212> TYPE: DNA
<213> ORGANISM: Artificial Sequence
<220> FEATURE:
<223> OTHER INFORMATION: IRX3 Forward

<400> SEQUENCE: 37
ctccgcacct gctgggactt c           21

```
<210> SEQ ID NO 38
<211> LENGTH: 22
<212> TYPE: DNA
<213> ORGANISM: Artificial Sequence
<220> FEATURE:
<223> OTHER INFORMATION: IRX3 Reverse

<400> SEQUENCE: 38
ctccacttcc aaggcactac ag                                               22

<210> SEQ ID NO 39
<211> LENGTH: 23
<212> TYPE: DNA
<213> ORGANISM: Artificial Sequence
<220> FEATURE:
<223> OTHER INFORMATION: T (brachyury) forward

<400> SEQUENCE: 39
ccttcagcaa agtcaagctc acc                                              23

<210> SEQ ID NO 40
<211> LENGTH: 22
<212> TYPE: DNA
<213> ORGANISM: Artificial Sequence
<220> FEATURE:
<223> OTHER INFORMATION: T (brachyury) Reverse

<400> SEQUENCE: 40
tgaactgggt ctcagggaag ca                                               22

<210> SEQ ID NO 41
<211> LENGTH: 21
<212> TYPE: DNA
<213> ORGANISM: Artificial Sequence
<220> FEATURE:
<223> OTHER INFORMATION: MIXL1 Forward

<400> SEQUENCE: 41
cccgacatcc acttgcgcga g                                                21

<210> SEQ ID NO 42
<211> LENGTH: 22
<212> TYPE: DNA
<213> ORGANISM: Artificial Sequence
<220> FEATURE:
<223> OTHER INFORMATION: MIXL1 Reverse

<400> SEQUENCE: 42
ggaaggattt cccactctga cg                                               22

<210> SEQ ID NO 43
<211> LENGTH: 22
<212> TYPE: DNA
<213> ORGANISM: Artificial Sequence
<220> FEATURE:
<223> OTHER INFORMATION: SOX1 Forward

<400> SEQUENCE: 43
gagtggaagg tcatgtccga gg                                               22

<210> SEQ ID NO 44
<211> LENGTH: 22
<212> TYPE: DNA
<213> ORGANISM: Artificial Sequence
<220> FEATURE:
<223> OTHER INFORMATION: SOX1 Reverse
```

```
<400> SEQUENCE: 44
ccttcttgag cagcgtcttg gt                                          22

<210> SEQ ID NO 45
<211> LENGTH: 23
<212> TYPE: DNA
<213> ORGANISM: Artificial Sequence
<220> FEATURE:
<223> OTHER INFORMATION: SOX17 Forward

<400> SEQUENCE: 45
acgctttcat ggtgtgggct aag                                         23

<210> SEQ ID NO 46
<211> LENGTH: 21
<212> TYPE: DNA
<213> ORGANISM: Artificial Sequence
<220> FEATURE:
<223> OTHER INFORMATION: SOX17 Reverse

<400> SEQUENCE: 46
gtcagcgcct tccacgactt g                                           21

<210> SEQ ID NO 47
<211> LENGTH: 22
<212> TYPE: DNA
<213> ORGANISM: Artificial Sequence
<220> FEATURE:
<223> OTHER INFORMATION: VEGFR2 Forward

<400> SEQUENCE: 47
ggaacctcac tatccgcaga gt                                          22

<210> SEQ ID NO 48
<211> LENGTH: 22
<212> TYPE: DNA
<213> ORGANISM: Artificial Sequence
<220> FEATURE:
<223> OTHER INFORMATION: VEGFR2 Reverse

<400> SEQUENCE: 48
ccaagttcgt cttttcctgg gc                                          22

<210> SEQ ID NO 49
<211> LENGTH: 22
<212> TYPE: DNA
<213> ORGANISM: Artificial Sequence
<220> FEATURE:
<223> OTHER INFORMATION: OSR1 Forward

<400> SEQUENCE: 49
cctacacctg tgacatctgc ca                                          22

<210> SEQ ID NO 50
<211> LENGTH: 22
<212> TYPE: DNA
<213> ORGANISM: Artificial Sequence
<220> FEATURE:
<223> OTHER INFORMATION: OSR1 Reverse

<400> SEQUENCE: 50
gtgagtgtag cgtcttgtgg ac                                          22

<210> SEQ ID NO 51
<211> LENGTH: 22
```

```
<212> TYPE: DNA
<213> ORGANISM: Artificial Sequence
<220> FEATURE:
<223> OTHER INFORMATION: ACTA Forward

<400> SEQUENCE: 51
aggtcatcac catcggcaac ga                                              22

<210> SEQ ID NO 52
<211> LENGTH: 22
<212> TYPE: DNA
<213> ORGANISM: Artificial Sequence
<220> FEATURE:
<223> OTHER INFORMATION: ACTA1 Reverse

<400> SEQUENCE: 52
gctgttgtag gtggtctcgt ga                                              22

<210> SEQ ID NO 53
<211> LENGTH: 22
<212> TYPE: DNA
<213> ORGANISM: Artificial Sequence
<220> FEATURE:
<223> OTHER INFORMATION: aSMA Forward

<400> SEQUENCE: 53
ctatgcctct ggacgcacaa ct                                              22

<210> SEQ ID NO 54
<211> LENGTH: 22
<212> TYPE: DNA
<213> ORGANISM: Artificial Sequence
<220> FEATURE:
<223> OTHER INFORMATION: aSMA Reverse

<400> SEQUENCE: 54
cagatccaga cgcatgatgg ca                                              22

<210> SEQ ID NO 55
<211> LENGTH: 22
<212> TYPE: DNA
<213> ORGANISM: Artificial Sequence
<220> FEATURE:
<223> OTHER INFORMATION: SM22a Forward

<400> SEQUENCE: 55
tccaggtctg gctgaagaat gg                                              22

<210> SEQ ID NO 56
<211> LENGTH: 22
<212> TYPE: DNA
<213> ORGANISM: Artificial Sequence
<220> FEATURE:
<223> OTHER INFORMATION: SM22a Reverse

<400> SEQUENCE: 56
ctgctccatc tgcttgaaga cc                                              22

<210> SEQ ID NO 57
<211> LENGTH: 22
<212> TYPE: DNA
<213> ORGANISM: Artificial Sequence
<220> FEATURE:
<223> OTHER INFORMATION: TGFB1 Forward

<400> SEQUENCE: 57
```

```
tacctgaacc cgtgttgctc tc                                              22

<210> SEQ ID NO 58
<211> LENGTH: 22
<212> TYPE: DNA
<213> ORGANISM: Artificial Sequence
<220> FEATURE:
<223> OTHER INFORMATION: TGFb2 Reverse

<400> SEQUENCE: 58
gttgctgagg tatcgccagg aa                                              22

<210> SEQ ID NO 59
<211> LENGTH: 22
<212> TYPE: DNA
<213> ORGANISM: Artificial Sequence
<220> FEATURE:
<223> OTHER INFORMATION: TGFb2 Forward

<400> SEQUENCE: 59
aagaagcgtg ctttggatgc gg                                              22

<210> SEQ ID NO 60
<211> LENGTH: 22
<212> TYPE: DNA
<213> ORGANISM: Artificial Sequence
<220> FEATURE:
<223> OTHER INFORMATION: TGFb2 Reverse

<400> SEQUENCE: 60
atgctccagc acagaagttg gc                                              22

<210> SEQ ID NO 61
<211> LENGTH: 23
<212> TYPE: DNA
<213> ORGANISM: Artificial Sequence
<220> FEATURE:
<223> OTHER INFORMATION: TGFb3 Forward

<400> SEQUENCE: 61
ctaagcggaa tgagcagagg atc                                             23

<210> SEQ ID NO 62
<211> LENGTH: 22
<212> TYPE: DNA
<213> ORGANISM: Artificial Sequence
<220> FEATURE:
<223> OTHER INFORMATION: TGFb3 Reverse

<400> SEQUENCE: 62
tctcaacagc cactcacgca ca                                              22

<210> SEQ ID NO 63
<211> LENGTH: 22
<212> TYPE: DNA
<213> ORGANISM: Artificial Sequence
<220> FEATURE:
<223> OTHER INFORMATION: TGFbR1 Forward

<400> SEQUENCE: 63
gacaacgtca ggttctggct ca                                              22

<210> SEQ ID NO 64
<211> LENGTH: 22
<212> TYPE: DNA
<213> ORGANISM: Artificial Sequence
```

```
<220> FEATURE:
<223> OTHER INFORMATION: TGFbR1 Reverse

<400> SEQUENCE: 64
ccgccacttt cctctccaaa ct                                              22

<210> SEQ ID NO 65
<211> LENGTH: 22
<212> TYPE: DNA
<213> ORGANISM: Artificial Sequence
<220> FEATURE:
<223> OTHER INFORMATION: TGFbR2 Forward

<400> SEQUENCE: 65
gtctgtggat gacctggcta ac                                              22

<210> SEQ ID NO 66
<211> LENGTH: 22
<212> TYPE: DNA
<213> ORGANISM: Artificial Sequence
<220> FEATURE:
<223> OTHER INFORMATION: TGFbR2 Reverse

<400> SEQUENCE: 66
gacatcggtc tgcttgaagg ac                                              22

<210> SEQ ID NO 67
<211> LENGTH: 22
<212> TYPE: DNA
<213> ORGANISM: Artificial Sequence
<220> FEATURE:
<223> OTHER INFORMATION: FGF21 Forward

<400> SEQUENCE: 67
ctgcagctga aagccttgaa gc                                              22

<210> SEQ ID NO 68
<211> LENGTH: 22
<212> TYPE: DNA
<213> ORGANISM: Artificial Sequence
<220> FEATURE:
<223> OTHER INFORMATION: FGF21 Reverse

<400> SEQUENCE: 68
gtatccgtcc tcaagaagca gc                                              22

<210> SEQ ID NO 69
<211> LENGTH: 22
<212> TYPE: DNA
<213> ORGANISM: Artificial Sequence
<220> FEATURE:
<223> OTHER INFORMATION: NRG4 Forward

<400> SEQUENCE: 69
tgtggcattg gcggtcctag ta                                              22

<210> SEQ ID NO 70
<211> LENGTH: 22
<212> TYPE: DNA
<213> ORGANISM: Artificial Sequence
<220> FEATURE:
<223> OTHER INFORMATION: NRG4 Reverse

<400> SEQUENCE: 70
actgctcgtc tctaccaggt tg                                              22
```

```
<210> SEQ ID NO 71
<211> LENGTH: 22
<212> TYPE: DNA
<213> ORGANISM: Artificial Sequence
<220> FEATURE:
<223> OTHER INFORMATION: IL6 Forward

<400> SEQUENCE: 71
agacagccac tcacctcttc ag                                              22

<210> SEQ ID NO 72
<211> LENGTH: 22
<212> TYPE: DNA
<213> ORGANISM: Artificial Sequence
<220> FEATURE:
<223> OTHER INFORMATION: IL6 Reverse

<400> SEQUENCE: 72
ttctgccagt gcctctttgc tg                                              22

<210> SEQ ID NO 73
<211> LENGTH: 21
<212> TYPE: DNA
<213> ORGANISM: Artificial Sequence
<220> FEATURE:
<223> OTHER INFORMATION: ADIPOQ Forward

<400> SEQUENCE: 73
caggccgtga tggcagagat g                                               21

<210> SEQ ID NO 74
<211> LENGTH: 23
<212> TYPE: DNA
<213> ORGANISM: Artificial Sequence
<220> FEATURE:
<223> OTHER INFORMATION: ADIPOQ Reverse

<400> SEQUENCE: 74
ggtttcaccg atgtctccct tag                                             23
```

METHODS, COMPOSITIONS, AND KITS FOR PRODUCING BEIGE ADIPOCYTES AND TREATING METABOLIC DISORDERS

RELATED APPLICATIONS

This application is a continuation application based upon U.S. patent application Ser. No. 16/245,298, filed Jan. 11, 2019, which claims the benefit of priority under 35 U.S.C. § 119(e) to U.S. Provisional Application No. 62/616,507, filed Jan. 12, 2018. The entire contents of each are incorporated herein by reference.

GOVERNMENT SUPPORT

This invention was made with government support under Grant No. P30GM106391 awarded by the National Institutes of Health (NIH) and the National Institute of General Medical Sciences (NIGMS), Grant No. U54GM115516, awarded by the NIH, Grant No. P20GM121301, awarded by the NIH Centers of Biomedical Research Excellence (CO-BRE), and Grant No. U54GM115516, awarded by the NIH. The government has certain rights in the invention.

INCORPORATION-BY-REFERENCE OF SEQUENCE LISTING

The contents of the sequence listing text file named "136191-51702_SL.txt", which was created on Feb. 4, 2022 and is 14,201 bytes in size, is hereby incorporated by reference in its entirety.

BACKGROUND

The consumption of high caloric food coupled to a sedentary lifestyle has triggered a global rise in obesity, which is closely associated with an increased risk for diabetes, stroke and heart disease[1,2]. Diet and exercise alone are often not enough to sustain long-term weight loss as body weight can become biologically imprinted in the chronically obese[3].

New methods for producing therapies that target metabolic syndromes are needed.

BRIEF SUMMARY

Provided herein are, inter alia, methods, compositions, and kits for producing adipocyte populations such as beige adipocyte populations. Also included are methods and compositions for increasing the level of adipocyte populations (e.g., beige adipocyte populations) in a subject, as well as methods and compositions for treating subjects who are overweight, obese, or who have diabetes, or pre-diabetes.

In an aspect, a method of producing a beige adipocyte population is provided. In embodiments, the method comprises contacting a mesenchymal stem cell (MSC) population with an effective amount of IL-4, a TGF-β inhibitor, and/or an adipogenic differentiation compound. In embodiments, the method comprises contacting an MSC population with an effective amount of interleukin 4 (IL-4); and/or a transforming growth factor beta (TGF-β) inhibitor. In embodiments, the method comprises contacting an MSC population with an effective amount of an adipogenic differentiation compound.

In aspects, provided herein is a method of producing a beige adipocyte population, the method comprising, (a) obtaining a cell population from a subject; (b) producing a pluripotent stem cell (PSC) population (an induced pluripotent stem cell iPSC) from the cell population; (c) producing a splanchnic mesoderm cell population from the PSC population; (d) producing an MSC population from the splanchnic mesoderm cell population; and (e) producing the beige adipocyte population from the MSC population.

Included herein is a method of preventing or treating obesity or a metabolic syndrome in a subject in need thereof. In embodiments, the method comprises administering to the subject an effective amount of a population of beige adipocytes produced by a method disclosed herein, or a factor obtained from the population of beige adipocytes produced by a method disclosed herein. In embodiments, the method comprises administering to the subject an effective amount of IL-4 and a TGF-β inhibitor.

In an aspect, provided herein is a method of increasing the level of a beige adipocyte population in a subject in need thereof. In embodiments the method comprises administering to the subject an effective amount of IL-4 and a TGF-β inhibitor.

Included herein is a method of reducing the weight or body mass index of an overweight subject. The method comprising administering the population of beige adipocytes produced of the methods herein to the subject.

In an aspect, a kit for producing a beige adipocyte population is provided. In embodiments, the kit comprises (i) cell culture media or a cell culture medium; (ii) IL-4; and (iii) a TGF-β inhibitor.

DESCRIPTION OF THE DRAWINGS

FIG. 1A is a graph depicting qPCR analysis of iPSCs derived from human skin fibroblasts obtained from Applied StemCell (ASE-9202) differentiated into mesoderm with Stemdiff Mesoderm Induction Medium (MIM) at different starting cell densities (day 5). Data normalized to ASE-9202 iPSCs (day 0). Data are expressed as mean±SD. FIG. 1B is a graph depicting PCR analysis for markers that define specific mesoderm sub-compartments. iPSCs differentiated in MIM show predominant expression of FOXF1 transcript (day 5, qPCR), indicative of splanchnic mesoderm. Data are expressed as mean±SD of three replicates. FIG. 1C is an image of a Western blot time course of FOXF1 protein during mesoderm induction. iPSCs differentiated in MIM induce expression of FOXF1 protein, as determined by Western blot. β-Tubulin is the loading control. FIG. 1D are images of immunofluorescence staining with anti-FOXF1 antibody (red) and counterstaining with DAPI (blue). Scale bar=100 μm. Treatment with MIM results in >95% FOXF1+ cells (red), as determined by immunofluorescence staining (n=3, 203 images, representative image shown). Scale bar, 100 mm. Counterstaining with DAPI (blue).

FIG. 2A depicts flow cytometry analysis of MSC and perivascular markers (red) of iPSCs differentiated into FD-MSCs (pass 6, day 30) with MesenCult™-ACF. Isotype controls shown in blue. (blue). FIG. 2B is a graph depicting a qPCR timecourse of skeletal (ACTA1) and smooth muscle markers (ACTA2 and SM22A) during differentiation of FOXF1+ mesoderm to MSCs (bars for PSC, Pass 0, Pass 1, Pass 2, Pass 3, Pass 4, and Pass 5 appear from left to right in the graph). qPCR results demonstrated increased smooth muscle marker (uSMA and SM22a) expression during differentiation of FOXF1+ mesoderm toward MSCs. Data are expressed as mean±SD of three replicates. FIG. 2C are images depicting immunostaining of FD-MSCs with anti-smooth muscle marker antibodies. Counterstaining with DAPI (blue). Scale bar=25 µm. FIG. 2D are images depicting alzerian red staining (calcium deposition) of FD-MSCs differentiated into osteoblasts. Scale bar=200 µm. FIG. 2E is an image depicting alcian blue staining (proteoglycan deposition) of FD-MSCs differentiated into chondrocytes. Representative images shown. Scale bar=50 µm.

FIGS. 3A-3O depict TGF-β signaling in FD-MSCs inhibits adipocyte formation.

FIG. 3A depicts qPCR analysis of TGF-β ligands and receptors during generation of FD-MSCs (bars for PSC, Pass 0, Pass 1, Pass 3, and Pass 6 appear from left to right in the graph). Data are expressed as mean±SD of three replicates. FIG. 3K are images showing that PLIN (red) and PPARγ2 (green) staining of FD-MSCs induced into mature adipocytes with SB before and during adipogenic differentiation (left). Phase contrast microscopy (right) showing morphology of FD-MSC derived adipocytes treated with SB before and during adipogenic differentiation. Scale bars, 50 µm. FIG. 3L are images showing that PPARγ2+ staining (green) of FD-MSCs induced into mature adipocytes with SB. DAPI (blue) at left and PPARγ2+/DAPI overlay at right. Scale bar, 50 µm. FIG. 3M is a bar graph depicting the quantitation of PLIN+ and PPARγ2+ cells (as shown in FIGS. 3K and 3L) expressed as the means±SDs (n=4, 203 images each). FIG. 3N depict flow cytometry analysis showing increased expression of beige adipogenic precursor markers in FD-MSCs treated with SB (2 days). Isotype controls (blue). FIG. 3O are images depicting immunofluorescence staining of EBF2 (top, green) of FD-MSCs untreated (left) or treated (right) with SB (2 days). DAPI (blue, bottom). Scale bar, 50 µm.

FIG. 4A is a qPCR timecourse analysis (UCP1) of FD-MSCs during generation of adipocytes with or without SB431542. Data are expressed as mean±SD of three replicates is shown. FIG. 4B is an image of a Western blot analysis timecourse of adipocytes derived from FD-MSCs with the brown/beige adipogenic cocktail. β-tubulin was a loading control. FIG. 4C shows images depicting immunofluorescence imaging FD-MSCs (left, day 0) or FD-MSC-derived adipocytes (right, day 12) with antibodies against the mitochondrial proteins UCP1 (green) and COX-IV (red). Scale bar, 50 µm. FIG. 4D are images showing immunofluorescence imaging of FD-MSCs or adipocytes (day 12) immunostained with anti-PLIN antibody. DAPI shown in blue. Scale bar=200 µm. FIG. 4E are images qPCR analysis timecourse of common brown/beige adipogenic transcription factors and markers specific to beige or brown adipocytes (bars for Day 0, Day 3, Day 6, Day 9, Day 12, and Day 15 appear from left to right in the graph). Data are expressed as mean±SD for three replicates. FIG. 4F is a graph depicting mass spectrometry analysis of myosin proteins with increased expression in interscapular brown adipose tissue (bars for MYL1, MYH3, MYL6B, MYRS (MYLPF), MLRV (MYL2), MYH7, MYH8, and MYBPH appear from left to right in the graph). Data are normalized relative to expression in FD-beige adipocytes (N=3 adipocyte lysates per group). P values less than 0.001 are indicated by *. FIG. 4G are graphs depicting qPCR analysis timecourse for transcripts that encode anti-diabetic secreted factors. Results for ADIPOQ are divided by 10,000 for scaling purposes (bars for Day 0, Day 3, Day 6, Day 9, Day 12, and Day 15 appear from left to right in the graph). Data are expressed as mean±SD for three replicates. FIG. 4H are images depicting BODIPY stain of FD-beige adipocytes (Day 12) pretreated with SB431542 or IL-4 for 2 days prior to adipogenic differentiation. Scale bar=100 µm. FIG. 4I is a graph depicting quantitation of (FIG. 4H) with ImageJ software. N=4 (20× images). Data are expressed as mean±SD. P-values derived from Student's t-test. FIG. 4J is a graph depicting a qPCR of differentiating FD-beige adipocytes with IL-4 or IL-4+SB431542 pretreatment. Data are expressed as mean±SD for three replicates. FIG. 4K is a time course depicting differentiating FD-beige adipocytes with IL-4 or IL-4+SB431542 pretreatment. FIG. 4L are images of a Western blot analysis timecourse of differentiating FD-beige adipocytes pretreated with IL-4+SB431542 (two days) before apidogenic induction. FIG. 4M is a table depicting the ELISA-based measurement of anti-diabetic proteins secreted into culture medium (2 days) by FD-MSCs, iPSC-beige, and primary subcutaneous (subQ) adipocytes. Means±SDs of three replicates shown.

FIG. 5A is a graph depicting Seahorse XF analyzer profile of FD-MSCs and iPSC-beige adipocytes (day 14) treated with 1.25 mM oligomycin (Oligo), 1 µM para-rifluoromethoxy carbonyl cyanide phenylhydrazone (FCCP), and 2 µM rotenone/antimycin (Rot/Anti) at the indicated times (arrowheads). Means±SDs of three replicates per time point shown. FIG. 5B is a graph depicting a quantitative summary of Seahorse analysis shown in (A). Data are expressed as mean of 3 time point measurements±SD. FIG. 5C are images depicting a JC-1 assay on live cells to indicate mitochondrial membrane polarization. iPSC-beige adipocytes (green) compared to FD-MSCs (red). Representative image from 3 experiments shown. Scale bar=100 µm. FIG. 5D is a graph depicting the quantitation of JC-1 staining as shown in (FIG. 5C). Data are expressed as mean of 3 experiments±SD. Student t tests was used to determine P value of FD-beige relative to FD-MSCs. FIG. 5E is a graph depicting the quantitative summary of the Seahorse XF analysis shown in (FIG. 5A) with the addition of two primary subcutaneous beige and white cell lines. Means±SDs of three replicates per time point shown. FIG. 5F depicts an image of a Western blot time course of adrenoceptor beta 1 (ADRB1) and ADRB3 during iPSC-beige adipocyte differentiation, with β-tubulin as a loading control. HEPG2 and HL-60 cell lines serve as positive controls. FIG. 5G is a graph depicting qPCR of iPSC-beige adipocytes and primary subcutaneous beige cell lines treated with CL316,243 (1 μM) for 4 hr. Means±SDs of three replicates shown. *p<0.05 using Student's t test. FIG. 5H depicts a graph depicting qPCR of differentiating iPSC-beige adipocytes treated with CL316,243 (1 μM) for 24, 48, and 72 hr with and without rosiglitazone (1 mM). Means±SDs of three replicates shown. *p<0.03 using Student's t test. FIG. 5I depicts an image of a Western blot analysis time course of iPSC-beige adipocytes with rosiglitazone removed from maintenance medium from days 12 to 20. (3-Tubulin serves as a loading control. FIG. 5J is a graph depicting the quantitative summary of the Seahorse XF analyzer profile of iPSC-beige adipocytes after 4-hr treatment with CL316,243 (1 μM, day 16). Means±SDs of three replicates per time point and Student's p value shown. FIG. 5K depicts a graph of the quantitative summary of the Seahorse XF analyzer profile of primary subcutaneous beige cells (line 1) after 4-hr treatment with CL316,243 (1 μM, day 16). Means±SDs of three replicates per time point and Student's p value shown. FIG. 5L depicts a graph of the quantitative summary of fluorescence microplate kinetic reading of iPSC-beige and -whitened beige adipocytes treated with and without CL316,243 (1 μM) for 2 hr before fatty acid uptake reading for an additional 2 hr. Means±SDs of four replicates per time point and Student's p value shown.

FIG. 6A depicts flow cytometry analysis of MSC and preadipocyte markers expressed on T2 diabetic and reprogrammed pre-adipocytes. FIG. 6B are images depicting fluorescence microscopy of BODIPY stained FD-MSCs differentiated for 12 days with and without SB431542 (SB) during pretreatment (2 days) or induction (12 days). Representative images shown. Scale bar=100 μm. FIG. 6C is a graph depicting the quantitation of (FIG. 6B) by image J software as measured by relative integrated density expressed as mean±SD (n=3 20× images). Student's p value shown. FIG. 6D are graphs depicting qPCR analysis timecourse of common brown/beige adipogenic transcription factors and markers specific to beige or brown adipocytes (bars for Day 0, Day 3, Day 6, Day 9, and Day 12 appear from left to right in the graph). Data are expressed as mean±SD. FIG. 6E are images depicting a Western blot time course of T2 primary-adipogenic precursors and T2-iPSC-adipogenic precursors differentiated into mature adipocytes. FIG. 6F is a graph depicting a quantitative summary of Western blot analysis timecourse of type 2 primary and type 2 FD-beige adipocytes shown in 6E. Quantitation of UCP1 protein expression shown in (G); three replicate samples pooled per data point. Data are normalized relative to β-tubulin. FIG. 6G is a graph depicting a quantitative summary of Seahorse XF analyzer profile of live type 2 primary and type 2 FD-beige adipocytes (day 14). Means±SDs of three replicates per time point shown. *p<0.05 and **p<0.01 using Student's t test. FIG. 6H depict images of Tra-1-60+ live cell staining (upper) and phase contrast (lower) of a representative iPSC colony generated from subcutaneous adipogenic precursors of a 76-year-old patient with type 2 diabetes. Scale bar, 100 μm. FIG. 6I depict flow cytometry of MSC and adipocyte precursor (AP) markers expressed on T2 primary-adipogenic precursors and T2-iPSC-adipogenic precursors. FD-MSCs were treated with SB (5 mM) for 2 days to generate T2-iPSC-adipogenic precursors. FIG. 6J are images depicting PPARγ2+ staining (green) of T2 primary and T2 iPSC-beige adipogenic precursors induced into mature adipocytes with the beige adipogenic cocktail. Scale bar, 50 μm. FIG. 6K is a graph depicting the quantitation of PPARγ2+ cells (as shown in FIG. 6J) expressed as means±SDs (n=3, 203 images each). Student's p value shown. FIG. 6L are images depicting fluorescence microscopy of BODIPY-stained T2 primary-adipogenic precursors and T2-iPSC-adipogenic precursors after differentiation into adipocytes with the beige induction protocol (12 days). Representative images shown. Scale bar, 100 μm.

FIG. 7A is a schematic representation showing experimental design to test for anti-diabetic secretion potential of iPSC-beige adipocytes. FIG. 7B is a Western blot analysis of phospho-AKT in T2 primary-beige adipocytes treated with insulin in the presence of T2 primary-beige conditioned medium (lanes 4-8) or T2 iPSC-beige adipocyte conditioned medium (lanes 9-12). FIG. 7C is a quantitation of phospho-AKT protein expression (shown in (6I)). Data are normalized to β-actin protein. Data are expressed as mean±SD of four replicates. Student's p value shown. FIG. 7D is a glucose uptake analysis of T2 primary-beige adipocytes treated with insulin in the presence of T2 primary-beige conditioned medium or T2 iPSC-beige adipocyte conditioned medium. Data are expressed as mean±SD and P values <0.05 are indicated by asterisks.

FIG. 8A is a graph depicting qPCR analysis of markers known to be expressed in splanchnic mesoderm that show increased expression in ASE-9902 iPSCs differentiated with Stemdiff MIM (day 5). Data are expressed as mean±SD of three replicates. FIG. 8B depicts Western blot analysis of skin-derived iPSCs differentiated with STEMdiff MIM over 5 days. FIG. 8C depicts a directed screen using previously described factors known to give rise to mesoderm tissue were used to determine medium compositions that give rise to FOXF1+ mesoderm. BMP4 (bone morphogenetic protein 4) in combination with CHIR99021 (CHIR, 1.5 μM) resulted in increased expression of FOXF1 (forkhead Box F1), whereas Activin A (ACT-A) or VEGFA (Vascular endothelial growth factor A) (VEGF) with CHIR had no response. Further combinations of BMP4 with ACT-A and VEGF demonstrated that BMP4 and VEGF in combination with CHIR lead to the highest expression of FOXF1. Data are expressed as mean±SD of 3 replicates shown. FIG. 8D depicts a graph showing the increasing the concentration of CHIR to 5 μM in combination with BMP4 and VEGF in an independent assay caused a decrease in the expression of FOXF1. Data are expressed as mean±SD of 3 replicates shown. FIG. 8E is a blot showing 1.5 μM CHIR in combination with VEGF and BMP4 lead to a significant increase in FOXF1 protein compared to StemDiff mesoderm induction medium (MIM). While 5 μM CHIR (+BMP4+VEGF) lead to similar levels of FOXF1 protein compared to Stemdiff MIM, this concentration of CHIR also induced expression of PDGFRα, a marker of paraxial mesoderm. Inhibition with the TGFβ inhibitor SB431542 (SB) blocked protein expression of FOXF1 and increased expression of the somatic marker IRX3. FIG. 8F is a graph depicting transcription of the somatic mesoderm marker IRX3 was low or absent from mesoderm produced by in house or StemDiff mesoderm induction mediums, however, additional inhibition with SB431542 induced transcription of the somatic mesoderm marker IRX3 and inhibited FOXF1 protein expression (FIG. 8E). Data are expressed as mean±SD of 3 replicates shown. FIG. 8G is a model showing that the presence or absence TGFβ signaling can specify either splanchinic or somatic mesoderm subcompartments, respectively.

FIG. 9A is a graph depicting qPCR analysis of UCP1 expression in human subcutaneous white preadipocytes differentiated with the beige adipogenic cocktail with or without SB413542. Data are expressed as mean±SD of three replicates. FIG. 9B is a graph depicting qPCR analysis of iPSC-beige adipocytes (day 9) and primary beige (day 9) or brown adipocytes (day 7). Data are expressed as mean±SD of 3 replicates. FIG. 9C is a graph depicting Mass spectrometry analysis of myosin proteins with increased expression in interscapular brown adipose tissue. Data are normalized relative to expression in iPSC-beige adipocytes (N=3 adipocyte lysates per group). P values less than 0.001 are indicated by an asterisk. FIG. 9D is an image of a Western blot analysis showing timecourse of adipocytes differentiated from FD-MSCs with the brown/beige adipogenic cocktail. FIG. 9E-9L depict derivation of beige adipocytes from CD34+ cord blood. iPSCs derived from cord blood were differentiated into beige adipocytes using the methods herein. FIG. 9E depicts flow cytometry analysis of MSC and perivascular markers (red) of iPSCs differentiated into FD-MSCs (pass 6) with MesenCult-ACF. Isotype controls shown in blue. FIG. 9F depict images showing fluorescence microscopy of BODIPY stained FD-MSCs (left) or FD-MSCs differentiated into adipocytes (right) for 12 days with 5NM SB431542 (SB) during pretreatment and induction. Representative images are shown. Scale bar=100 μm. FIG. 9G is a graph depicting qPCR analysis of common brown/beige adipogenic transcription factors and markers enriched in beige or brown adipocytes (day 12). Data are expressed as mean±SD of 3 replicates. FIG. 9H are images showing Primary urine-derived cells (top panel) were expanded and reprogrammed into Tra-1-60+ iPSCs (bottom panel). FIG. 9I are flow cytometry analysis of MSC and perivascular markers (red) of iPSCs differentiated into FD-MSCs (pass 6) with MesenCult-ACF. Isotype controls shown in blue. FIG. 9J are images showing primary urine-derived cells (left panels) and FD-MSCs derived from urine-derived iPSCs (right panels) induced with the brown/beige adipogenic cocktail of factors for 12 days. Phase contrast (upper) and immunofluorescence of BODIPY stained (lower) images shown. Results with primary urine-derived cells demonstrate that reprogramming is necessary to generate beige adipocytes. Scale bar=100 μm. FIG. 9K is a graph depicting qPCR analysis of common brown/beige adipogenic transcription factors and markers enriched in beige or brown adipocytes. Data are expressed as mean±SD of 3 replicates. FIG. 9L depicts a Western blot analysis of primary urine-derived cells and FD-MSCs induced with the brown/beige adipogenic cocktail of factors (day 12 shown).

FIG. 10A depicts qPCR analysis of PDGFRα. FIG. 10B depicts qPCR analysis of EBF2. FIG. 10C depicts qPCR analysis of PPARG1, PPARG2 and PPARG3. Data are expressed as mean±SD of 3 replicates.

FIG. 14A depicts qPCR analysis time course of common brown/beige adipogenic transcription factors and markers enriched in beige or brown adipocytes for T2 primary subcutaneous adipocytes (top) and T2 iPSC-beige adipocytes (bottom). Data are expressed as mean±SD of 3 replicates. FIG. 14B depicts UCP1 western blot analysis of T2 primary subcutaneous adipocytes and T2 iPSC-beige adipocytes following 12 days of differentiation. Two additional normal primary subcutaneous beige adipocytes are included as comparisons. β-tubulin serves as a loading control.

FIG. 15A shows a cumulative chart of all primary preadipocytes and their donor characteristics. FIG. 15B shows flow cytometry analysis of PDGFRα surface expression in primary type 2 diabetic subcutaneous and omental adipogenic precursors. Isotype controls shown in blue. FIG. 15C shows fluorescence microscopy of BODIPY stained T2 primary adipocytes and iPSC-beige adipocytes following 12 days of differentiation. Representative images are shown. Scale bar=100 μm. FIG. 15D shows quantitation of lipid accumulation (as shown in (FIG. 15C)) by image J software as measured by relative integrated density expressed as mean±SD (n=3, 20× images). FIG. 15E shows quantitation of PPARγ2+ stained primary beige adipocytes and iPSC-beige adipocytes following 12 days of differentiation expressed as ±SD, (n=3, 20× images). FIG. 15F shows UCP1 qPCR analysis of T2 primary adipocytes and iPSC-beige adipocytes following 12 days of differentiation. Data are expressed as mean±SD of 3 replicates. FIG. 15G shows a Western blot analysis of T2 primary subcutaneous adipocytes (34 years old) and T2 iPSC-beige adipocytes (34 years old) following 12 days of differentiation. Two additional normal primary subcutaneous beige adipocytes are included for comparison. β-tubulin serves as a loading control. FIG. 15H shows Western blot analysis of T2 primary omental adipocytes (63 years old) and T2 iPSC-beige adipocytes (63 years old) following 12 days of differentiation. Non-diabetic primary subcutaneous beige adipocytes are included for comparison. β-tubulin serves as a loading control. FIG. 15I shows quantitative summary of Seahorse XF analyzer profile of live T2 primary subcutaneous adipocytes (34 years old) and T2 iPSC-beige adipocytes (day 14). Data are expressed as mean of 3 time point measurements±SD. P<0.01 using Student's t test. FIG. 15J shows quantitative summary of Seahorse XF analyzer profile of live T2 primary omental adipocytes (63 years old) and T2 iPSC-beige adipocytes (day 14). Data are expressed as mean of 3 time point measurements±SD. P<0.01 and *P<0.05 using Student's t test.

FIGS. 16A-16C show that iPSC-derived beige adipocytes from a 34 year old patient secrete factors that improve insulin sensitivity and glucose uptake in the primary subcutaneous adipocytes. FIG. 16A depicts a Western blot analysis of phospho-AKT in T2 subcutaneous adipocytes (34 years old) treated with insulin in the presence of T2 subcutaneous adipocyte conditioned medium (lanes 4-6) or T2 iPSC-beige adipocyte conditioned medium (lanes 10-12). FIG. 16B depicts quantitation of phospho-AKT protein expression (shown in (FIG. 16A)). Data are normalized to β-actin protein. Data are expressed as mean±SD. FIG. 16C depicts a graph of glucose uptake analysis of T2 subcutaneous adipocytes (34 years old) treated with insulin in the presence of T2 subcutaneous adipocyte conditioned medium or T2 iPSC-beige adipocyte conditioned medium. Data are expressed as mean±SD and values from Student's t test shown.

DETAILED DESCRIPTION

Figure 1A:
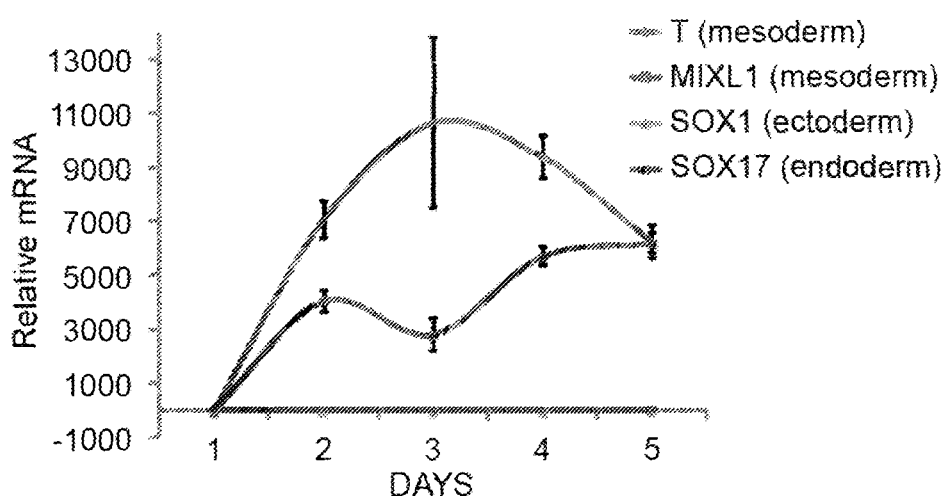
FIGS. 1A-1D depict the generation of FOXF1+ splanchnic mesoderm from iPSCs.

Provided herein, are, inter alia, methods, compositions and kits for producing adipocyte populations such as beige adipocyte populations, as well as methods and compositions for treating metatabolic disorders such as obesity and type II diabetes.

Behavioral interventions for the treatment of obesity have yet to deliver desired outcomes, thus introducing a need for molecular- and cellular-based therapies. In response to cold, beige adipocytes can be formed in subcutaneous white adipose tissue where they burn excess calories by converting energy stored in metabolic substrates to heat.

During weight gain, chronic periods of overeating result in the storage of lipids in white adipose tissue (WAT), which leads to cellular stress, inflammation and insulin resistance[4, 5]. New research strategies to address the public health risk of obesity are focusing on brown and beige adipose tissue. Both tissue types possess high metabolic activity that correlates positively with reduced risk for metabolic syndrome, making them appealing therapeutic targets[1, 6-8]. In response to cold stimulated release of norepinephrine by the sympathetic nervous system (SNS), brown and beige adipocytes become metabolically activated and expend energy stored in glucose and lipids to generate heat. This process, known as non-shivering thermogenesis, likely evolved in mammals to increase neonatal survival and provide warmth during cold temperatures[6].

Classical brown adipose tissue (BAT) develops during the fetal period as a permanent tissue, whereas beige adipose tissue is induced in subcutaneous WAT in response to cold or other thermogenic activators[6, 9]. In humans, BAT was originally thought to be restricted to newborns, however, human studies show that BAT is present in adults and its activity correlates inversely with body mass index[10]. Brown and beige adipocytes have multilocular lipid droplet morphology, high mitochondrial content and express uncoupling protein-1 (UCP1), which uncouples oxidative phosphorylation and increases proton-leak across the inner mitochondrial membrane, resulting in increased thermogenesis and energy expenditure. In addition to its active role in thermogenesis, a number of secreted factors derived from BAT, including FGF21, NRG4, IL6, ADIPOQ and others, have a positive impact on metabolic dysfunction in mice by targeting diabetes affected tissues, such as white adipose, skeletal muscle and the liver[11]

Thus, brown and beige adipose tissue represent promising therapeutic targets to treat metabolic dysfunction through increased energy expenditure and/or anti-diabetic secretion potential.

Modifying obesity and diabetes in humans by stimulating energy expenditure in adipose tissue with drugs has largely been unsuccessful, with the exception of Myrbetriq[12]. This β3 agonist can stimulate BAT activity and is currently used for treatment of overactive bladder, but would likely lead to minimal weight loss at the currently approved dose[12]. One potential alternative to drugs is to use cell-based therapies to supplement obese patients with additional brown or beige adipose tissue, their adipogenic precursors or secreted factors derived from these cells. Indeed, studies in mice have demonstrated that BAT transplantation increases insulin sensitivity, prevents diet-induced weight gain and can reverse preexisting obesity[13]. In humans BAT becomes more limited or absent with increasing age and weight gain and requires invasive methods to procure[14, 15]. While beige adipogenic precursors found in subcutaneous WAT are more easy to procure than those found in BAT, they have limited expansion potential and precursors from obese patients show a decreased capacity for adipocyte differentiation and a compromised ability for beige adipogenesis[16, 17]. One approach to overcome these obstacles is to generate patient matched brown or beige adipocytes from induced pluripotent stem cells (iPSCs). This process requires an understanding of the developmental origins of brown and beige adipose tissue and the creation of robust and efficient methods for their differentiation from iPSCs.

In mice, classical brown adipose arises developmentally from a Myf5+ precursor population of paraxial mesoderm, whereas the developmental origins of beige adipocytes are more enigmatic and can be simply described as being derived from an unknown Myf5− precursor population[18, 19] This population of cells ultimately gives rise to mural and vascular smooth muscle cells that generate a beige adipogenic precursor population[18]. Compared to infants, evidence from adult humans now suggests that several of the anatomical locations for classical BAT actually consist of adipocytes with a molecular signature more similar to beige adipose tissue (reviewed in[20]). Because brown and beige adipose depots may be stimulated by different signals and represent potentially distinct therapeutic targets, it is important to develop cellular models that represent both tissue types[20].

Provided herein are robust methods for generating a renewable source of human beige adipocytes from pluripotent stem cells (PSCs). In embodiments, these cells are developmentally derived from FOXF1+ splanchnic mesoderm and progress through an expandable perivascular-like mesenchymal stem cell (MSC) to form mature beige adipocytes that display a thermogenically active profile, including expression of uncoupling protein 1 (UCP1) concomitant with increased uncoupled respiration.

In embodiments, dysfunctional adipogenic precursors can be reprogrammed and differentiated into beige adipocytes with restored thermogenic function. In embodiments, this resource can be used to elucidate mechanisms that underlie the control of beige adipogenesis and generate useful cells for cellular-based therapies that target metabolic syndrome in humans.

In embodiments, the methods described herein produce metabolically active beige rather than brown adipocytes from iPSCs. In embodiments, compared to other methods, methods provided herein use an expandable mesenchymal stem cell to generate beige adipocytes. In contrast, other methods short circuit iPSC-derived mesoderm directly into beige/brown adipocytes. Because MSCs, like iPSCs, are highly expandable, more beige adipocytes can be produced easier for therapeutic applications.

In embodiments, the methods described herein provide a multistage methodology for generating highly expandable mural-like MSCs from iPSCs, their conversion into adipogenic precursors, and their subsequent differentiation into beige adipocytes. These beige adipocytes are formed largely using commercially available defined serum-free or serum-low medium conditions, which should increase reproducibility and provide a more accurate representation of beige cell development as it occurs naturally in mammals.

A number of aspects and advantages of the present invention are described in Su et al. entitled, "A Renewable Source of Human Beige Adipocytes for Development of Therapies to Treat Metabolic Syndrome," *Cell Reports* 25, 3215-3228 (2018), the entire contents of which is incorporated herein by reference in its entirety.

Definitions

The following definitions are included for the purpose of understanding the present subject matter and for constructing the appended patent claims. The abbreviations used herein have their conventional meanings within the chemical and biological arts.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

In embodiments, a "metabolic disease" or "metabolic syndrome" or "metabolic condition" is a disorder in which an error of metabolism, an imbalance in metabolism, or a sub-optimal metabolism occur. In embodiments, a metabolic disease described herein is a disease that can be treated through the modulation of metabolism, although the disease itself may or may not be caused by a specific metabolic defect. Such metabolic diseases may involve, for example, glucose and fatty acid oxidation pathways.

In embodiments, subjects with metabolic diseases to which the present disclosure can be applied are subjects who are diagnosed with, suspected of having, or at risk of having, a metabolic disease or condition. In embodiments, such subjects are in need of treatment with, e.g., a beige adipocyte population, IL-4, and/or a TGF-β inhibitor. In embodiments, methods of the disclosure may be applied to a subject who, at the time of treatment, has been diagnosed as having a metabolic disease or condition, or a subject who is considered to be at risk for having or developing a metabolic disease or condition.

Non-limiting examples of subjects in need of treatment for a metabolic disease include subjects who are overweight, or who have obesity, non-alcoholic fatty liver disease, diabetes, insulin-resistance, alcoholic fatty liver disease, dyslipidemia, steatosis (e.g., liver steatosis, heart steatosis, kidney steatosis, muscle steatosis), abetalipoproteinemia, glycogen storage disease, Weber-Christian disease, lipodystrophy; a liver disease such as liver inflammation, hepatitis, steatohepatitis, Hepatitis C, Genotype 3 Hepatitis C, Alpha 1-antitrypsin deficiency, acute fatty liver of pregnancy, and Wilson disease; a kidney disease; or a heart disease such as hypertension, ischemia, heart failure, or cardiomyopathy.

The term "obesity" as used herein is defined in the World Health Organization (WHO) classifications of weight. In embodiments, "underweight" for a human is having a BMI of less than 18.5 (subjects with such a BMI may optionally be referred to as "thin"). In embodiments, a healthy BMI is 18.5-24.9 (subjects with such a BMI may optionally be referred to as having "normal" weight). In embodiments, grade 1 overweight is 25.0-29.9 BMI (subjects with such a BMI may optionally be referred to as "overweight"). In embodiments grade 2 overweight is 30.0-39.0 BMI (subjects with such a BMI may optionally be referred to as "obese"). In embodiments, grade 3 overweight is greater than or equal to 40.0 BMI (subjects with such a BMI may optionally be referred to as "morbidly obese"). BMI is body mass index (morbid obesity) and is $kg/m^2$. Other measures of obesity include, but are not limited to, waist circumference, skinfold thickness and bioimpedance, which is based on the principle that lean mass conducts current better than fat mass because it is primarily an electrolyte solution.

The term "obesity-related condition" refers to any disease or condition that is caused by or associated with (e.g., by biochemical or molecular association) obesity or that is caused by or associated with weight gain and/or related biological processes that precede clinical obesity. Examples of obesity-related conditions include, but are not limited to, diabetes (e.g., type 1 diabetes, type 2 diabetes, and gestational diabetes), Syndrome X, hyperglycemia, hyperinsulinemia, impaired glucose tolerance, impaired fasting glucose, dyslipidemia, hypertriglyceridemia, insulin resistance, hypercholesterolemia, atherosclerosis, coronary artery disease, peripheral vascular disease, and hypertension.

In embodiments, an antibody described herein may be a polyclonal antisera or monoclonal antibody. The term antibody may include any of the various classes or sub-classes of immunoglobulin (e.g., IgG, IgA, IgM, IgD, or IgE derived from any animal, e.g., any of the animals conventionally used, e.g., sheep, rabbits, goats, or mice, or human), e.g., the antibody comprises a monoclonal antibody, e.g., a TGF-β monoclonal antibody.

An "isolated antibody," as used herein, is intended to refer to an antibody that is substantially free of other antibodies having different antigenic specificities (e.g., an isolated antibody that specifically binds TGF-β and is substantially free of antibodies that specifically bind antigens other than TGF-β). Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

In embodiments, a TGF-β antibody is a humanized antibody, wherein the antibody is from a non-human species, whose protein sequence has been modified to increase its similarity to antibody variants produced naturally in humans. Generally, a humanized antibody has one or more amino acid residues introduced into it from a source which is non-human.

An "antibody fragment" comprises a portion of an intact antibody, preferably the antigen binding and/or the variable region of the intact antibody. Non-limiting examples of antibody fragments include Fab, Fab*, F(ab')$_2$ and Fv fragments; diabodies; linear antibodies; single-chain antibody molecules and multispecific antibodies formed from antibody fragments.

By "antigen" is defined as a molecule that provokes an immune response. This immune response may involve either antibody production, or the activation of specific immunologically-competent cells, or both. For example, any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein.

By, "small molecule" may be referred to broadly as an organic, inorganic or organometallic compound with a low molecular weight compound (e.g., a molecular weight of less than about 2,000 Da or less than about 1,000 Da). The small molecule may have a molecular weight of less than about 2,000 Da, a molecular weight of less than about 1,500 Da, a molecular weight of less than about 1,000 Da, a molecular weight of less than about 900 Da, a molecular weight of less than about 800 Da, a molecular weight of less than about 700 Da, a molecular weight of less than about 600 Da, a molecular weight of less than about 500 Da, a molecular weight of less than about 400 Da, a molecular weight of less than about 300 Da, a molecular weight of less than about 200 Da, a molecular weight of less than about 100 Da, or a molecular weight of less than about 50 Da.

In embodiments, an inhibitory oligonucleotide (e.g., a TGF-β inhibitor that is an oligonucleotide) is an antisense oligonucleotide (e.g., an antisense oligodeoxynucleotide), a double-stranded RNA, a siRNA, a shRNA, a miRNA, or an antisense RNA, or a portion thereof, or a mimetic thereof, that when administered to a mammalian cell results in a decrease (e.g., by 10%, 25%, 50%, 75%, or even 90-100%) in the expression of a target gene (such as TGF-β, a TGF-β receptor, or a member of the TGF-β signaling pathway that is downstream of a TGF-β receptor).

As defined herein, the term "inhibition," "inhibit," "inhibiting" and the like in reference to a protein-inhibitor (e.g., a TGF-β inhibitor) interaction means negatively affecting (e.g., decreasing) the activity or function of the protein (e.g., decreasing the activity or amount of TGF-β, decreasing the ability of TGF-β to bind to a receptor, decreasing the ability of a receptor to bind TGF-β, or decreasing TGF-β signaling upon the binding of TGF-β to a receptor) relative to the activity or function of the protein in the absence of the inhibitor. In embodiments, inhibition refers to reduction of a disease or symptoms of disease (e.g., metabolic disorder). In embodiments, inhibition includes, at least in part, partially or totally blocking stimulation, decreasing, preventing, or delaying activation, or inactivating, desensitizing, or down-regulating signal transduction or enzymatic activity or the amount of a protein (e.g., a TGF-β). Similarly an "inhibitor" is a compound or protein that inhibits a target by binding, partially or totally blocking, decreasing, preventing, delaying, inactivating, desensitizing, or down-regulating activity.

By "PPAR-γ" is meant peroxisome proliferator-activator receptor gamma. In embodiments, PPAR-γ regulates fatty acid storage and glucose metabolism. In embodiments, the genes activated by PPAR-γ stimulate lipid uptake and adipogenesis by fat cells. Many naturally occurring agents directly bind with and activate PPAR-γ, including various polyunsaturated fatty acids.

By "UCP1" is meant uncoupling protein 1 (also referred to as thermogenin). In embodiments, UCP1 is a protein found in the mitochondria. In embodiments, UCP1 is used to generate heat. UCPs are transmembrane proteins that decrease the proton gradient generated in oxidative phosphorylation, by increasing the permeability of the inner mitochondrial membrane, allowing protons that have been pumped into the intermembrane space to return to the mitochondrial matrix.

The term "disease" refers to any deviation from the normal health of a mammal and includes a state when disease symptoms are present, as well as conditions in which a deviation (e.g., metabolic dysfunction or metabolic disorder) has occurred, but symptoms are not yet manifested.

"Patient" or "subject in need thereof" refers to a living member of the animal kingdom suffering from or who may suffer from the indicated disorder. In embodiments, the subject is a member of a species comprising individuals who may naturally suffer from the disease. In embodiments, the subject is a mammal. Non-limiting examples of mammals include rodents (e.g., mice and rats), primates (e.g., lemurs, bushbabies, monkeys, apes, and humans), rabbits, dogs (e.g., companion dogs, service dogs, or work dogs such as police dogs, military dogs, race dogs, or show dogs), horses (such as race horses and work horses), cats (e.g., domesticated cats), livestock (such as pigs, bovines, donkeys, mules, bison, goats, camels, and sheep), and deer. In embodiments, the subject is a human.

The terms "subject," "patient," "individual," etc. are not intended to be limiting and can be generally interchanged. That is, an individual described as a "patient" does not necessarily have a given disease, but may be merely seeking medical advice.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

As used in the description herein and throughout the claims that follow, the meaning of "a," "an," and "the" includes plural reference unless the context clearly dictates otherwise.

As used herein, "treating" or "treatment" of a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean inhibiting the progression of the condition, disorder or disease, slowing the progression of the condition, disorder or disease temporarily, although in some instances, it involves halting the progression of the condition, disorder or disease permanently.

As used herein, the terms "treat" and "prevent" are not intended to be absolute terms. In embodiments, treatment can refer to a 10%, 20%, 30%, 40%, 50%, 60%, 70%, 80%, 90%, or 100% reduction in the severity of an established disease, condition, or symptom of the disease or condition. In embodiments, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. In embodiments, references to decreasing, reducing, or inhibiting include a change of 10%, 20%, 30%, 40%, 50%, 60%, 70%, 80%, 90% or greater as compared to a control level and such terms can include but do not necessarily include complete elimination. In embodiments, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," etc. refer to the amount of an agent that is sufficient to achieve a desired effect, as described herein. In embodiments, the term "effective" when referring to an amount of cells or a therapeutic compound may refer to a quantity of the cells or the compound that is sufficient to yield an improvement or a desired therapeutic response without undue adverse side effects (such as toxicity, irritation, or allergic response) commensurate with a reasonable benefit/risk ratio when used in the manner of this disclosure. In embodiments, the term "effective" when referring to the generation of a desired cell population may refer to an amount of one or more compounds that is sufficient to result in or promote the production of members of the desired cell population, especially compared to culture conditions that lack the one or more compounds.

As used herein, the term "pharmaceutically acceptable salt," is a salt formed from, for example, an acid and a basic group of an apilimod composition. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis-(2-hydroxy-3-naphthoate)) salts. In a preferred embodiment, the salt of apilimod comprises methanesulfonate.

Methods of Producing Beige Adipocyte Populations

Provided herein are methods of producing a beige adipocyte population. In some embodiments, the method comprises contacting an MSC population with an effective amount of IL-4 and/or a TGF-β inhibitor. In embodiments, the MSC population is contacted with an effective amount of IL-4. In embodiments, the MSC population is contacted with an effective amount of a TGF-β inhibitor. In embodiments, the amount of the IL-4 in combination with the amount of the TGF-β inhibitor is effective. In embodiments, the amount of the IL-4 is less than would be effective if it was used without the TGF-β inhibitor. In embodiments, the amount of the TGF-β inhibitor is less than would be effective if it was used without the IL-4.

In embodiments, the MSC population is contacted with the IL-4 and the TGF-β inhibitor concurrently.

In embodiments, the method further comprises culturing the MSC population in a cell culture medium that comprises the IL-4 and the TGF-β inhibitor.

In embodiments, the TGF-β inhibitor binds to TGF-β or a TGF-β receptor.

In embodiments, the TGF-β inhibitor binds to a TGF-β Type I or Type II receptor.

In embodiments, the TGF-β inhibitor binds to a protein that is downstream of a TGF-β superfamily Type I activing receptor-like kinase (ALK) receptor.

In embodiments, the TGF-β inhibitor binds to SMAD anchor for receptor activation (SARA).

In embodiments, the TGF-β inhibitor binds to any one of, or any combination of 2 or 3 of, or all 4 of SMAD1, SMAD4, SMAD5, and/or SMAD8.

In embodiments, the TGF-β inhibitor binds to SMAD1. In embodiments, the TGF-β inhibitor binds to SMAD4. In embodiments, the TGF-β inhibitor binds to SMAD5. In embodiments, the TGF-β inhibitor binds to SMAD8.

In embodiments, the TGF-β inhibitor binds to SMAD2 and/or SMAD3. In embodiments, the TGF-β inhibitor binds to SMAD2. In embodiments, the TGF-β inhibitor binds to SMAD3. In embodiments, the TGF-β inhibitor binds to SMAD2 and SMAD3.

In embodiments, the TGF-β inhibitor is a small molecule, an antibody or a fragment thereof, an oligonucleotide, an aptamer, or a peptide. In embodiments, the TGF-β inhibitor is a small molecule. In embodiments, the TGF-β inhibitor is an antibody, or fragment thereof.

In embodiments, the TGF-β inhibitor is an oligonucleotide. In embodiments, the TGF-β inhibitor is an aptamer. In embodiments, the TGF-β inhibitor is a peptide.

In embodiments, the TGF-β inhibitor is an antagonist antibody. An "antagonist antibody" or a "blocking antibody" is one that inhibits or reduces a biological activity of the antigen it binds to. In embodiments, blocking antibodies or antagonist antibodies substantially or completely inhibit the biological activity of the antigen. In embodiments, an anti-TGF-β antibody binds to and blocks the interaction of TGF-β with its receptor, and thus the signaling. In embodiments an antibody binds to a receptor of TGF-β.

In embodiments, the TGF-β inhibitor is lerdelimumab, metelimumab, fresolimumab, LY2382770, trabedersen, lucanix, disitertide, galunisertib, TEW-7197, PF-03446962, LY3022859, or SB431542.

In embodiments, the TGF-β inhibitor is an antibody. In embodiments, the TGF-β antibody is lerdelimumab. Lerdelimumab specifically binds to TGF-β2 and is described in Cordeiro, M. *Curr Opin Mol Ther.* 2003 April; 5(2):199-203, which is incorporated herein by reference in its entirety.

In embodiments, the TGF-β antibody is metelimumab. Metelimumab specifically binds TGF-β1 and is described in Bonafoux, D. and Lee, W. *Expert Opin Ther Pat.* 2009 December; 19(12):1759-69, which is incorporated herein by reference in its entirety.

In embodiments, the TGF-β antibody is fresolimumab. Fresolimumab specifically binds TGF-β1, TGF-β2 and TGF-β3, and is described in Morris, J. et al. *PLoS One.* 2014 Mar. 11; 9(3):e90353, which is incorporated herein by reference in its entirety.

In embodiments, the TGF-β antibody is LY2382770. LY2382770 is a TGFβ1 neutralizing antibody and is described in Breyer, M. and Susztak, K. *Nat Rev Drug Discov.* 2016 August; 15(8): 568-588, which is incorporated herein by reference in its entirety.

In embodiments, the TGF-β antibody is PF-03446962. PF-03446962 binds to TGF-β receptor ALK1 and is described in Necchi, A. et al. *Invest New Drugs.* 2014 June; 32(3):555-60, which is incorporated herein by reference in its entirety.

In embodiments, the TGF-β antibody is LY3022859. LY3022859 is an anti-TGFβRII IgG1 monoclonal antibody and is described in Tolcher, A. et al. *Cancer Chemother Pharmacol.* 2017 April; 79(4):673-680, which is incorporated herein by reference in its entirety.

In embodiments, the TGF-β inhibitor is an oligonucleotide (e.g., Trabedersen). The sequence for Trabedersen is 5'-CGGCATGTCTATTTTGTA-3' (SEQ ID NO: 1), which binds to TGF-β2 mRNA. Trabedersen is described in Jaschinski, F. et al. *Curr Pharm Biotechnol.* 2011 December; 12(12):2203-13, which is incorporated herein by reference in its entirety.

In embodiments, the TGF-β inhibitor is a vaccine (e.g., lucanix). Lucanix is comprised of 4 transforming growth factor (TGF)-β2-antisense gene-modified, irradiated, allogeneic NSCLC cell lines and is described in Giaccone, G. et al. *Eur J Cancer.* 2015 November; 51(16):2321-9, which is incorporated herein by reference in its entirety.

In embodiments, the TGF-β inhibitor is a small molecule. In embodiments, the small molecule is disitertide, the structure of which is:

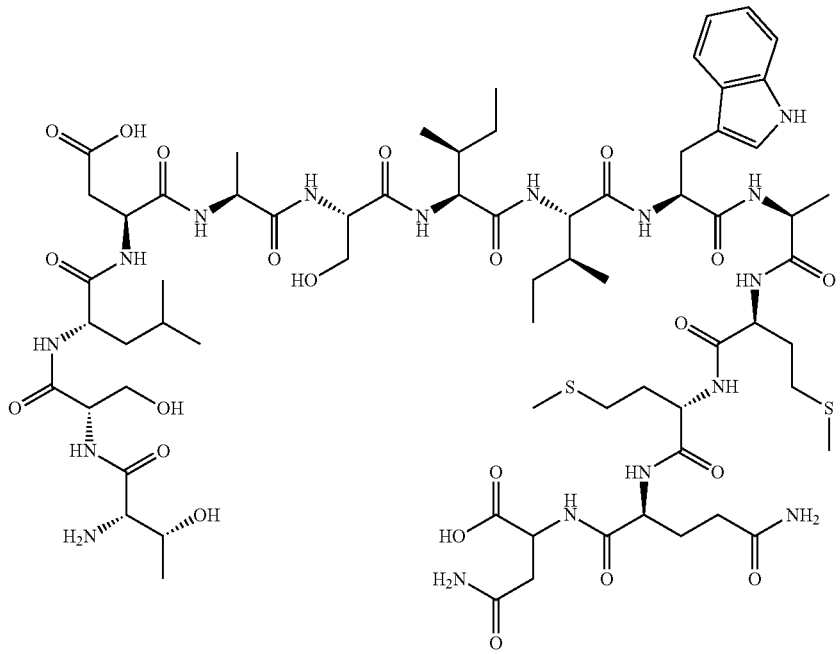 [SMILES: CC[C@H](C)[C@H](NC(=O)[C@H](CO)NC(=O)[C@H](C)NC(=O)[C@H](CC(=O)O)NC(=O)[C@H](CC(C)C)NC(=O)[C@H](CO)NC(=O)[C@@H](N)[C@@H](C)O)C(=O)N[C@H](C(=O)N[C@@H](Cc1c[nH]c2ccccc12)C(=O)N[C@@H](C)C(=O)N[C@@H](CCSC)C(=O)N[C@@H](CCSC)C(=O)N[C@@H](CCC(N)=O)C(=O)NC(CC(N)=O)C(=O)O)[C@@H](C)CC]

In embodiments, the TGF-β inhibitor is a small molecule. In embodiments, the small molecule is galunisertib, the structure of which is:

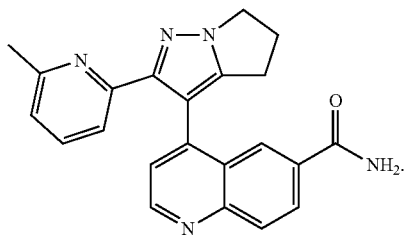 [SMILES: Cc1cccc(-c2nn3c(c2-c2ccnc4ccc(C(N)=O)cc24)CCC3)n1]

In embodiments, the TGF-β inhibitor is a small molecule. In embodiments, the small molecule is TEW-7197, the structure of which is:

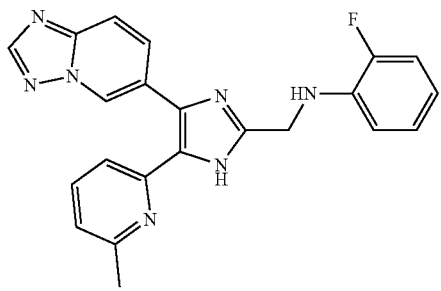 [SMILES: Cc1cccc(-c2[nH]c(CNc3ccccc3F)nc2-c2ccc3ncnn3c2)n1]

In embodiments, the TGF-β inhibitor is a small molecule. In embodiments, the small molecule is SB431542, the structure of which is:

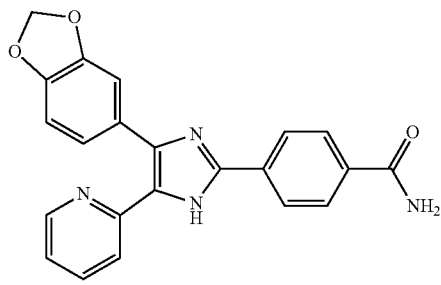 [SMILES: NC(=O)c1ccc(-c2nc(-c3ccc4c(c3)OCO4)c(-c3ccccn3)[nH]2)cc1]

In embodiments, the TGF-β inhibitor is an antibody. In embodiments, the TGF-β inhibitor is lerdelimumab, or fragment thereof. In embodiments, the TGF-β inhibitor is metelimumab, or fragment thereof. In embodiments, the TGF-β inhibitor is fresolimumab, or fragment thereof. In embodiments, the TGF-β inhibitor is LY2382770.

In embodiments, the TGF-β inhibitor is trabedersen. In embodiments, the TGF-β inhibitor is lucanix. In embodiments, the TGF-β inhibitor is disitertide. In embodiments, the TGF-β inhibitor is galunisertib. In embodiments, the TGF-β inhibitor is TEW-7197. In embodiments, the TGF-β inhibitor is PF-03446962. In embodiments, the TGF-β inhibitor is LY3022859. In embodiments, the TGF-β inhibitor is SB3431542.

In embodiments, a method for producing beige adipocytes includes contacting the MSC population with an adipogenic differentiation compound.

In embodiments, the MSC population is contacted with the TGF-β inhibitor, the IL-4, or a combination thereof to produce a preadipocyte population, and the preadipocyte population is contacted with the adipogenic differentiation compound.

In embodiments, the MSC population is cultured in a cell culture medium comprising the TGF-β inhibitor, the IL-4, or a combination thereof for at least about 24 hours to produce a preadipocyte population, and the preadipocyte population is contacted with the adipogenic differentiation compound.

In aspects, provided herein is a method of producing a beige adipocyte population. In embodiments, the method comprises contacting an MSC population with an effective amount of an adipogenic differentiation compound.

In embodiments, the adipogenic differentiation compound comprises a PPAR-γ activator.

In embodiments, the PPAR-γ activator comprises a thiazolidinedione.

In embodiments, the PPAR-γ activator comprises pioglitazone, rosiglitazone, lobeglitazone, ciglitazone, darglitazone, englitazone, netoglitazone, rivoglitazone, or troglitazone.

In embodiments, the adipogenic differentiation compound comprises 3,3',5-Triiodo-L-thyronine (T3), insulin, rosiglitazone, 3-isobutyl-1-methylxanthine (IBMX), dexamethasone, niacin, pioglitazone, rosiglitazone, lobeglitazone, ciglitazone, darglitazone, englitazone, netoglitazone, rivoglitazone, troglitazone, indomethacin, norepinephrine, a beta3-adrenergic receptor agonist (such as CL-316,243), or a broad beta-adrenergic agonist (such as isoproterenol). Non-limiting examples of beta3-adrenergic receptor agonist include amibegron (SR-58611A), CL-316,243, L-742,791, L-796,568, LY-368,842, Mirabegron (YM-178), Ro40-2148, Solabegron (GW-427,353), and Vibegron (MK-4618). See, e.g., Consoli et al. (2007) *European Journal of Pharmacology.* 573 (1-3): 139-47; Overstreet et al. (2008) *Pharmacology Biochemistry and Behavior.* 89 (4): 623-6; Fu et al. (2008) *European Journal of Pharmacology.* 584 (1): 202-6; Candelore et al. (1999) The Journal of Pharmacology and Experimental Therapeutics. 290 (2): 649-55; Larsen et al. (2002) *The American Journal of Clinical Nutrition.* 76 (4): 780-8; Gras (2012) *Drugs of today* (Barcelona, Spain: 1998). 48 (1): 25-32; Hicks et al. (2007) *The Journal of Pharmacology and Experimental Therapeutics.* 323 (1): 202-9; Edmondson et al. (2016) *Journal of Medicinal Chemistry.* 59 (2): 609-23, the entire content of each of which is incorporated herein by reference.

In embodiments, the adipogenic differentiation compound comprises 3,3',5-Triiodo-L-thyronine (T3), insulin, rosiglitazone, 3-isobutyl-1-methylxanthine (IBMX), or dexamethasone.

In embodiments, the adipogenic differentiation compound comprises a compound that induces or increases adipogenesis.

In embodiments, cells of the preadipocyte population express Platelet Derived Growth Factor Receptor Alpha (PDGFRα) and/or MSCA1. In embodiments, cells of the preadipocyte population express more PDGFRα and MSCA1 than the MSC population. In embodiments, a subset of preadipocytes may initially express more surface protein (e.g., as detected by flow cytometry), but will have at least higher transcription of these two markers (e.g., as detected by qPCR). In embodiments, the cell population as a whole has higher levels of these markers than the MSCs.

In embodiments, cells of the preadipocyte population have an increased level of nuclear Early B-Cell Factor 2 (EBF2) expression compared to the MSC population.

In embodiments, the beige adipocyte population comprises beige adipocytes that are thermogenically active.

In embodiments, the beige adipocyte population has increased metabolic activity compared to the MSC population.

In embodiments, the level of ATP-linked respiration in the beige adipocyte population increases by at least 10, 20, 30, 40, 50, 60, 70, 80, 90, 100, 125, 150, 175, or 200% compared to the level of ATP-linked respiration in the MSC population. In embodiments, the level of ATP-linked respiration in the beige adipocyte population increases by at least 100% compared to the level of ATP-linked respiration in the MSC population. In embodiments, the level of ATP-linked respiration in the beige adipocyte population increases by at least 125% compared to the level of ATP-linked respiration in the MSC population. In embodiments, the level of ATP-linked respiration in the beige adipocyte population increases by at least 150% compared to the level of ATP-linked respiration in the MSC population.

In embodiments, the level of uncoupled respiration in the beige adipocyte population increases by at least 50%, 100%, 200%, 300%, 400%, 500%, 600%, 700%, 800%, 900%, 1000%, 1100%, or 1200% compared to the level of uncoupled respiration in the MSC population. In embodiments, the level of uncoupled respiration in the beige adipocyte population increases by about 50% to about 1200% compared to the level of uncoupled respiration in the MSC population. In embodiments, the level of uncoupled respiration in the beige adipocyte population increases by about 50% to about 1000%, by about 50% to about 900%, by about 50% to about 800%, by about 50% to about 700%, by about 50% to about 600%, by about 50% to about 500%, by about 50% to about 400%, by about 50% to about 300%, by about 50% to about 200%, or by about 50% to about 100% compared to the level of uncoupled respiration in the MSC population. In embodiments, the level of uncoupled respiration in the beige adipocyte population increases by about 100% to about 1200% compared to the level of uncoupled respiration in the MSC population. In embodiments, the level of uncoupled respiration in the beige adipocyte population increases by about 100% to about 1000%, by about 100% to about 900%, by about 100% to about 800%, by about 100% to about 700%, by about 100% to about 600%, by about 100% to about 500%, by about 100% to about 400%, by about 100% to about 300%, or by about 100% to about 200% compared to the level of uncoupled respiration in the MSC population.

In embodiments, the level of uncoupled respiration in the beige adipocyte population increases by about 200% to about 1200% compared to the level of uncoupled respiration in the MSC population. In embodiments, the level of uncoupled respiration in the beige adipocyte population increases by about 200% to about 1000%, by about 200% to about 900%, by about 200% to about 800%, by about 200% to about 700%, by about 200% to about 600%, by 200% to about 500%, by about 200% to about 400%, or by about 200% to about 300% compared to the level of uncoupled respiration in the MSC population.

In embodiments, the level of uncoupled respiration in the beige adipocyte population increases by about 400% to about 1200% compared to the level of uncoupled respiration in the MSC population. In embodiments, the beige adipocyte population increases by about 400% to about 1000%, by about 400% to about 900%, by about 400% to about 800%, by about 400% to about 700%, by about 400% to about 600%, or by about 400% to about 500% compared to the level of uncoupled respiration in the MSC population. In embodiments, the level of uncoupled respiration in the beige adipocyte population increases by about 800% to about 1200% compared to the level of uncoupled respiration in the MSC population compared to the level of uncoupled respiration in the MSC population. In embodiments, the beige adipocyte population increases by about 800% to about 1000%, or by about 800% to about 900% compared to the level of uncoupled respiration in the MSC population.

In embodiments, the level of insulin sensitivity in the beige adipocyte population increases by at least 300% compared to the level of insulin sensitivity in the MSC population. In embodiments, the level of insulin sensitivity in the beige adipocyte population increases by about 50% to about 400% compared to the level of insulin sensitivity in the MSC population. In embodiments, the level of insulin sensitivity in the beige adipocyte population increases by about 50% to about 300%, by about 50% to about 200%, or by about 50% to about 100% compared to the level of insulin sensitivity in the MSC population. In embodiments, the level of insulin sensitivity in the beige adipocyte population increases by about 100% to about 400% compared to the level of insulin sensitivity in the MSC population. In embodiments, the level of insulin sensitivity in the beige adipocyte population increases by about 100% to about 300%, or by about 100% to about 200%, compared to the level of insulin sensitivity in the MSC population. In embodiments, the level of insulin sensitivity in the beige adipocyte population increases by about 200% to about 400% compared to the level of insulin sensitivity in the MSC population. In embodiments, the level of insulin sensitivity in the beige adipocyte population increases by about 200% to about 300% compared to the level of insulin sensitivity in the MSC population.

In embodiments, cells of the beige adipocyte population express uncoupling protein 1 (UCP1). In embodiments, cells of the beige adipocyte population express more UCP1 than the MSC population. In embodiments, UCP1 cannot be detected in the MSCs by Western blot, immunostaining, or qPCR.

In embodiments, the amount of the TGF-β inhibitor in combination with the amount of IL-4 is effective to synergistically increase UCP1 expression in cells of the beige adipocyte population.

In embodiments, cells of the beige adipocyte population express a molecular profile that is consistent with naturally occurring brown adipocytes or naturally occurring beige adipocytes. In embodiments, the molecular profile includes the expression of at least about 1, 2, 3, 4, 5, 6, 7, 8, 9, 10, 25, 50, 100, 500, 1000, or 10,000 proteins that are expressed by naturally occurring brown adipocytes or naturally occurring beige adipocytes.

In embodiments, cells of the beige adipocyte population express any one of, or any combination of 2, 3, 4, 5, 6, 7, or 8 of, or all of Cytochrome c Oxidase Subunit IV (COX-IV), protein perilipin (PLIN), Transmembrane Protein 26 (TMEM26), Cbp/P300 Interacting Transactivator With Glu/Asp Rich Carboxy-Terminal Domain 1 (CITED1), TNF Receptor Superfamily Member 9 (CD137), Peroxisome Proliferator Activated Receptor Gamma (PPARG), PR Domain Containing 16 (PRDM16), EBF2, CCAAT/Enhancer Binding Protein Alpha (CEBPA), and/or CCAAT/Enhancer Binding Protein Beta (CEBPB).

In embodiments, the level of Zic Family Member 1 (ZIC1) expression in the beige adipocyte population does not increase compared to the level of ZIC1 expression in the MSC population. In embodiments, ZIC1 expression increases or decreases slightly (e.g., less than about 15%, 10%, or 5%) compared to the level of ZIC1 expression in the MSC population. In embodiments, ZIC1 expression does not change compared to the level of ZIC1 expression in the MSC population. In classical mature brown adipocytes ZIC1 is expressed much higher than in the beige or white adipocytes.

In embodiments, cells of the beige adipocyte population have a multilocular lipid droplet morphology.

In embodiments, cells of the beige adipocyte population secrete an anti-diabetic factor.

In embodiments, the anti-diabetic factor is fibroblast growth factor 21 (FGF21), neuregulin 4 (NRG4), interleukin 6 (IL6), Adiponectin, C1Q and Collagen Domain Containing protein (ADIPOQ) or any combination thereof.

In embodiments, the MSC population is a perivascular-like MSC population.

In embodiments, the MSC population is derived from a subject who is overweight, obese, or has type II diabetes.

In embodiments, the MSC population is derived from a subject who is not overweight or obese, and who does not have type II diabetes.

In embodiments, the MSC population is derived from a subject who does not have a disease.

In embodiments, the MSC population is derived from a pluripotent stem cell (PSC) population that is produced from a cell population obtained from the subject.

In embodiments, the MSC population is derived from a lateral plate mesoderm cell population, wherein the lateral plate mesoderm cell population is produced from a PSC population, and wherein the PSC population is produced from a cell population obtained from the subject.

In embodiments, the lateral plate mesoderm is a splanchnic mesoderm cell population.

In embodiments, the lateral plate mesoderm is a somatic mesoderm cell population.

In embodiments, cells of the PSC population express Epithelial Cell Adhesion Molecule (EPCAM).

In embodiments, the PSC population is an induced pluripotent stem (iPS) cell population.

In embodiments, the iPS cell population is a Tra-1-60+ iPS cell population.

In embodiments, the integration-free StemRNA-NM-™_Reprogramming kit (Reprocell, Stemgent—Catalog No: 00-0076) is used. In embodiments, the CytoTune-iPS 2.0 Sendai Reprogramming Kit is used (CytoTune™-iPS 2.0 Sendai Reprogramming Kit, Invitrogen™ Catalog No. A16517). In embodiments, these kits use some overlapping and distinct transcription factors. In embodiments, a kit or method that produces Tra-1-60+ iPSCs is used. In embodiments, the kit or method used for reprogramming cells into iPS cells produces Tra-1-60+ iPSCs.

In embodiments, the SC population is an embryonic stem cell population.

In embodiments, the lateral plate mesoderm cell population comprises a confluent monolayer of lateral plate mesoderm cells.

During development, Forkhead box protein F1 (FOXF1) is initially expressed in the broader lateral plate mesoderm tissue, which later divides into the splanchnic and somatic mesoderm. In embodiments, cells of the lateral plate mesoderm cell population express FOXF1. In embodiments, any mesoderm that is FOXF1+ may be used to produce the MSC population. In embodiments, the FOXF1+ mesoderm is other than splanchnic or lateral plate mesoderm.

In embodiments, cells of the lateral plate mesoderm cell population express any one of, any combination of 2, 3, 4, 5, or 6 of, or all of Brachury, Mix Paired-Like Homeobox (MIXL1), Neural Cell Adhesion Molecule (NCAM), Vascular Endothelial Growth Factor Receptor 2 (VEGFR2), Odd-Skipped Related Transciption Factor 1 (OSR1), Homeobox B6 (HOXB6), Bagpipe Homeobox Protein Homolog 1 (BAPX1), and/or Homeobox protein Hox-A11 (HOX11). In embodiments, cells of the lateral plate mesoderm cell population express MIXL1, NCAM, VEGFR2, OSR1, HOXB6, BAPX1, and/or HOX11 at a level that is greater than in iPS cells or embryonic stem cells.

In embodiments, cells of the lateral plate mesoderm cell population express each of SRY-Box 1 (SOX1), SRY-Box 17 (SOX17), Iroquois Homeobox 3 (IRX3), and PDGFRα at a level that is less than in ectoderm, endoderm, paraxial mesoderm or somatic mesoderm.

In embodiments, cells of the lateral plate mesoderm cell population do not express SOX1, SOX17, IRX3, or PDGFRα.

In embodiments, cells of the lateral plate mesoderm cell population express NCAM. In embodiments, cells of the lateral plate mesoderm cell population express NCAM at a level that is greater than in iPS cells or embryonic stem cells. In embodiments, cells of the lateral plate mesoderm cell population express EPCAM. In embodiments, cells of the lateral plate mesoderm cell population express EPCAM at a level that is greater than in iPS cells or embryonic stem cells.

In embodiments, cells of the MSC population comprise perivascular-like FOXF1-derived MSCs.

In embodiments, cells of the MSC population express any one of, or any combination of 2, 3, 4, 5, 6, 7, 8, or 9 of, or all of Endoglin (CD105), 5'-Nucleotidase Ecto (CD73), Thy-1 Cell Surface Antigen (CD90), Melanoma Cell Adhesion Molecule (CD146), Platelet Derived Growth Factor Receptor Beta (PDGFRβ), Chondroitin Sulfate Proteoglycan 4 (NG2), α-smooth muscle actin (α-SMA), TGFβ Receptor 1 (TGFβR1), TGFβ Receptor 2 (TGFβR2), and/or smooth muscle protein 22-α (SM22).

In embodiments, at least 95% of the cells of the MSC population express CD105, CD73, CD90, CD146, PDGFRβ, NG2, α-SMA, TGFβR1, TGFβR2, and/or SM22.

In embodiments, at least 90% of the cells of the MSC population express CD105, CD73, CD90, CD146, PDGFRβ, NG2, α-SMA, TGFβR1, TGFβR2, and/or SM22.

In embodiments, at least 80% of the cells of the MSC population express CD105, CD73, CD90, CD146, PDGFRβ, NG2, α-SMA, TGFβR1, TGFβR2, and/or SM22.

In embodiments, at least 70% of the cells of the MSC population express CD105, CD73, CD90, CD146, PDGFRβ, NG2, α-SMA, TGFβR1, TGFβR2, and/or SM22.

In embodiments, at least 60% of the cells of the MSC population express CD105, CD73, CD90, CD146, PDGFRβ, NG2, α-SMA, TGFβR1, TGFβR2, and/or SM22.

In embodiments, at least 50% of the cells of the MSC population express CD105, CD73, CD90, CD146, PDGFRβ, NG2, α-SMA, TGFβR1, TGFβR2, and/or SM22.

In embodiments, at least 40% of the cells of the MSC population express CD105, CD73, CD90, CD146, PDGFRβ, NG2, α-SMA, TGFβR1, TGFβR2, and/or SM22.

In embodiments, the cell population is obtained from the subject via a biopsy.

In embodiments, the cell population obtained from the subject comprises a subcutaneous adipogenic precursor cell population.

In embodiments, the cell population obtained from the subject comprises an adipocyte population.

In embodiments, the cell population obtained from the subject is other than an adipocyte population.

In embodiments, the cell population obtained from the subject is a dermal cell population.

In embodiments, the cell population obtained from the subject is a cell type from which an iPS cell population can be generated.

Included herein are methods of producing a beige adipocyte population comprising (a) obtaining a cell population from a subject; (b) producing a PSC population from the cell population; (c) producing a splanchnic mesoderm cell population from the PSC population; (d) producing an MSC population from the splanchnic mesoderm cell population; and (e) producing the beige adipocyte population from the MSC population.

In embodiments, producing the beige adipocyte population from the MSC population comprises contacting the MSC population with an effective amount of (i) IL-4; and/or (ii) a TGF-β inhibitor.

In embodiments, producing the beige adipocyte population from the MSC population comprises contacting the MSC population with an effective amount of interleukin 4 (IL-4).

In embodiments, producing the beige adipocyte population from the MSC population comprises contacting the MSC population with an effective amount of a TGF-β inhibitor Also provided are beige adipocytes (e.g., populations of beige adipocytes) produced according to the methods disclosed herein.

Methods for Treating Metabolic Disorders and Inducing Weight Loss

Included herein is a method of preventing or treating obesity in a subject in need thereof. In embodiments, the method comprises administering to the subject an effective amount of a population of beige adipocytes produced by a method herein, and/or a factor (such as an anti-diabetic factor) obtained from a population of beige adipocytes produced by a method herein.

In an aspect, a method of preventing or treating obesity in a subject in need thereof is provided. The method comprises administering to the subject an effective amount of IL-4 and a TGF-β inhibitor.

In an aspect, provided herein is a method of increasing the level of a beige adipocyte population in a subject in need thereof. The method comprises administering to the subject an effective amount of IL-4 and a TGF-β inhibitor.

In embodiments, the IL-4 and the TGF-β inhibitor is administered to (e.g., injected into) adipose tissue of the subject.

In aspects, a method of reducing the weight or body mass index of an overweight subject is provided herein. The method comprises administering to the subject a population of beige adipocytes produced according to a method herein.

Kits for Producing Beige Adipocytes

In aspects, a kit for producing a beige adipocyte is provided. In embodiments, the kit comprises (i) cell culture media or a cell culture medium; (ii) IL-4; and (iii) a TGF-β inhibitor.

Various alternative reagents (e.g., coatings, disassociation agents, stimulation reagents, differentiation reagents, and culture reagents such as media) may be used in embodiments herein. No specific set of reagents is required for the culturing of, e.g., mesoderm cells, MSCs, ES cells, and iPSCs. However, non-limiting examples are provided below.

In embodiments, the kit comprises a medium for growth and expansion of human iPS and hES cells. In embodiments, the medium is NutriStem® hPSC XF Medium (StemGent Catalog No. 01-0005).

In embodiments, the kit comprises a reagent for ES and/or iPS cell selection and/or passaging. In embodiments, the reagent is ReLeSR™ passaging reagent (Stemcell Technologies, Vancouver Canada, Catalog No. 05872 or 05873). In embodiments, the reagent is mTeSR™ 1 (Stemcell Technologies, Vancouver Canada, Catalog No. 85850 or 85857). In embodiments, the reagent is Vitronectin XF™ (Stemcell Technologies, Vancouver Canada, Catalog No. 07180 or 07190). In embodiments, the reagent is Gentle Cell Dissociation Reagent (Stemcell Technologies, Vancouver Canada, Catalog No. 07174). Many plate coating reagents and ES/iPSC medium are commercially available and will be known to those skilled in the art. In embodiments, any plate coating reagent may be used. In embodiments, the coating reagent is Matrigel from Corning (New York N.Y., USA).

In embodiments, iPSC brew XF from Miltenyi is used for cell growth (Cambridge Mass., USA).

In embodiments, the kit comprises a reagent comprising one or more cell-dissociation enzymes. In embodiments, the reagent is TrypLE™ cell dissociation reagent (ThermoFisher Catalog No: A1285901). In embodiments, the reagent is TrypLE™ Express (Thermo Fisher SKU No. 12604-013). In embodiments, the reagent is StemPro™ Accutase™ Cell Dissociation Reagent (Thermo Fisher Catalog No. A1110501). Various disassociation reagents are known in the art and may be used. In embodiments, cells may be physically scraped off a culture surface (such as a plate).

In embodiments, the kit comprises a medium for early mesodermal differentiation. In embodiments, the medium is STEMdiff™ Mesoderm Induction Medium (Stemcell Technologies, Vancouver Canada, Catalog No. 05220 or 05221). In embodiments, the medium is MesenCult™-ACF Culture Kit (Stemcell Technologies, Vancouver Canada, Catalog No. 05449). In embodiments, the medium is Vitronectin XF™ (Stemcell Technologies Catalog No. 07180). In embodiments, Matrigel from Corning is used for ES cell/iPSC growth and mesoderm induction. In embodiments, ACF attachment substrate is used when the cells are in Mesencult ACF medium.

In embodiments, the kit comprises a dissociation kit for human stem and progenitor cells. In embodiments, the kit comprises ACF Enzymatic Dissociation Solution (Stemcell Technologies, Vancouver Canada, Catalog No. 05426). In embodiments, the kit comprises Collagenase A Animal Component-Free (ACF) (Stemcell Technologies, Vancouver Canada Catalog No: 07434).

In embodiments, the kit comprises the BulletKit. In embodiments, the BulletKit includes hEGF, Hydrocortisone, GA-1000 (Gentamicin, Amphotericin-B), FBS (Fetal Bovine Serum), VEGF, hFGF-B, R3-IGF-1, Ascorbic Acid, and Heparin.

In embodiments, one or more components of the BulletKit is added to EGM2. In embodiments, the FGF2 is omitted. In embodiments, the FBS concentration is used at a concentration from about 2% to about 0.5%. In embodiments, the FBS concentration is less than about 2%. In embodiments, the FBS concentration is about 0.5%. In embodiments, Dulbecco Modified Eagle Medium (DMEM) with 2% FBS is used. In embodiments, EGM2 medium is not used.

In embodiments, the kit comprises EGM-2 medium. In embodiments, the kit comprises DMEM medium.

In embodiments, the kit comprises an adipogenic differentiation compound. In embodiments, the adipogenic differentiation compound comprises 3,3',5-Triiodo-L-thyronine (T3), insulin, rosiglitazone, 3-isobutyl-1-methylxanthine (IBMX), dexamethasone, or indomethacin.

In embodiments, a cell culture medium in the kit is suitable for culturing an MSC population.

In embodiments, a cell culture medium in the kit comprises about 5%, 4.5%, 4%, 3.5%, 3%, 2.5%, 2%, 1.5%, 1%, or 0.5% serum. In embodiments, the kit is configured for use of about 5%, 4.5%, 4%, 3.5%, 3%, 2.5%, 2%, 1.5%, 1%, or 0.5% serum or less.

In embodiments, a cell culture medium in the kit comprises less than 5%, 4%, 3%, or 2% serum.

In embodiments, a cell culture medium in the kit is a serum-free cell culture medium.

In embodiments, the kit does not comprise serum.

In embodiments, the cell culture media in the kit comprises a first cell culture medium and a second cell culture medium, wherein the first cell culture medium is suitable for culturing or inducing a PSC population and the second cell culture medium is suitable for culturing or inducing a mesoderm cell population.

In embodiments, the cell culture media of the kit further comprises a third cell culture medium, wherein the third cell culture medium is suitable for culturing or inducing an MSC population.

In embodiments, the third cell culture medium of the kit is an adipogenic medium.

In embodiments, the first cell culture medium of the kit induces a PSC population to produce a lateral plate mesoderm cell population.

In embodiments, the second cell culture medium of the kit induces a lateral plate mesoderm cell population to produce an MSC population.

In embodiments, the third cell culture medium induces an MSC population to produce an adipocyte population.

EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Compared to other methods, an illustrative non-limiting method in the Example that follows uses three commercially available mediums to generate beige adipocytes, which are largely serum/xeno free, which resulted in more consistent results. These beige adipocytes were functionally similar to brown adipocytes, but are developmentally distinct. In embodiments, serum characteristics can change from lot to lot, and mediums that are highly quality controlled are preferably used.

Example 1: A Renewable Source of Human Beige Adipocytes for Metabolic Disorders

Generation of FOXF1+ Splanchnic Mesoderm from Human ES/iPS Cells

In this work, a multi-stage culture system was defined for the generation of human beige adipocytes from PSCs. This can be accomplished largely under defined serum-free medium conditions using commercially available medium, which may reduce the lack of reproducibility that has hampered the widespread use of PSC technology to study adipogenesis. Importantly, rather than short-circuiting mesoderm directly into mature beige/brown adipocytes as other methods have shown[21, 22], these cells are generated through a developmental progression including highly expandable perivascular-like mesenchymal stem cells (MSCs), which increases their utility and provides a more accurate study of beige development as it occurs naturally in mammals.

Commercial mesoderm induction medium (MIM) was used to generate mesoderm from human PSCs over 5 days of monolayer cell culture. The resulting mesoderm expresses high levels of the canonical mesodermal transcripts Brachury and MIXL1, and limited to no expression of the ectoderm marker SOX1 or the endoderm marker SOX17 (FIG. 1A). The initial cell density of the PSCs was important as it had a significant impact on the expression of Brachury and MIXL1 (FIG. 1A).

Figure 1B:
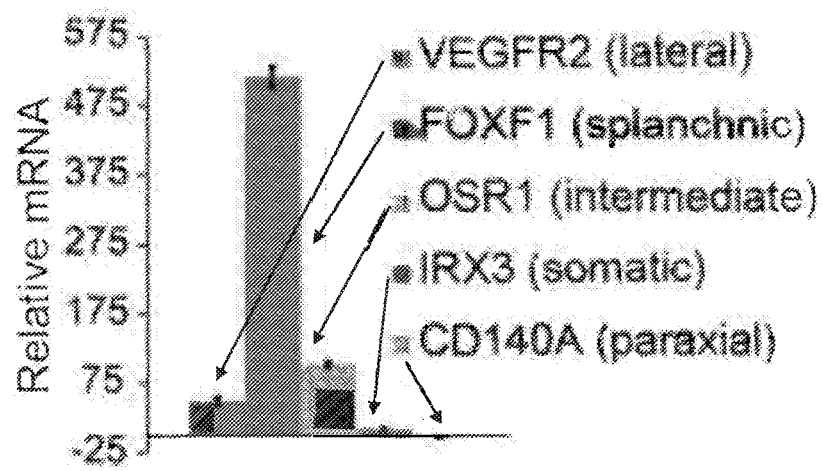
Figure 1C:
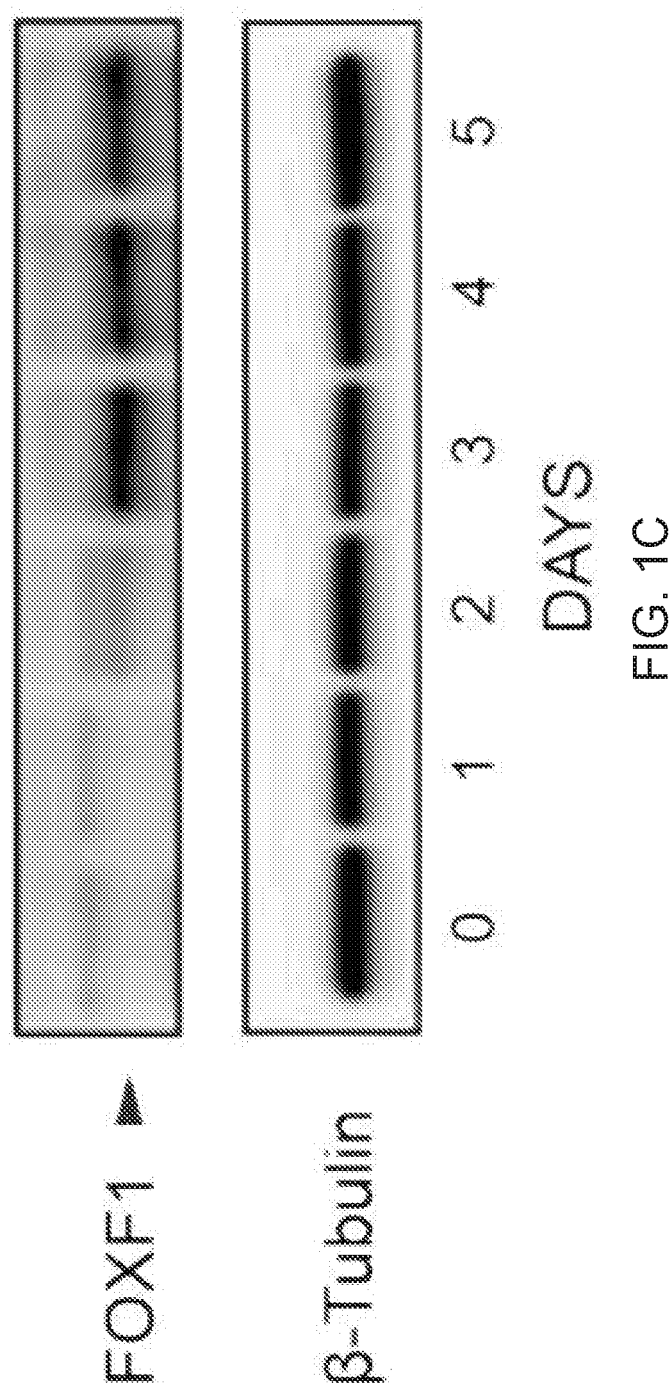
Figure 1D:
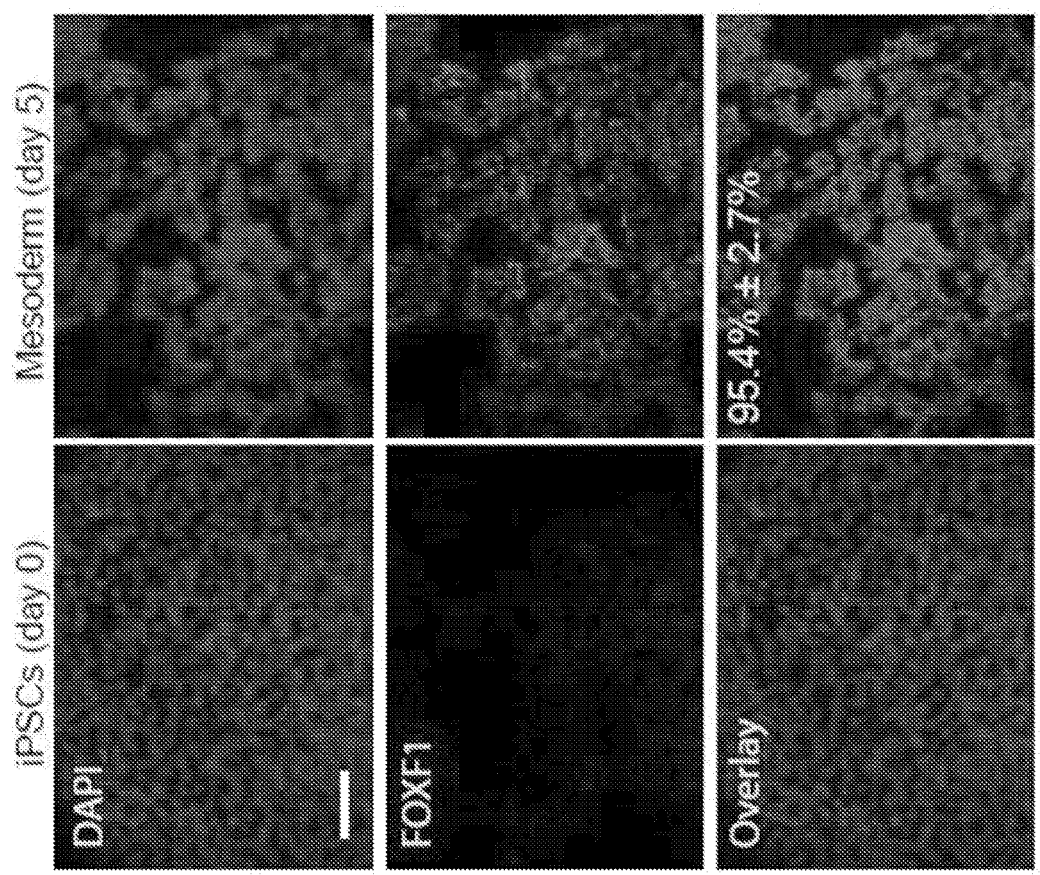

By day 5, mesoderm was characterized by reciprocal changes in surface expression of EPCAM (PSCs) and NCAM (mesoderm), demonstrating that an epithelial-to-mesenchymal transition (EMT) indicative of mesoderm commitment had occurred in the majority of cells (FIG. 1B)[23]. Analysis of differentiating cultures (day 5) for transcripts expressed in specific mesoderm layers indicated high expression of lateral plate mesoderm markers VEGFR2+24 and OSR1+25, and low to absent expression of somatic (IRX3) and paraxial (PDGFRα) mesoderm markers, respectively (FIG. 1B). Highest expression was observed for the mesoderm-specific transcript FOXF1, which is specific to the splanchnic layer that develops within the lateral plate mesoderm and gives rise to numerous tissues including, including perivascular and smooth muscle cells[26]. Other markers useful for development of splanchnic mesoderm also showed increased expression by day 5 compared to day 0 PSCs, including HOXB6, BAPX1 and HOX11[27-29]. FOXF1 protein increased substantially after 2 days of culture in MIM and remained expressed throughout day 5, as indicated by western blot (FIG. 1D). In addition, day 5 mesoderm was homogeneously positive (>95% positive) for FOXF1 protein as determined by immunostaining, indicating that MIM may be specific for generating splanchnic mesoderm (FIG. 1D)[26].

Figure 8A:
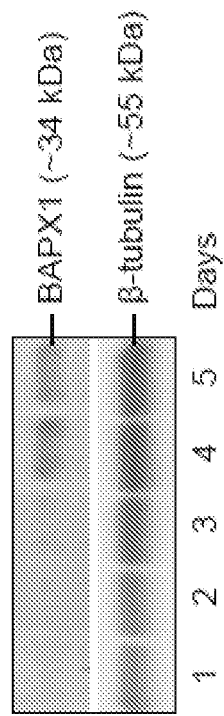
FIGS. 8A-8G show the generation of splanchnic mesoderm using commercial and in house medium.
Figure 8B:
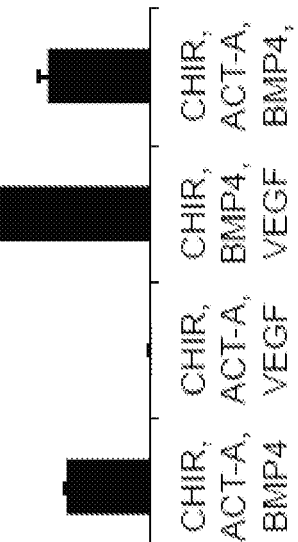
Figure 8C:
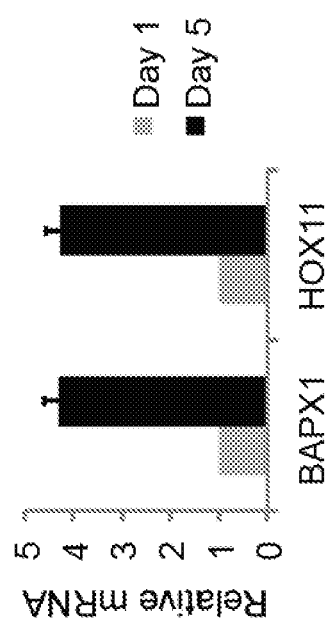
Figure 8C:
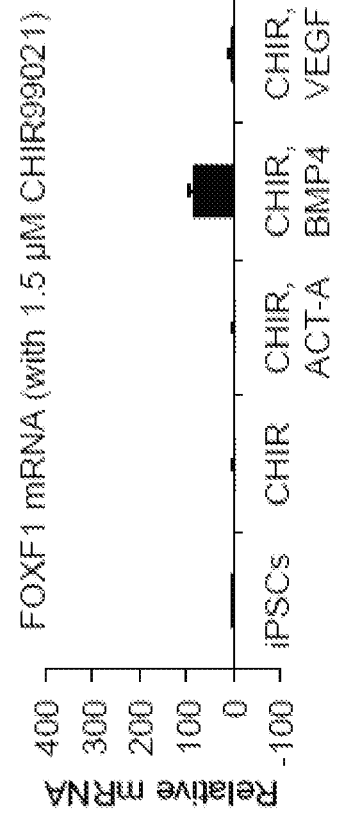
Figure 8D:
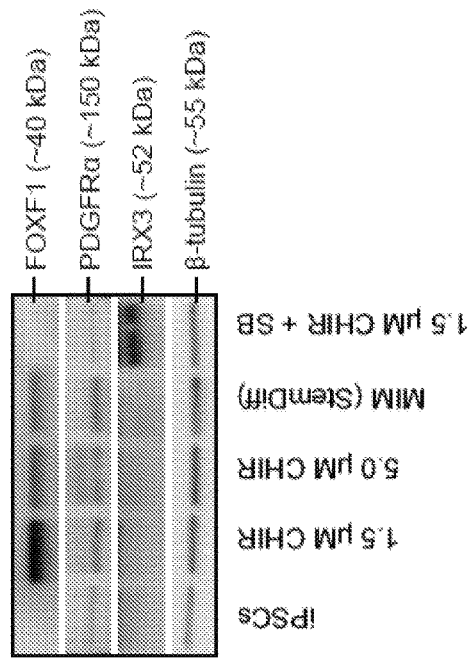
Figure 8E:
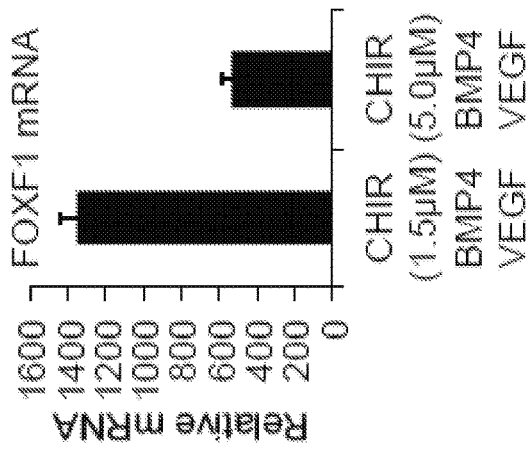
Figure 8F:
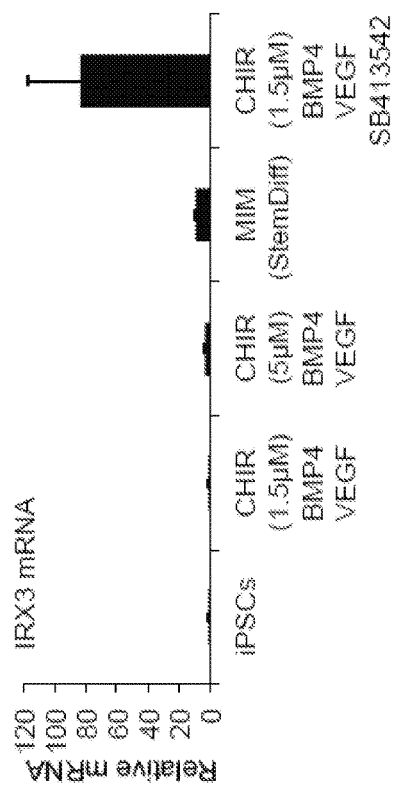
Figure 8G:
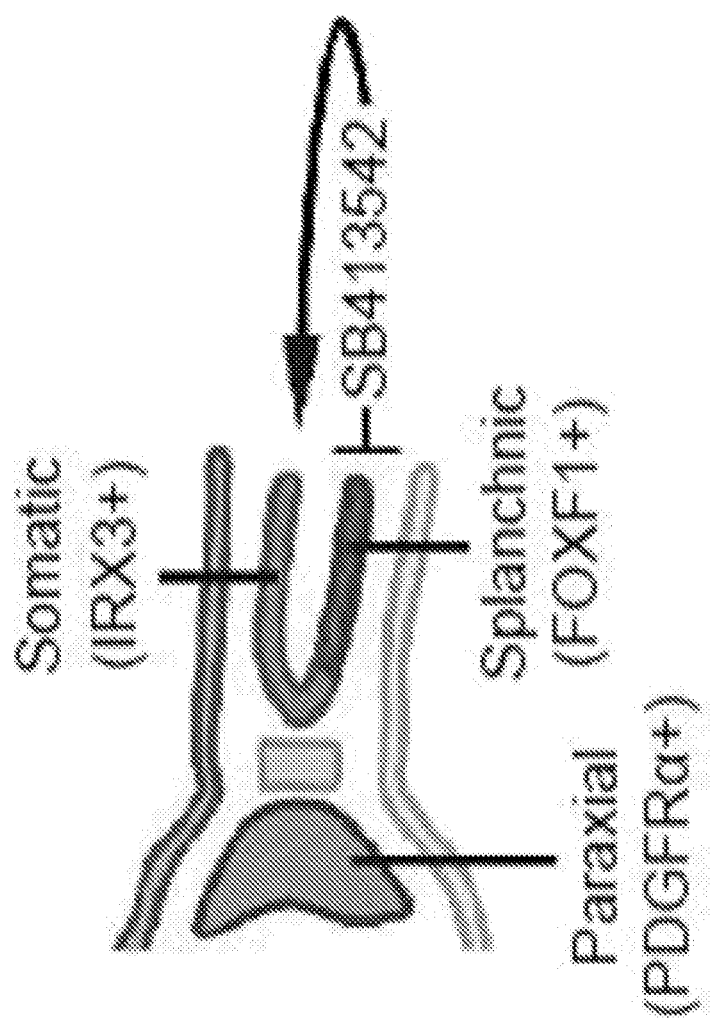

Other markers useful for the development of splanchnic mesoderm also showed increased expression by day 5 compared to day 0 iPSCs, including BAPX1 and HOX11 (Roberts et al., 1995; Tribioli et al., 1997) (FIGS. 8A and 8B). Using a combinatorial screening approach with a number of growth factors and small molecule pathway inhibitors, an in-house version of MIM was generated by supplementing STEMdiff APEL-2 iPSC differentiation medium with the WNT agonist CHIR99021 (CAS [252917-06-9]) and recombinant BMP4 and VEGFA proteins (FIG. 8C-8F)). This medium was highly specific for the generation of FOXF1+ splanchnic mesoderm. Further addition of the transforming growth factor beta (TGF-β) inhibitor SB431542 (SB) resulted in a switch from the splanchnic to the somatic mesoderm, resulting in a loss of FOXF1 expression and increased expression of IRX3 (FIG. 8E-8G). Overall, these results demonstrated the differentiation of iPSCs toward cells with a molecular profile that resembled the splanchnic mesoderm.

Furthermore, these results demonstrated that MIM had the potential to drive PSC differentiation towards tissues that develop downstream of splanchnic mesoderm, including perivascular cells thought to be precursors to beige adipocytes.

Generation of Perivascular-Like FOXF1-Derived MSCs (FD-MSCs) (Generation of Mural-Like FOXF1-Derived MSCs)

Studies have demonstrated that either serum containing or serum replacement MSC medium can aid in the differentiation of PSC-derived mesoderm into MSCs with the potential (albeit low) to give rise to adipocytes[30]. Likewise, it was hypothesized that continuous culture and passage of FOXF1+ splanchnic mesoderm in xeno/serum-free MSC medium (MesenCult™-ACF) would generate FOXF1-derived MSCs (FD-MSCs) with a perivascular phenotype. After 3 to 6 passages (18 to 28 days) in MesenCult™-ACF, highly pure cell populations were obtained positive for the markers CD105, CD73 and CD90, a characteristic immunophenotype of human MSCs (FIG. 2A, top panels)[23].

Figure 2A:
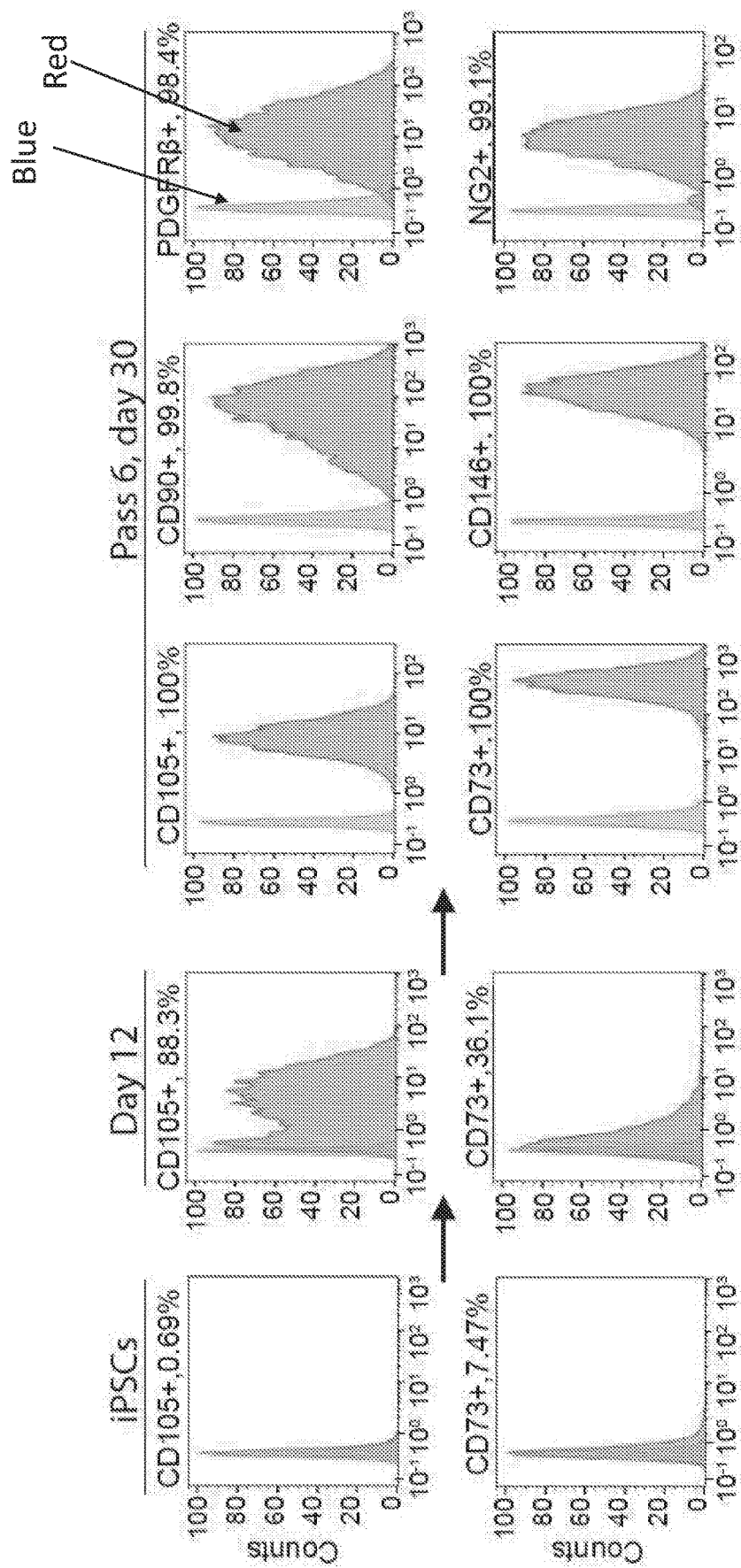
FIGS. 2A-2E depict the generation of perivascular-like FOXF1-derived MSCs (FD-MSCs).
Figure 2B:
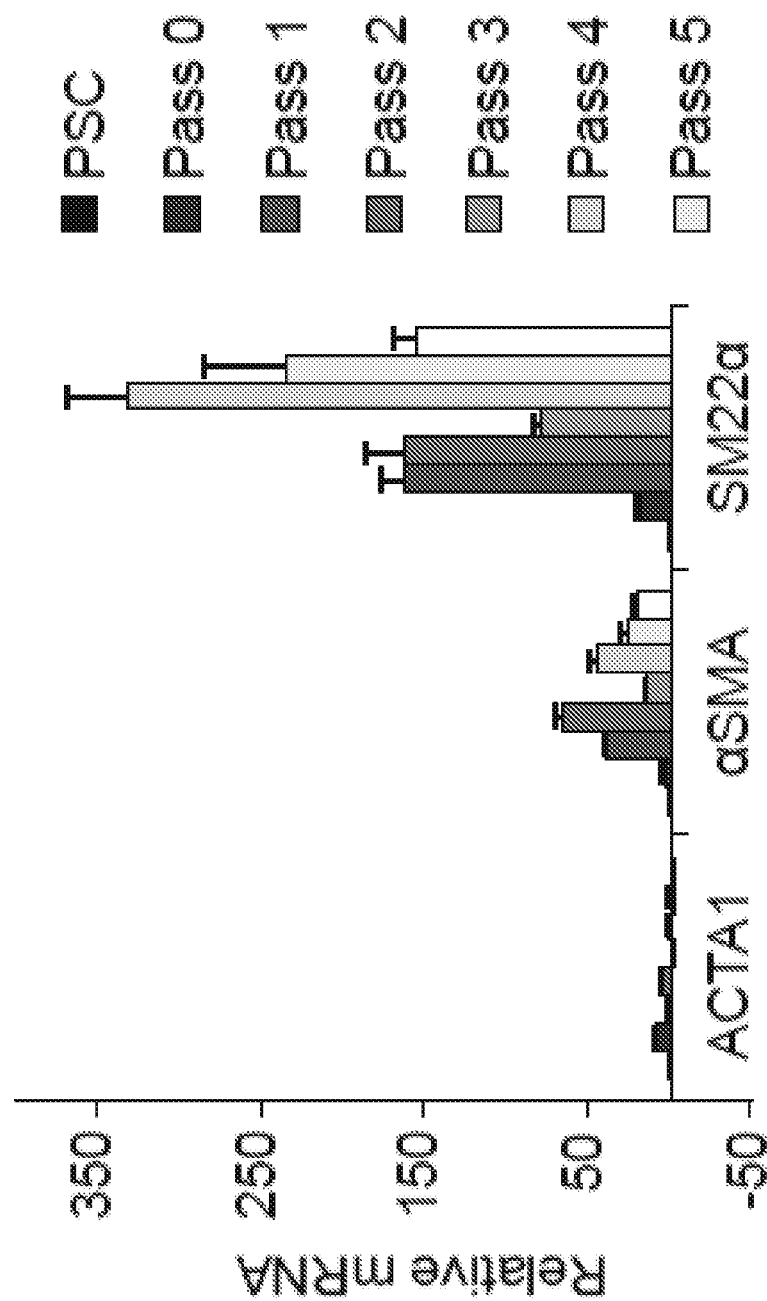
Figure 2C:
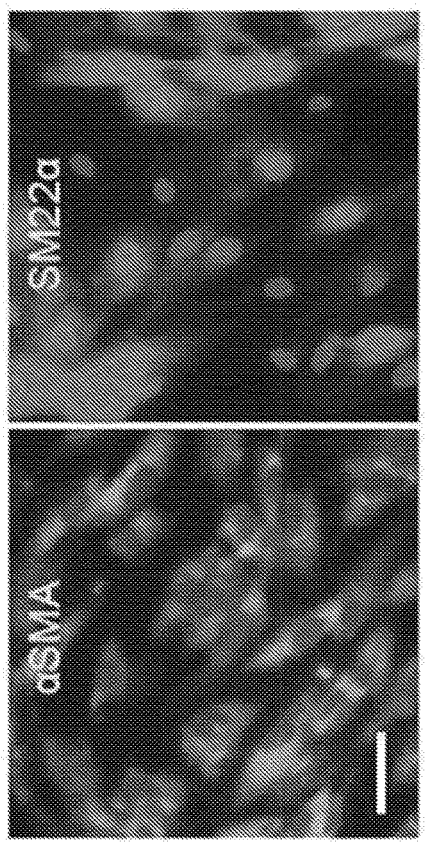
Figure 2D:
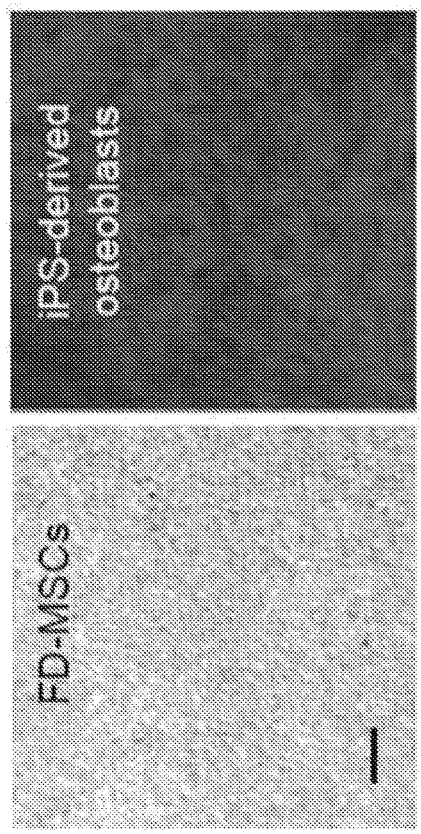
Figure 2E:
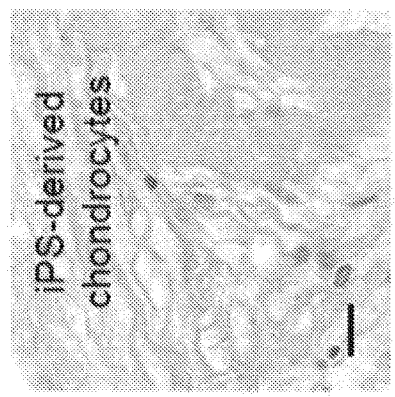
Figure 2E:
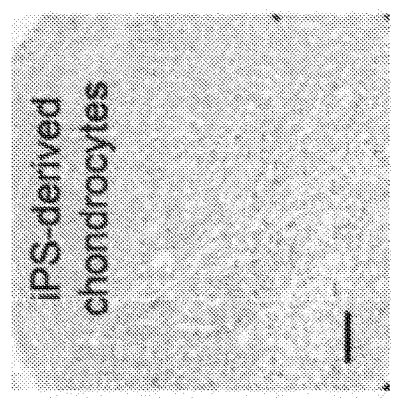

More specifically, FD-MSCs displayed additional surface marker expression consistent with mural cells, including CD146, PDGFRβ and NG231 (FIG. 2A, bottom panels). Transcript analysis over the developmental time course from PSC to MSC indicates increased expression of α-smooth muscle actin (α-SMA) and smooth muscle protein 22-α (SM22), but not actin from skeletal muscle (ACTA1), which is normally derived from paraxial mesoderm (FIG. 2B). This was in agreement with positive immunostaining of FD-MSCs for α-SMA and SMA22 (FIG. 2C). A characteristic feature of MSCs is their ability to differentiate into osteocytes, chondrocytes and adipocytes. FD-MSCs were able to differentiate into osteocytes and chondrocytes using serum/xeno-free differentiation medium (FIGS. 2D and E), demonstrating their multipotent ability, however, initial attempts to derive adipocytes were unsuccessful.

TGF-β Signaling in FD-MSCs Inhibited their Differentiation into Adipocytes

Figure 3A:
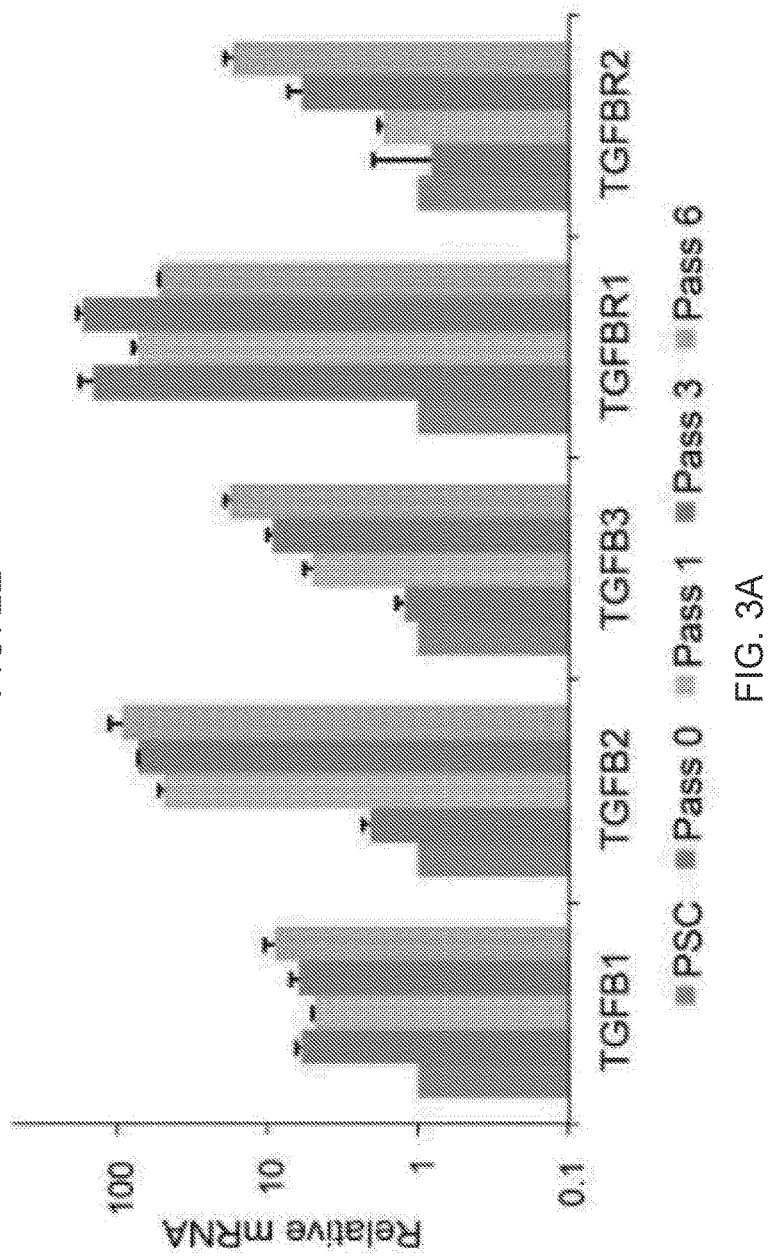

A recent study suggested that PSC-derived MSCs positive for CD73, CD105, CD90, and CD146 can give rise to white, beige and classical brown adipocytes, but showed very low adipogenic potential, which can be overcome with the TGFβ inhibitor SB431542 (SB)[32, 33]. The expression of TGFβ-ligands and receptors were monitored during the development of FD-MSCs from PSCs and were found to increase transcription for TGFβ ligands 1, 2 and 3, and the receptors TGFβR1 and 2 over multiple cell passages (FIG. 3A).

Figure 3B:
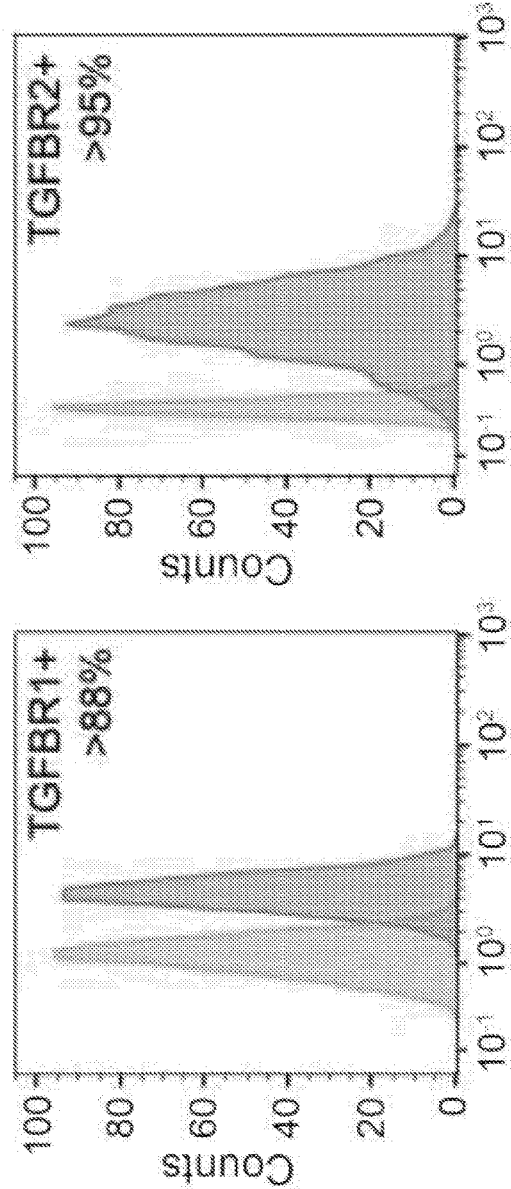
FIG. 3B depicts flow cytometry data of TGF-β receptors expressed on FD-MSCs with isotype controls. Representative plots of passage 6 FD-MSCs shown.
Figure 3C:
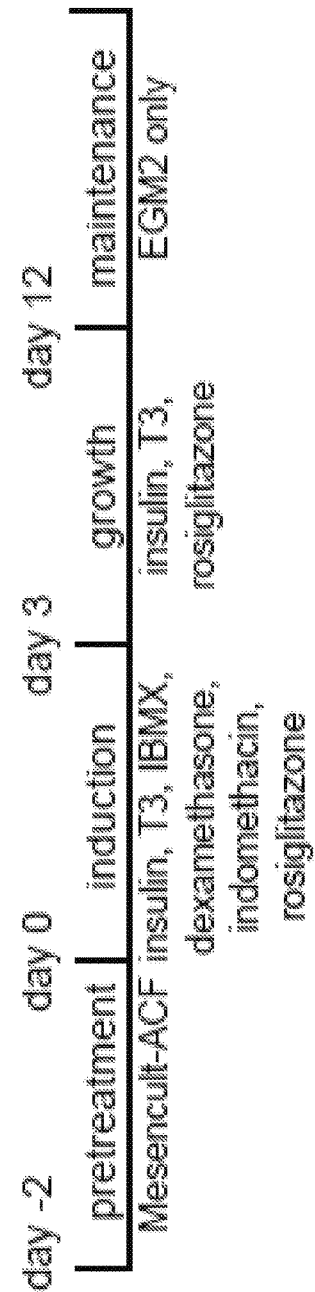
FIG. 3C depicts a schematic diagram illustrating the differentiation protocol used for adipogenic differentiation (modified form[10]).

Furthermore, FD-MSCs displayed expression of TGFI3R1 and 2 as determined by flow cytometry (FIG. 3B). Treatment of FD-MSCs in endothelial growth medium (EGM2+2% FBS) with a modified cocktail of factors for brown adipogenesis (FIG. 3C) produced only a limited amount of lipid droplet formation that is minimally discernable by day 12 of differentiation as determined by boron-dipyrromethane (BODIPY) lipid stain (FIG. 3D, upper left panel)[10]. However, additional treatment of FD-MSCs with SB throughout the adipogenic differentiation period increased lipid content by 5-fold to approximately 50% of the cells in culture (FIG. 3D, lower left panel and FIG. 3E).

Figure 3D:
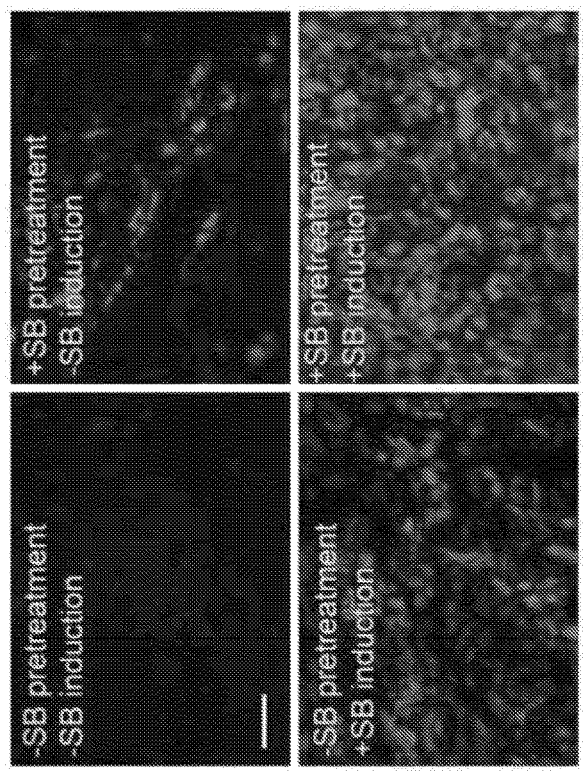
FIG. 3D depicts fluorescence microscopy images of BODIPY stained FD-MSCs differentiated for 12 days with and without SB431542 (SB) during pretreatment (2 days) or induction (12 days). Representative images shown. Scale bar=100 µm.
Figure 3E:
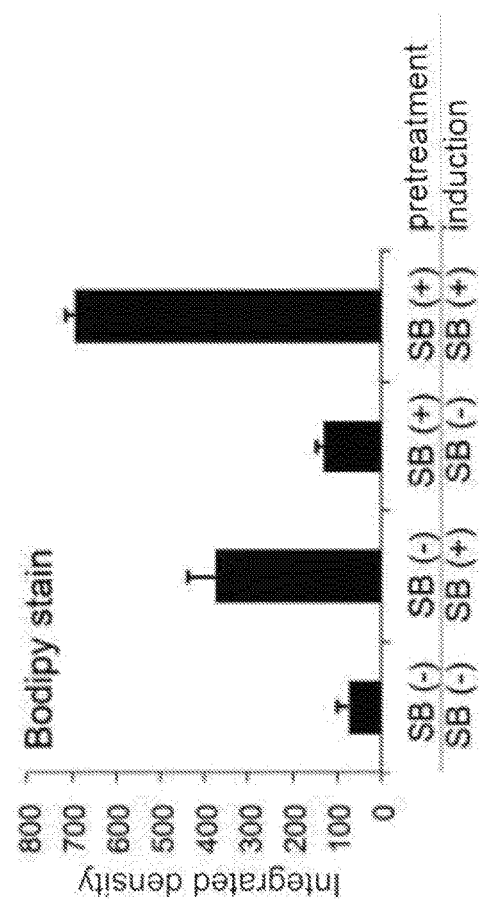
FIG. 3E depicts a graph of the lipid accumulation in differentiating FD-mSCs and without SB (quantitation of (FIG. 3D) by image J software as measured by relative integrated density expressed as mean±SD (n=4 20× images).
Figure 3G:
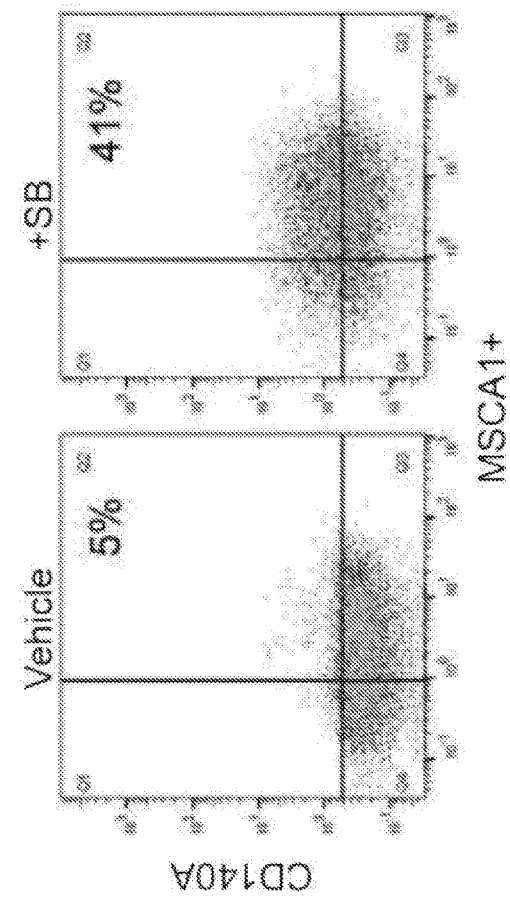
FIG. 3G depicts flow cytometry analysis of beige adipogenic precursor markers in FD-MSCs treated for 2 days with SB431542.
Figure 3I:
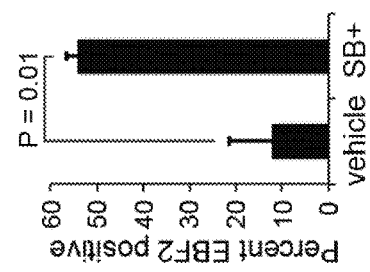
FIG. 3I is a graph showing quantitation of (FIG. 3H) expressed as mean±SD (n=4, 20× images). Student's p value shown.
Figure 3F:
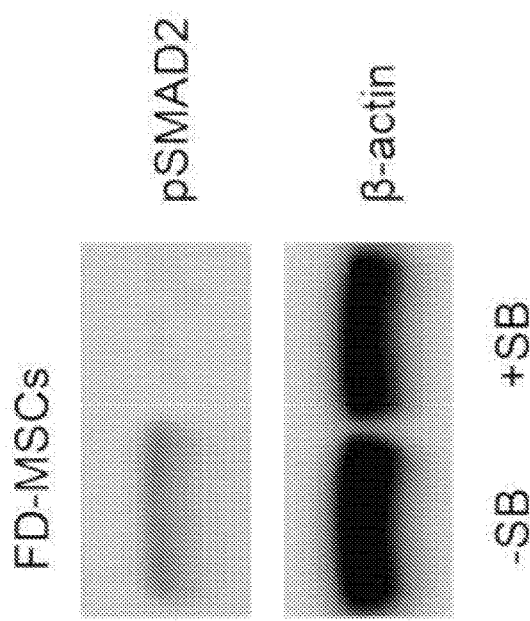
FIG. 3F depicts an image of a Western blot analysis of phosphorylated SMAD2 before and after 3 days of treatment with SB431542. β-actin protein shown as loading control.

When FD-MSCs were pretreated for 2 days in MesenCult™-ACF medium with SB prior to adipocyte differentiation, constitutive phosphorylation of SMAD2 was inhibited and cell surface expression of known beige adipogenic precursor markers PDGFRα34 and MSCA135 increased (FIG. 3F and FIG. 3G). In addition, SB pretreatment for 2 days prior to the adipogenic differentiation cocktail significantly increased nuclear accumulation of EBF2, a transcription factor present in committed PDGFRα+ preadipocytes known to give rise to beige and brown adipocytes (FIGS. 3H and 3I)[18].

Figure 3H:
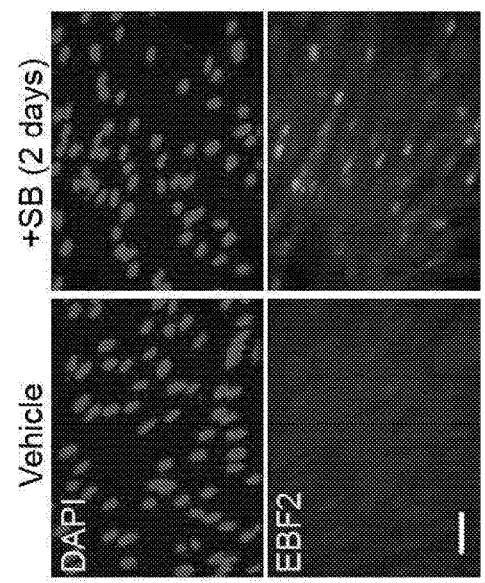
FIG. 3H depicts images of immunostaining of the beige and brown adipogenic precursor marker EBF2 (green). DAPI shown in blue.
Figure 3J:
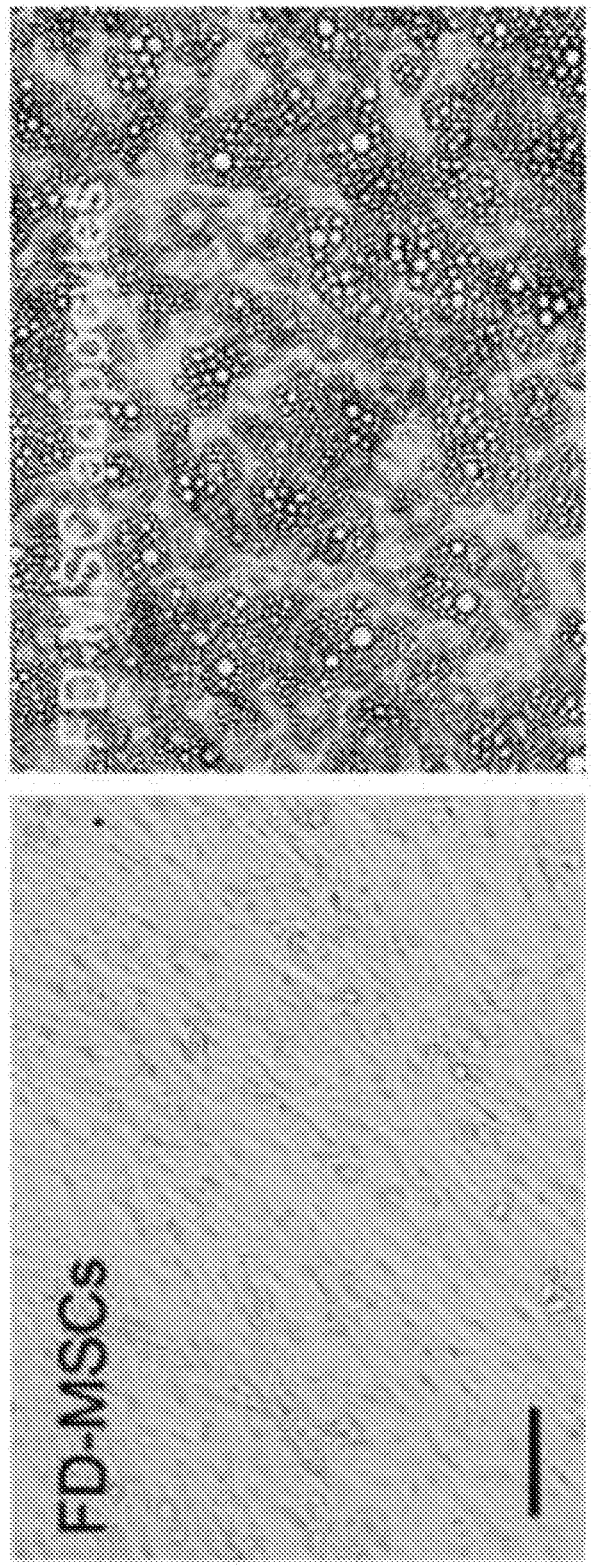
FIG. 3J are images showing phase contrast microscopy of FD-MSCs or FD-MSC derived adipocytes treated with SB431542 prior to and during adipogenic differentiation. Scale bar=50 µm.

Treatment of FD-MSCs with SB for 2 days before 12 days of differentiation led to the presence of lipid accumulation (FIG. 3D, upper right). Treatment of FDMSCs with SB throughout the 12-day adipogenic differentiation period, but not before, increased lipid content further (FIG. 3D, lower left, and quantitated in FIG. 3E). Treatment of FD-MSCs with SB for 2 days before and throughout the 12-day adipogenic differentiation period resulted in the greatest amount of lipid accumulation (FIG. 3D, lower right, and FIG. 3E). Both Perilipin (PLIN) and peroxisome proliferator-activated receptor gamma 2 (PPARg2) staining of SB-treated cultures indicated that approximately 87%-88% of the cells in culture consisted of mature adipocytes (FIGS. 3K-3M). When FD-MSCs were pretreated for 2 days in MesenCult-ACF medium with SB before adipocyte differentiation, the constitutive phosphorylation of SMAD2 was inhibited and the cell surface expression of known beige adipogenic precursor markers PDGFRa (Lee et al., 2012) and mesenchymal stem cell antigen 1 (MSCA1) (Esteve et al., 2015) increased (FIGS. 3I-3J). In addition, SB pretreatment for 2 days before the adipogenic differentiation cocktail significantly increased nuclear accumulation of early B cell factor 2 (EBF2), a transcription factor that is present in committed PDGFRa+ adipogenic precursors known to give rise to beige and brown adipocytes (FIGS. 3K and 3L; Wang and Seale, 2016).

These results indicated that inhibition of TGFβ signaling promoted the transition of FD-MSCs into beige adipogenic precursors, in addition to its role in promoting mature beige and brown adipocytes[31, 36]. When FD-MSCs were pretreated with SB prior to and during adipogenic differentiation, the amount of lipid droplet staining increased by an additional 45% over FD-MSCs treated with SB during the adipogenic differentiation protocol alone, resulting in the majority of the cells becoming adipocytes (FIG. 3D, FIG. E and FIG. 3H). These results suggested that TGFβ inhibition contributed to both adipogenic precursor commitment of FD-MSCs and their differentiation into adipocytes.

FD-MSCs Differentiated into Beige Adipocytes

PDGFRβ+, α-SMA+, NG2+ mural cells that reside within the vasculature of subcutaneous white adipose tissue have been identified as potential precursor sources of PDGFRβ+/EBF2+ preadipocytes that give rise to mature beige adipocytes[18, 37]. Thus, without being bound by any scientific theory, it was hypothesized that FD-MSCs would differentiate into adipocytes with beige cell characteristics.

A major characteristic of beige adipocytes is the expression of UCP1, a mitochondrial membrane protein that uncouples oxidative phosphorylation and increases proton leak across the inner mitochondrial membrane, resulting in increased thermogenesis and energy expenditure.

Figure 4A:
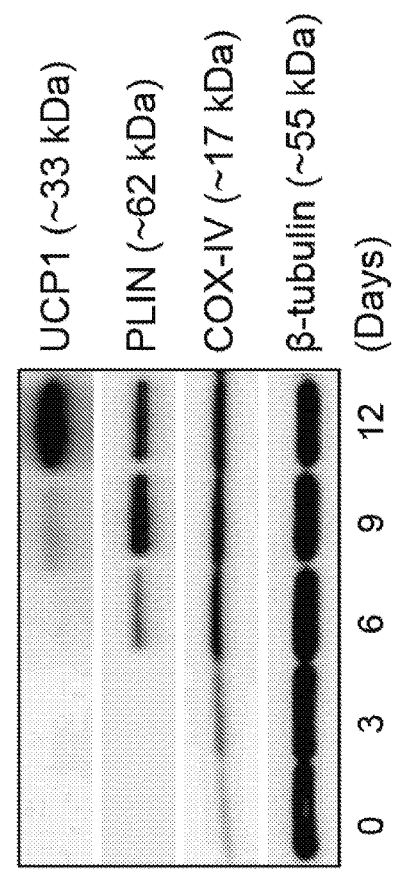
FIGS. 4A-4M show that FD-MSCs differentiate into beige adipocytes.

Indeed, qPCR analysis of UCP1 gene expression over the adipogenic time course showed a large increase in UCP1 when cells are differentiated in the presence of SB (FIG. 4A). Primary human subcutaneous white adipocytes also showed enhanced expression of UCP1 when treated with SB, suggesting that enhanced browning by TGFβ inhibition extends beyond PSC-derived cells (FIG. 8). FD-MSCs additionally pretreated with SB prior to adipogenic differentiation did not show an additional increase in UCP1 gene transcription, however, the peak of expression occurred 3 days earlier, consistent with a prior transition from FD-MSCs to adipogenic precursors during the pretreatment period.

Figure 4B:
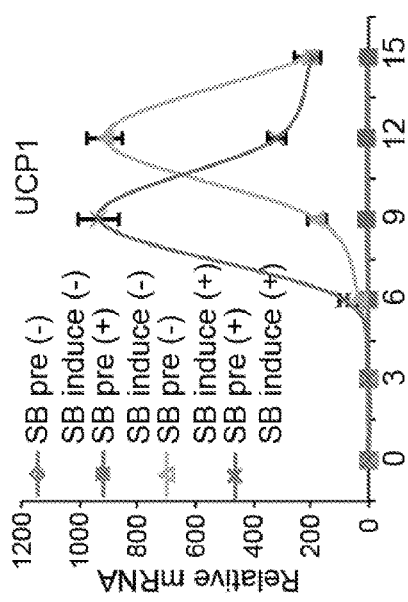
Figure 4C:
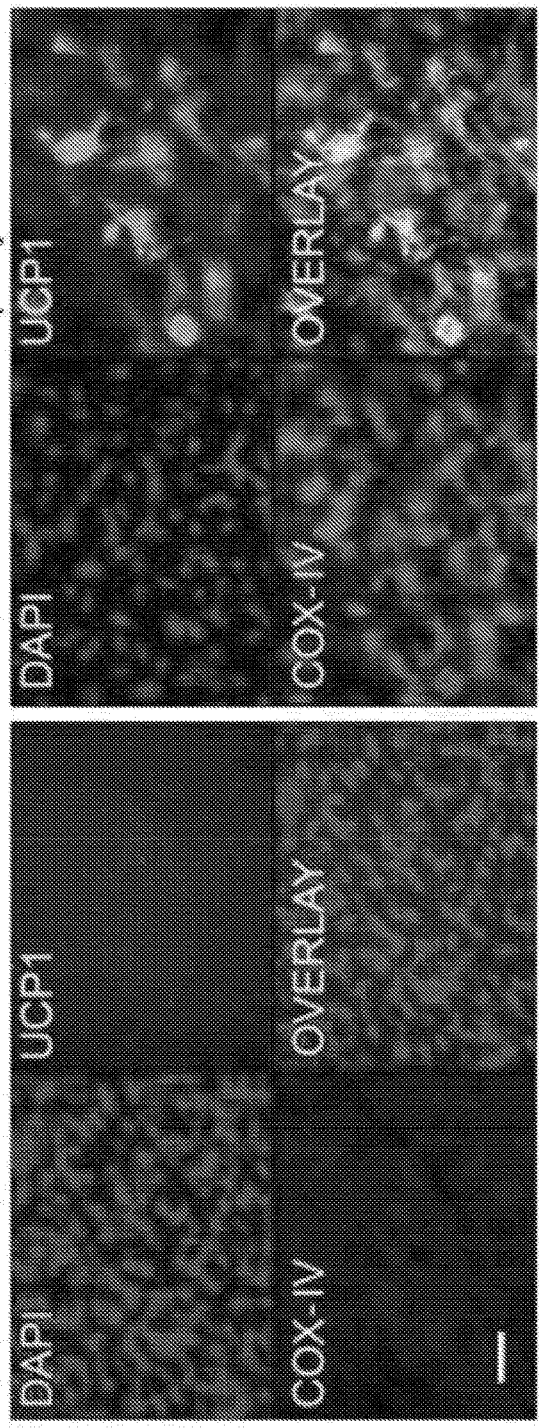
Figure 4D:
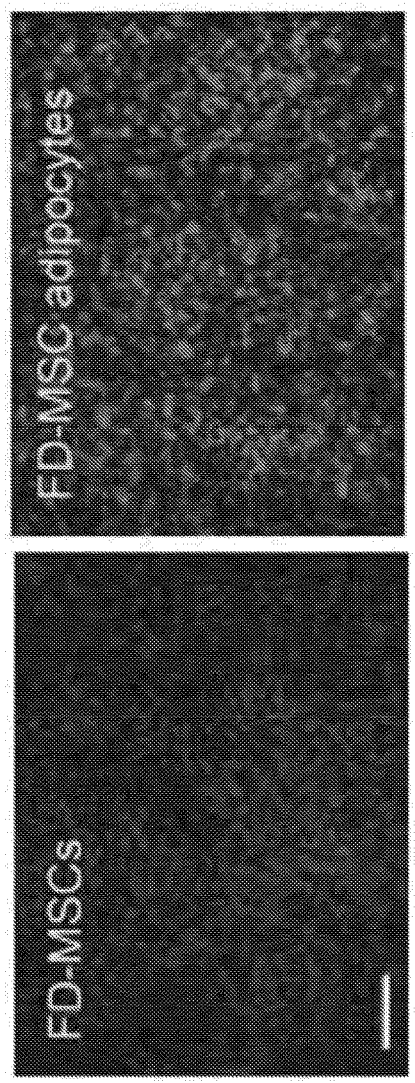

Adipocyte differentiation of FD-MSCs originating from distinct ES (H1 and H9) and iPS cell lines (skin fibroblast and CD34+ cord blood derived) resulted in increased expression of key proteins normally associated with thermogenically active beige and brown adipocytes, including the mitochondrial uncoupling and respiratory chain proteins UCP1 and COX-IV (FIG. 4B, FIG. 4C and FIG. 9A-9B). The lipid droplet associated protein perilipin (PLIN), which is necessary for the mobilization of fatty acids, showed increased expression that was coordinated with increased lipid droplet formation (FIG. 4B and FIG. 4D).

Figure 4E:
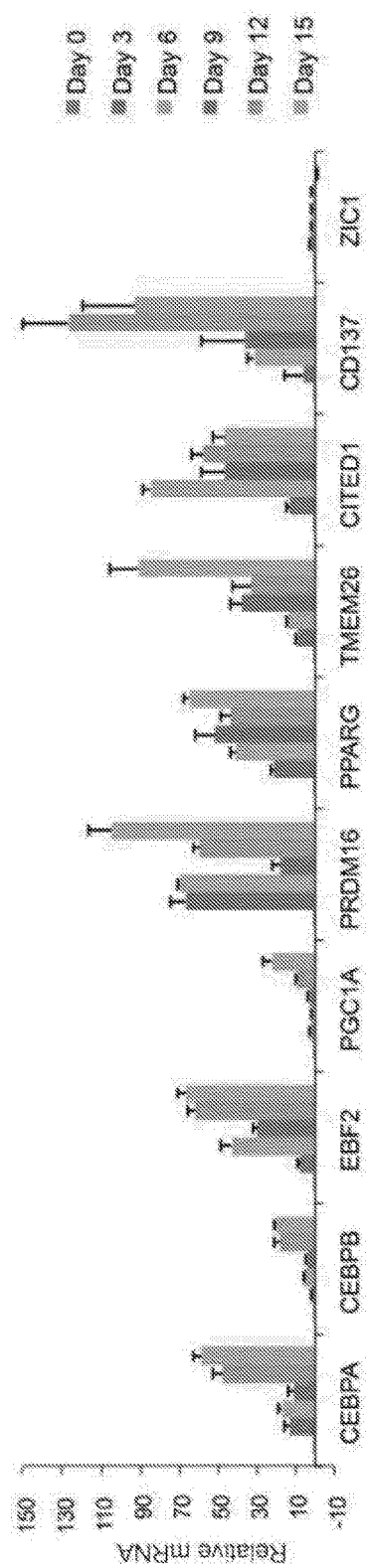
Figure 9B:
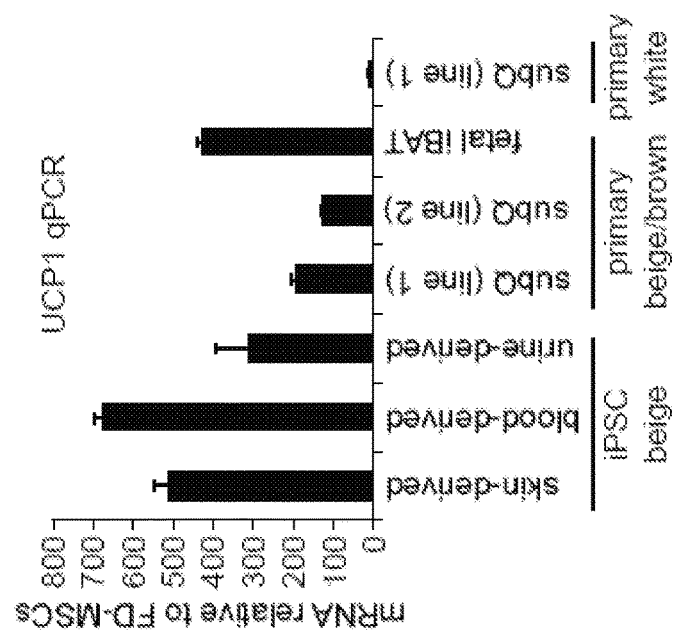
FIGS. 9A-9L show comparisons of iPSC-derived adipocytes with adipocytes derived from primary tissues.
Figure 9A:
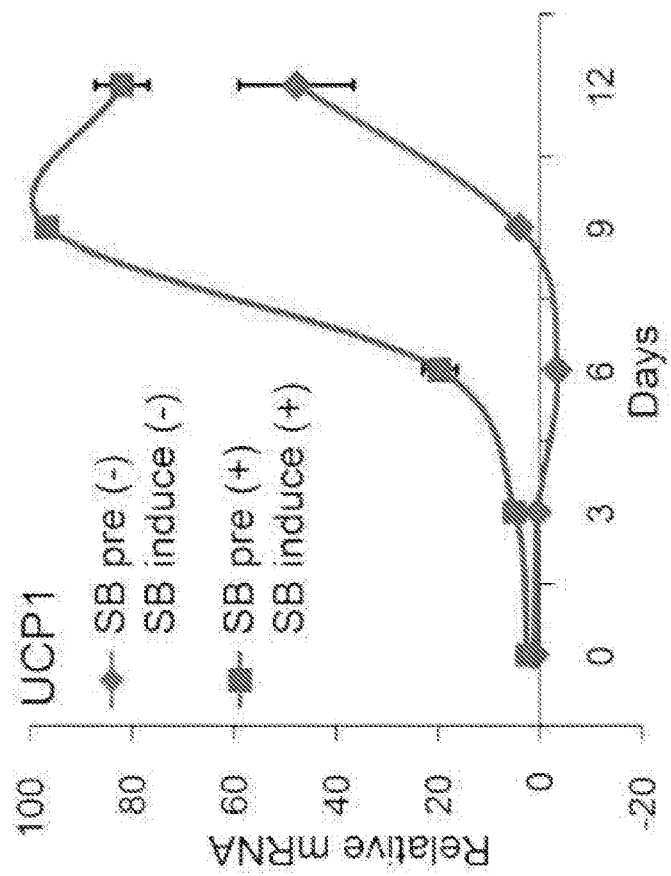
Figure 9C:
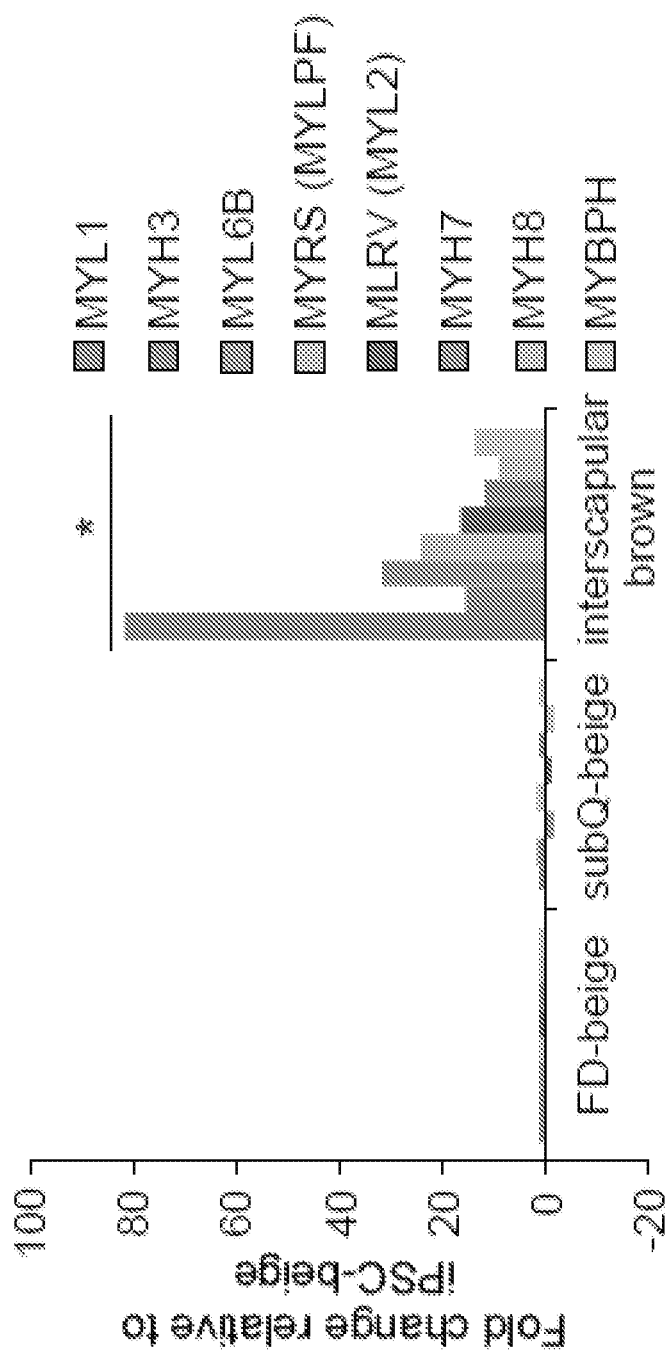
Figure 9D:
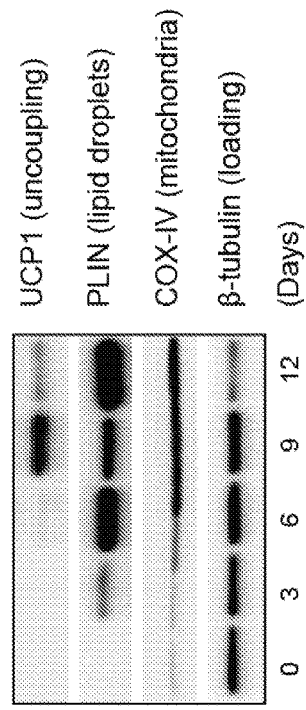
Figure 9E:
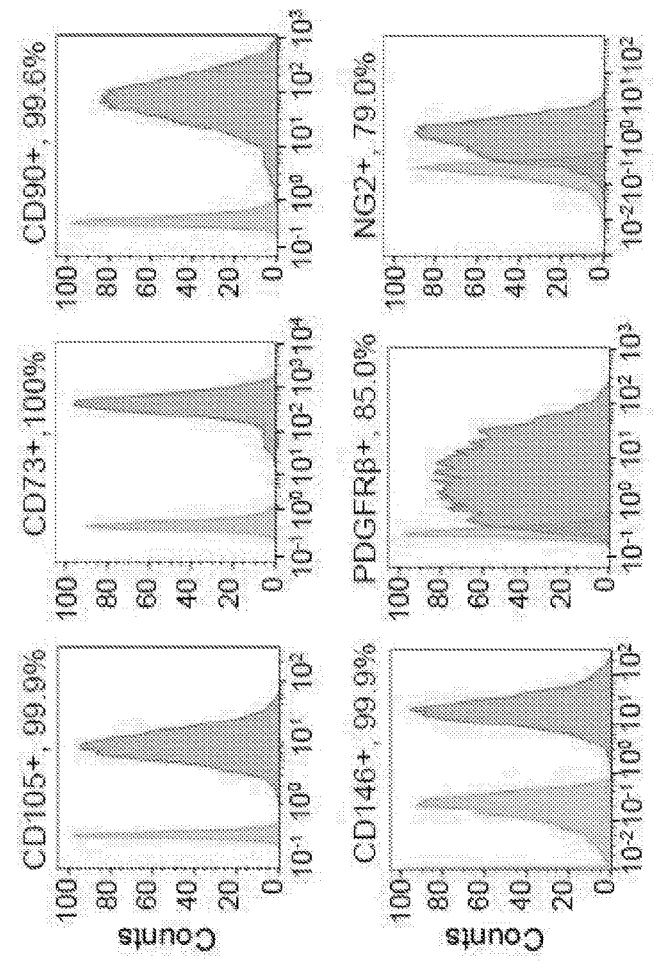
Figure 9F:
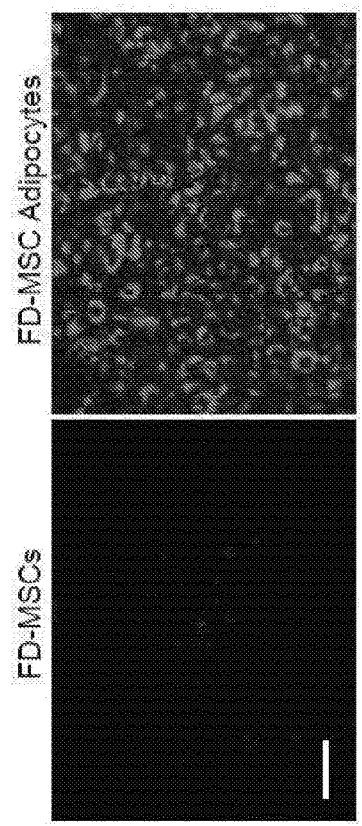
Figure 9G:
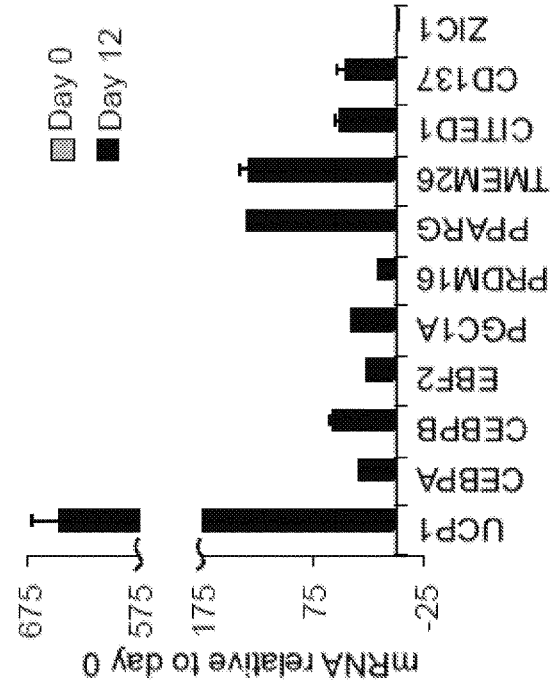
Figures 9H, 9I:
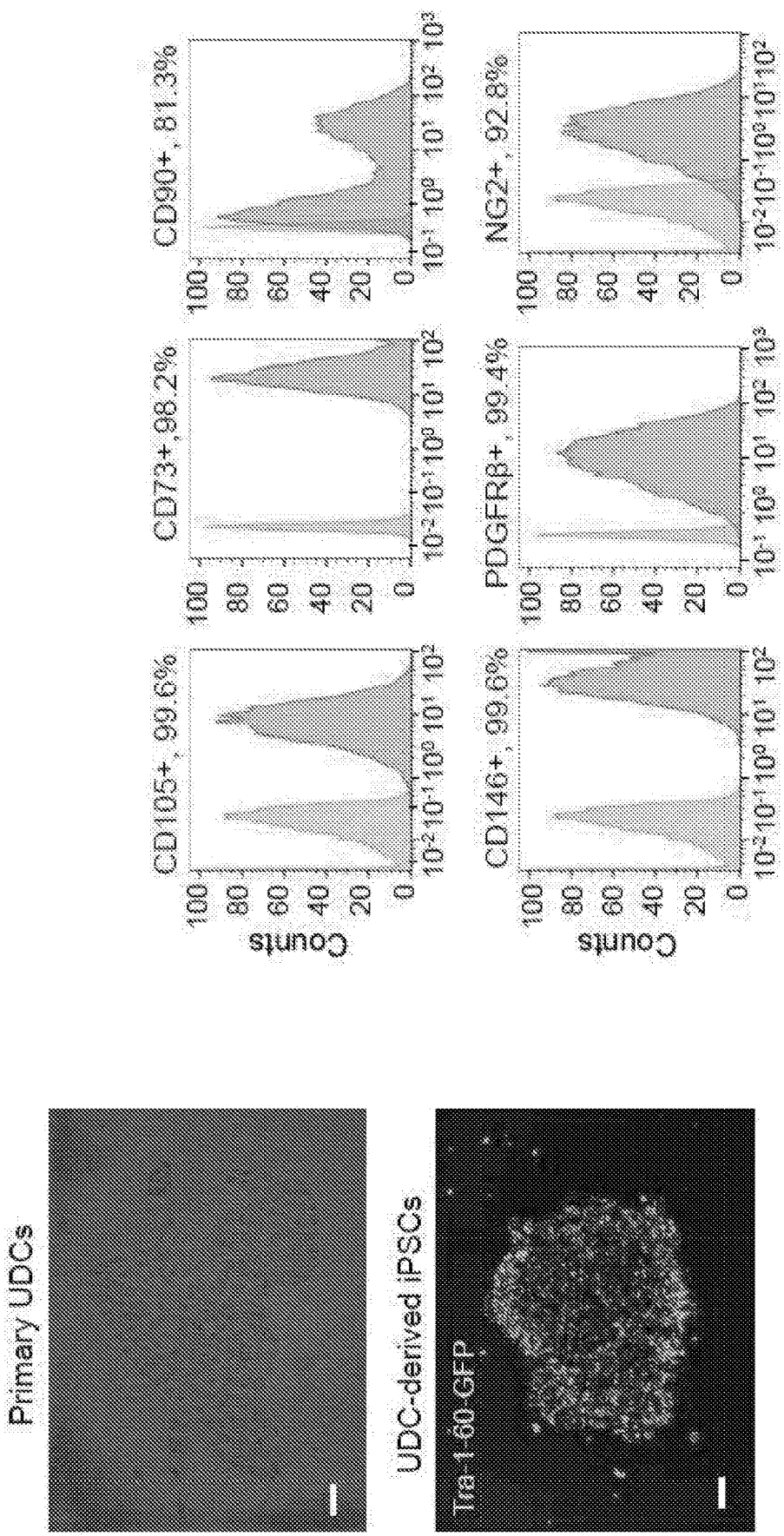
Figure 9K:
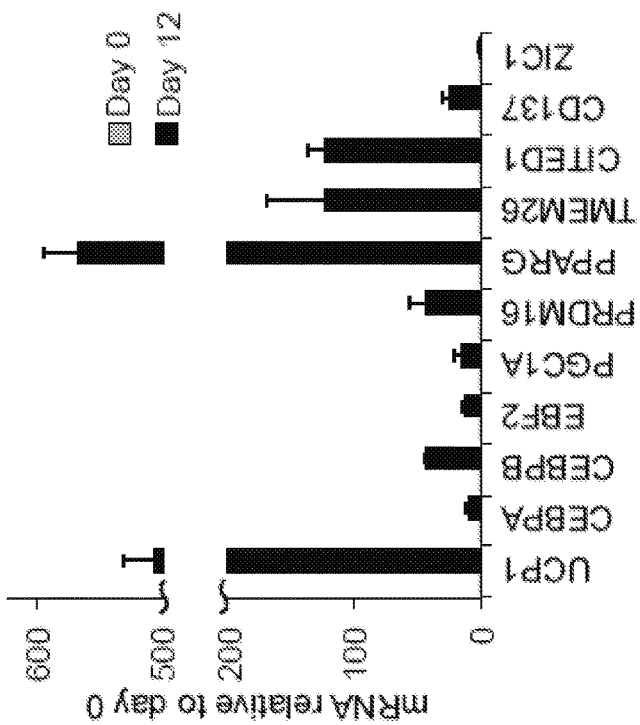
Figure 9J:
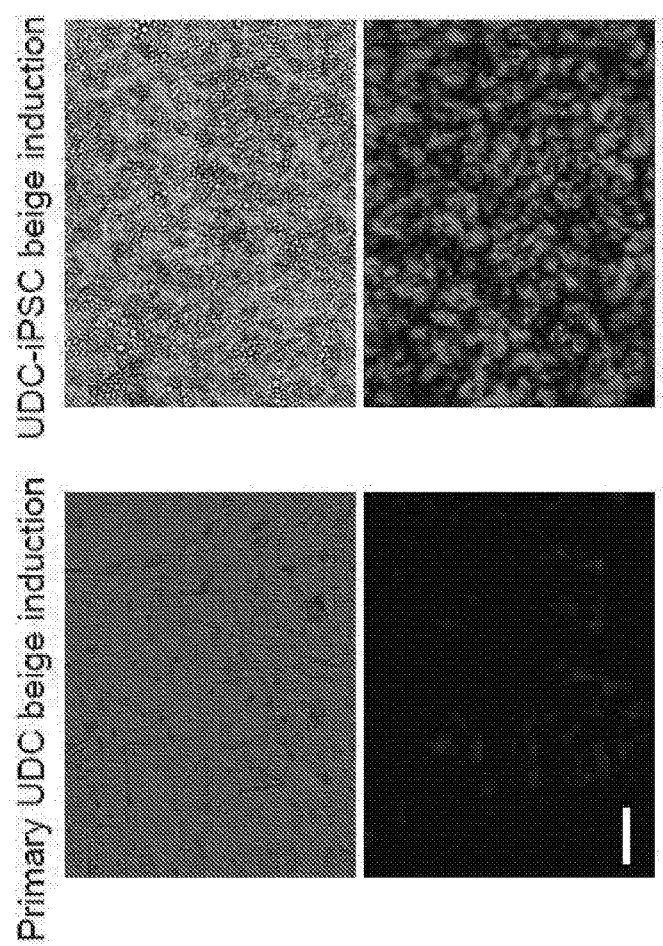
Figure 9L:
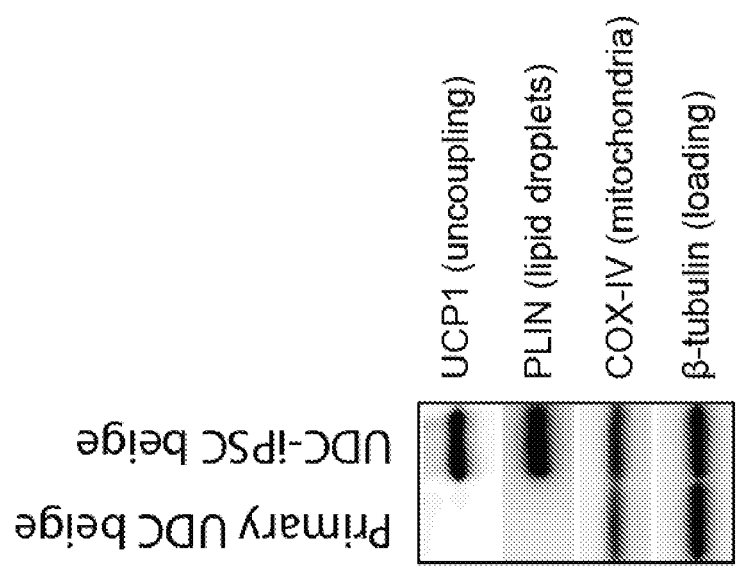

FD-MSCs that originated from additional iPSC cell lines (CD34+ cord blood- and urine-derived cells) displayed the same phenotypic and molecular changes as the ones derived from skin-derived iPSCs (FIG. 9A-9I). iPSC-derived adipocytes also displayed similar or higher expression of UCP1 compared to differentiated adipocytes derived from human subcutaneous (subQ) and fetal interscapular BAT (iBAT) precursors (FIG. 9B). In iPSC-derived adipocytes, expression of transcription factors that regulate beige and brown adipocyte development also increased during differentiation, including CCAAT/enhancer-binding protein alpha/beta (CEBPA/B), EBF2, PGC1A, PRDM16, and PPAR-g (FIG. 4E; Wang and Seale, 2016).

Expression of transcription factors known to regulate the development of beige and brown adipocytes also increased during differentiation, including CEBPA/B, EBF2, PGC1A, and PRDM16 and PPARG (FIG. 4E)[18]. Differentiating FD-MSCs display increased transcription of beige specific marker genes such as TMEM26, CITED1 and CD137, but not ZIC1, a classical brown adipocyte marker (FIG. 4E)[1].

Figure 4F:
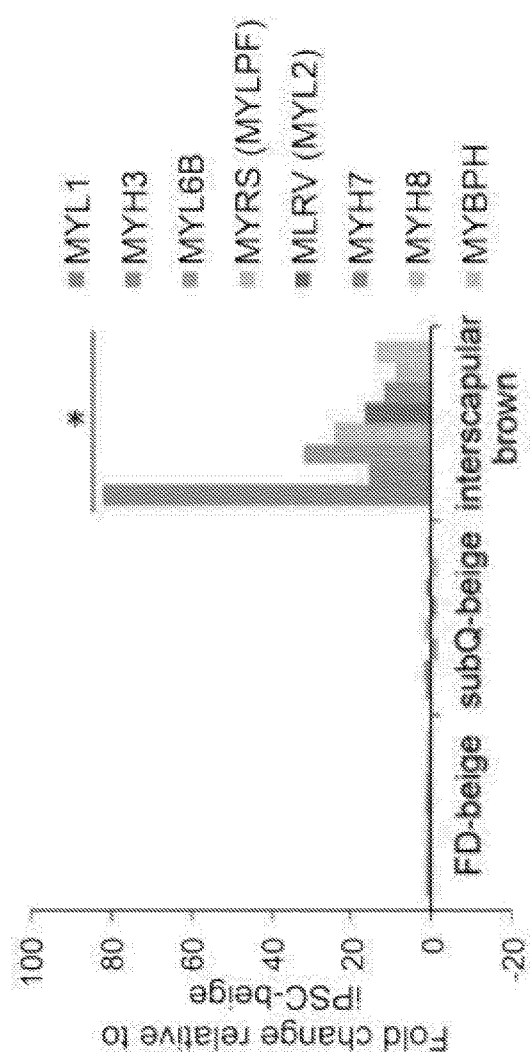

Mass spectrometry analysis of human fetal interscapular brown adipogenic precursors differentiated into mature adipocytes shows a strong myosin protein expression signature consistent with their paraxial mesoderm origin (FIG. 4F)[38]. This signature was absent from human subcutaneous white and FD-MSC adipogenic precursors that were induced to become beige adipocytes.

Figure 4G:
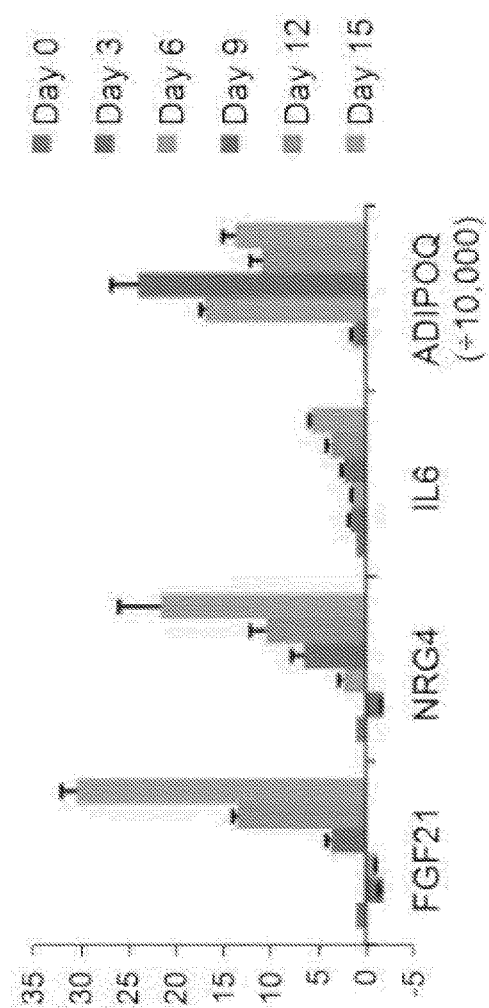

Finally, beige adipogenesis of FD-MSCs resulted in increased transcription of genes that encode secreted factors (FGF21, NRG4, IL-6, ADIPOQ, C1Q, and collagen domain containing ADIPOQ) shown in mice had a positive impact on metabolic dysfunction (FIG. 4G)[11]. Without being bound by any scientific theory, these data suggested that FD-MSCs can form adipocytes with a molecular profile consistent with beige adipocytes, which may perform anti-diabetic functions beyond increased energy expenditure.

IL-4 Enhanced Differentiation of FD-MSCs into Beige Adipocytes

Studies demonstrated that during cold exposure, group 2 innate lymphoid cells (ILC2s) secrete IL-4 to directly stimulate PDGFRα+ adipogenic precursors within subcutaneous adipose and enhance their differentiation into beige adipocytes[39].

Figure 4H:
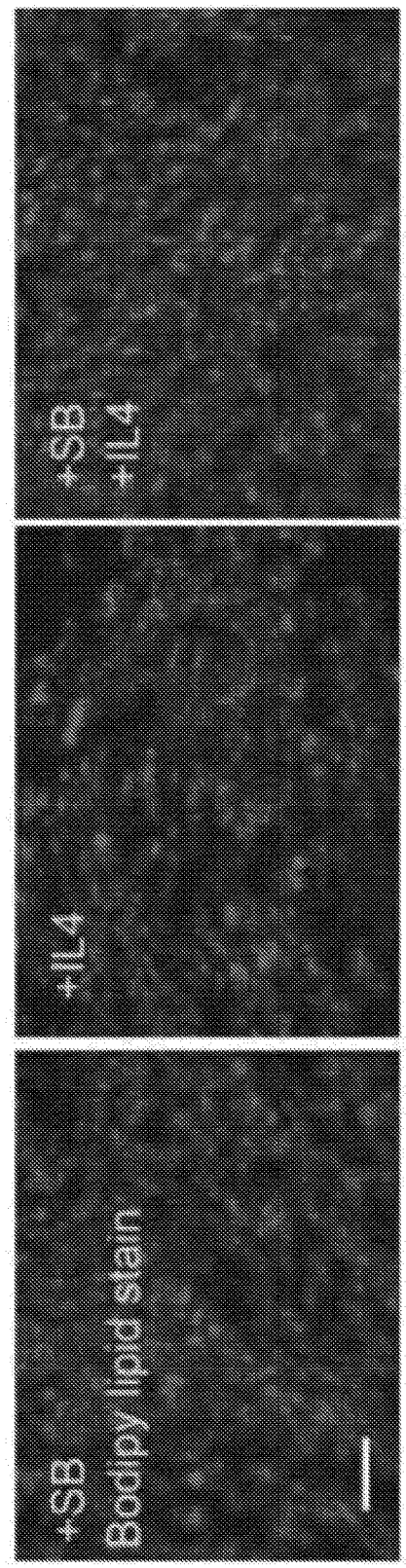
Figure 4I:
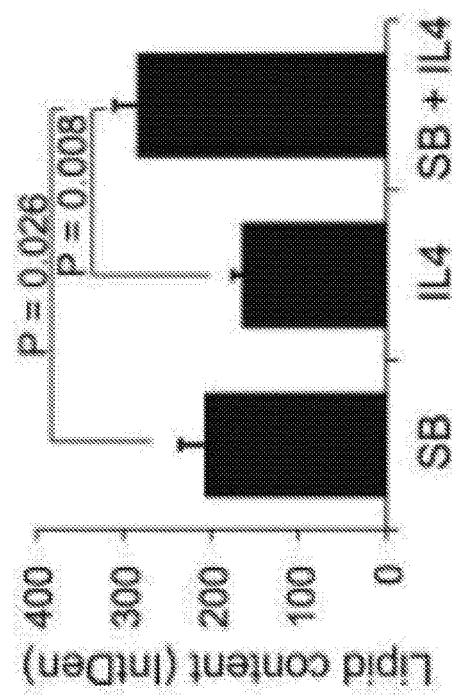
Figure 4J:
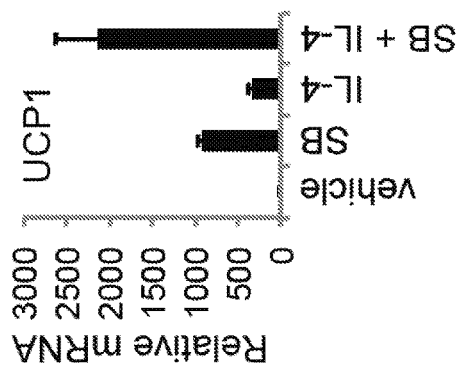
Figure 4K:
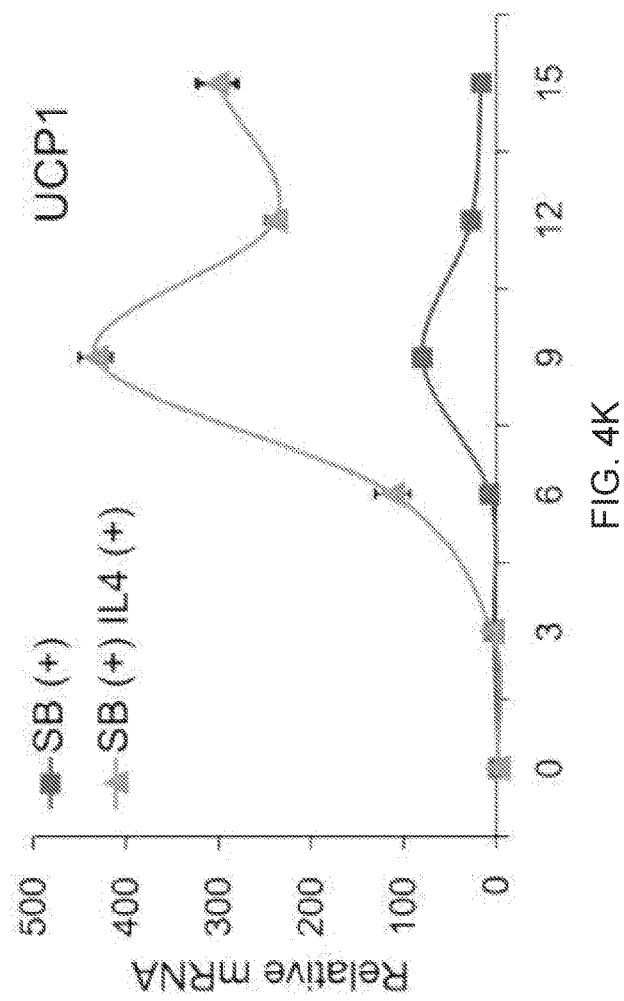
Figures 4L, 4M:
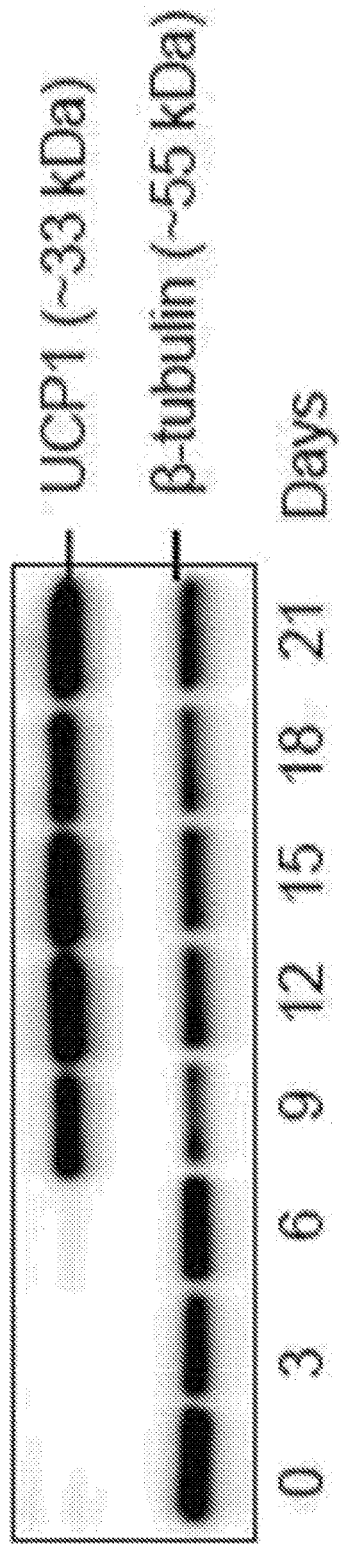

To determine whether IL-4 had an effect on FD-MSCs, cells were pretreated with IL-4 with or without SB for 2 days prior to adipogenic differentiation, which led to a significant increase in the number of multilocular adipocytes compared to either agent alone (FIG. 4H and FIG. 4I). In addition, pretreatment with IL-4 and SB lead to a synergistic increase in UCP1 transcription and an earlier induction of UCP1 protein expression when compared to SB alone (FIG. 4J and FIG. 4K).

Figure 10A:
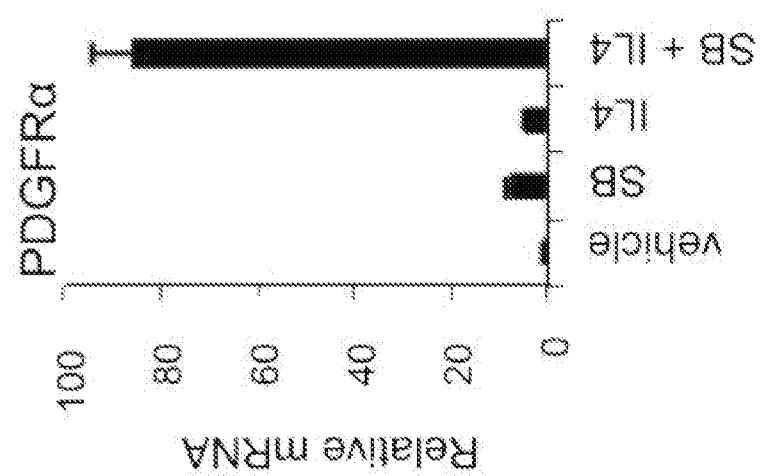
FIGS. 10A-10C depict qPCR analysis of day FD-MSCs treated with vehicle, SB, and IL-4, SB+IL-4 for 2 days and analyzed for transcripts associated with adipogenic precursors. IL-4 increases expression of beige adipogenic precursor markers in cooperation with TGFβ inhibition.
Figure 10C:
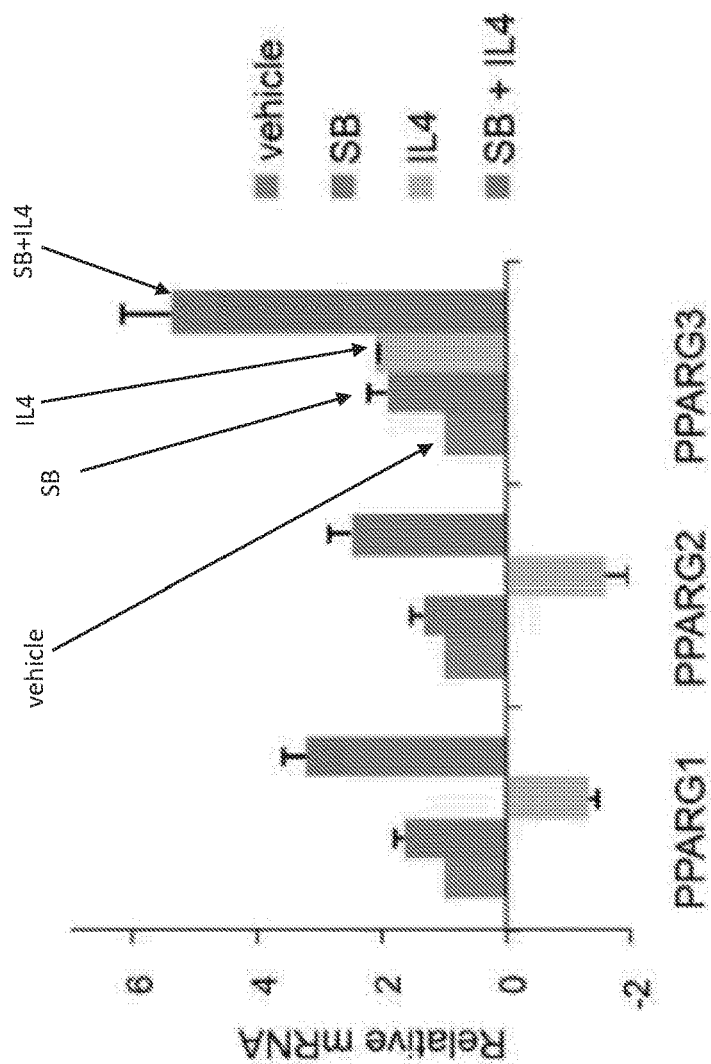
Figure 10B:
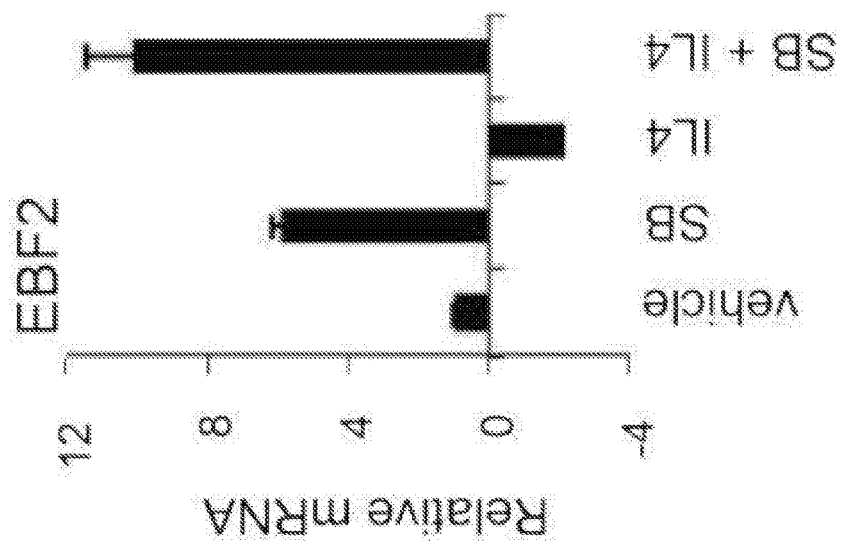

Since IL-4 is only present in cultures prior to adipogenic differentiation, it was reasoned that it may act with SB to enhance the transition of FD-MSCs into FD-beige adipogenic precursors. Indeed, IL-4 had little effect alone, but when added together with SB during the pretreatment, increases in transcription of beige adipogenic precursor markers, including PDGFRα+ and EBF2 (FIG. 10A and FIG. 10B) were observed. Furthermore, PPARG is known to be enriched in adipogenic precursors and observed increased expression of all three PPARG isoforms when FD-MSCs were treated with both SB and IL-4 for 2 days (FIG. 10C)[40]. Without being bound by any scientific theory, these results suggested that IL-4 collaborates with TGFβ inhibition in FD-MSCs to enhance beige adipogenesis by increasing their commitment toward beige adipogenic precursors.

Figure 5B:
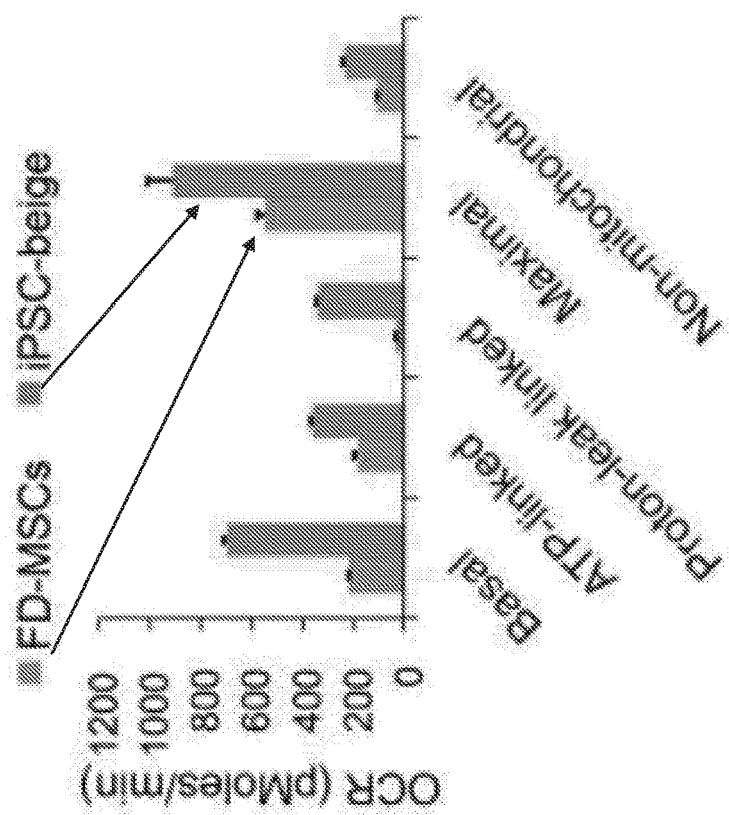
FIGS. 5A-5L depict respiratory activity and mitochondrial depolarization in FD-beige adipocytes.
Figure 5A:
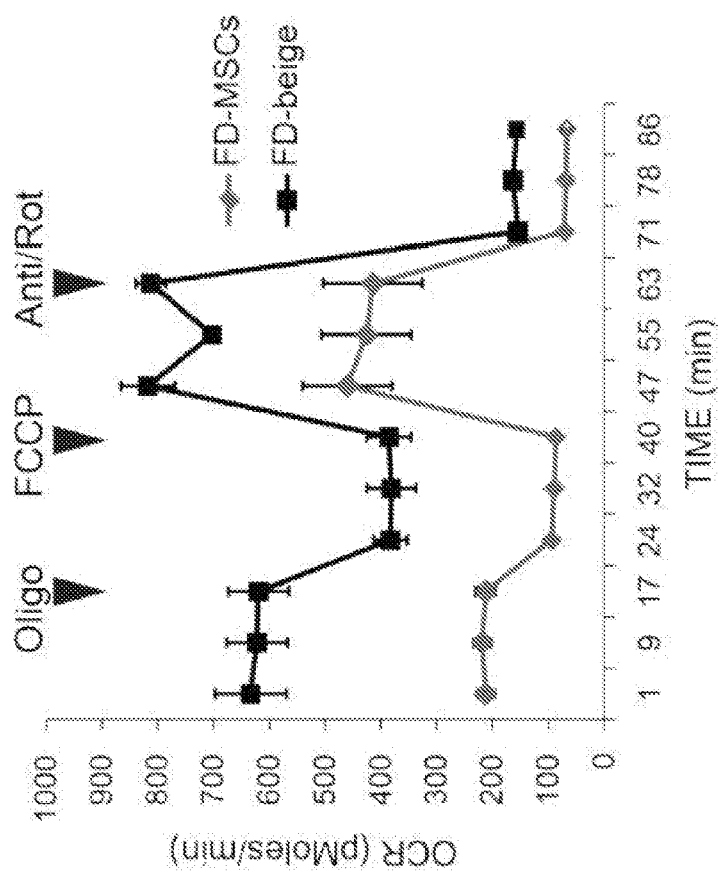

FOXF1-Derived Beige Adipocytes Displayed Enhanced Respiratory Activity and Uncoupling; iPSC-Beige Adipocytes Displayed Enhanced Respiratory Activity and Uncoupling To determine whether the molecular profile associated with FOXF1-derived beige (FD-beige) adipocytes resulted in enhanced metabolic activity, mature adipocytes were subjected to Seahorse-XF analysis. Compared to undifferentiated FD-MSCs, mature FD-beige adipocytes display increased basal, ATP-linked, proton leak-linked, maximal and non-mitochondrial respiration (FIG. 5A and FIG. B). ATP-linked respiration was approximately 2-fold higher in FD-beige adipocytes compared to FD-MSCs, whereas uncoupled respiration was 10.4 fold higher.

Figures 5C, 5D:
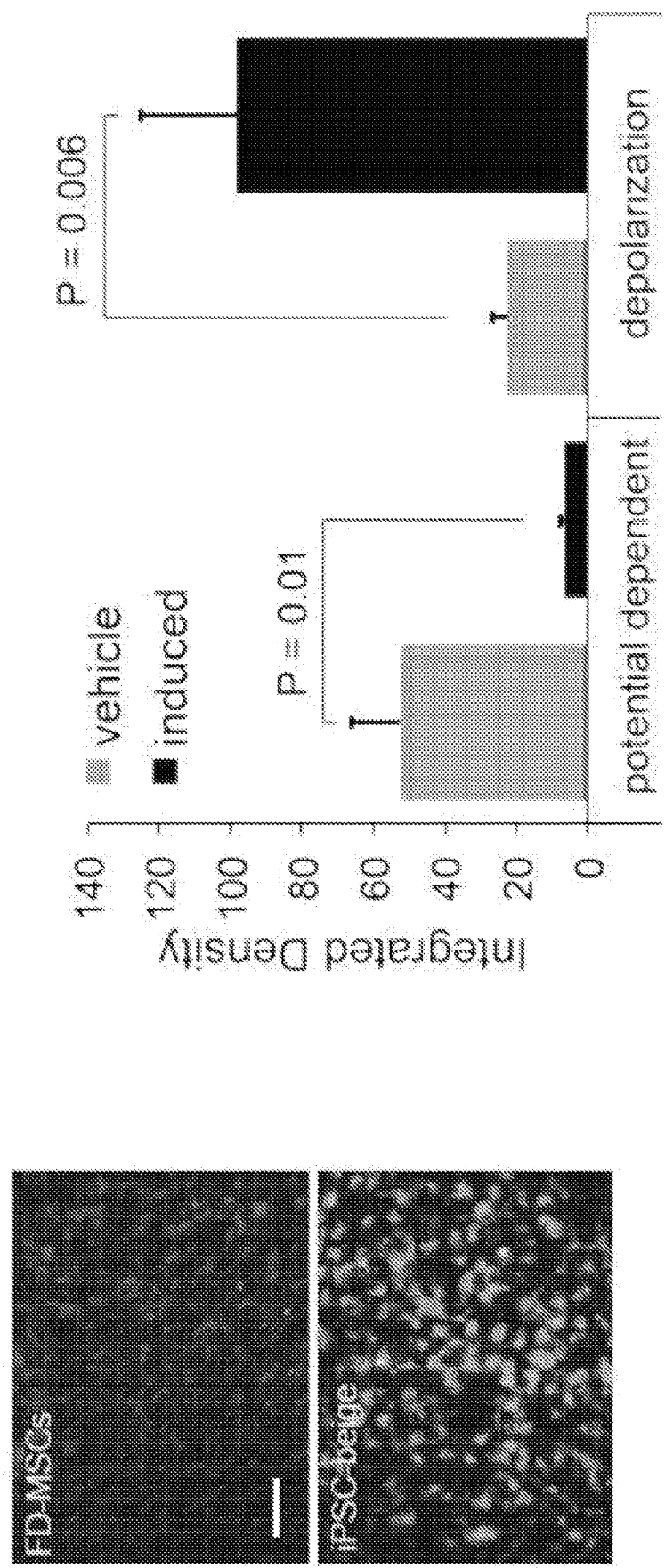

In agreement with increased proton leak-linked respiration, JC-1 dye stained FD-beige adipocytes showed accumulation of green-fluorescent monomers that indicated a shift in mitochondrial depolarization compared to untreated FD-MSCs, which contain red-fluorescent J-aggregates at hyperpolarized membrane potentials (FIG. 5C and FIG. 5D). These results suggested that FD-beige adipocytes displayed enhanced respiratory activity and uncoupling consistent with the expression of UCP1 as is found in thermogenically active adipocytes.

Figure 5F:
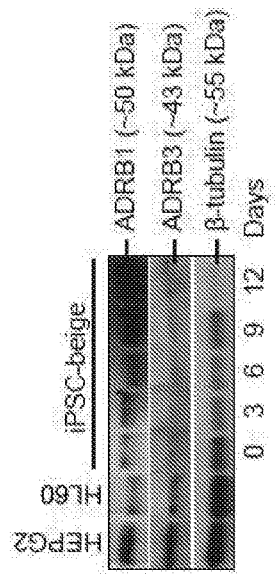
Figure 5H:
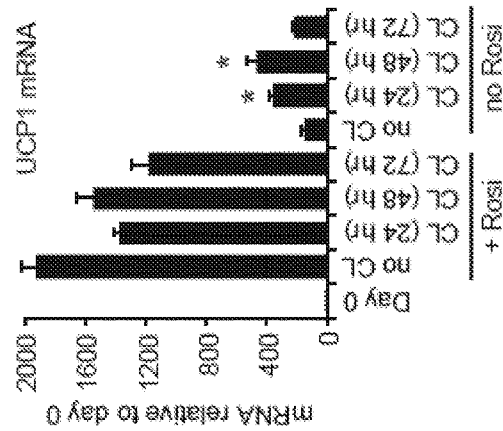
Figure 5E:
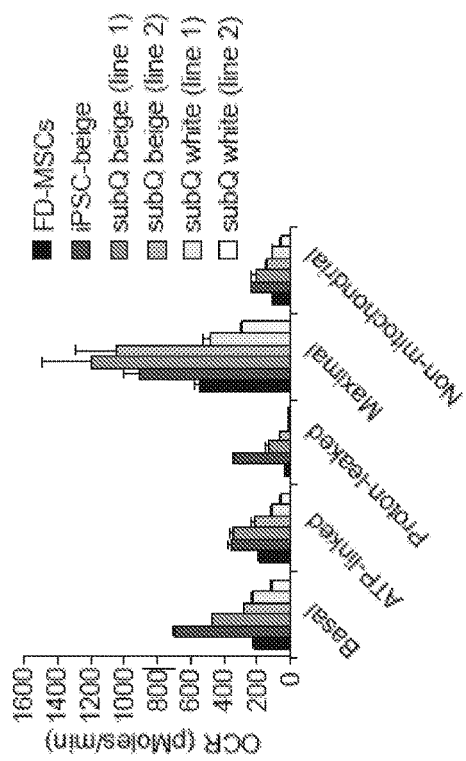
Figure 5G:
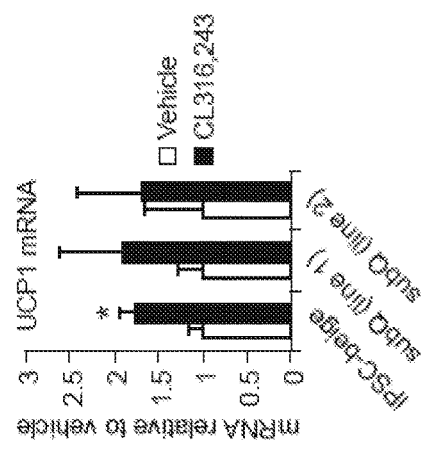
Figure 5J:
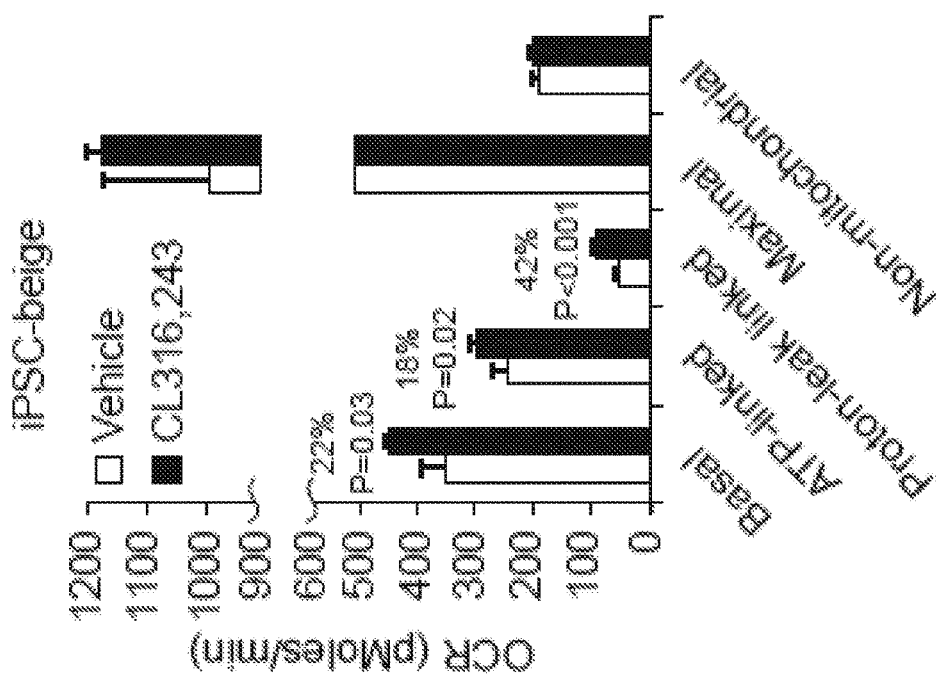
Figure 5I:
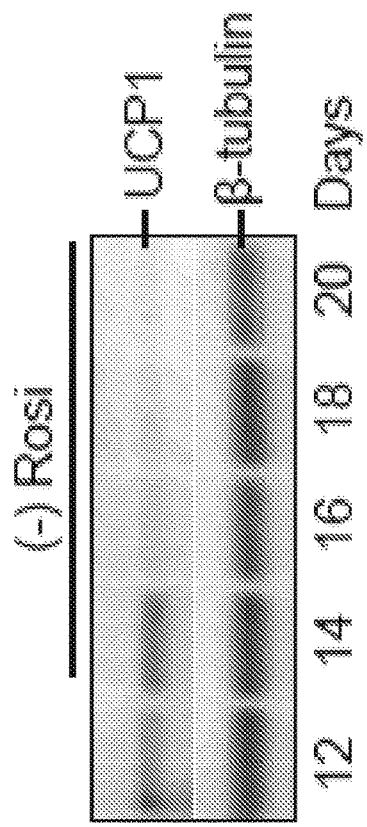
Figure 5L:
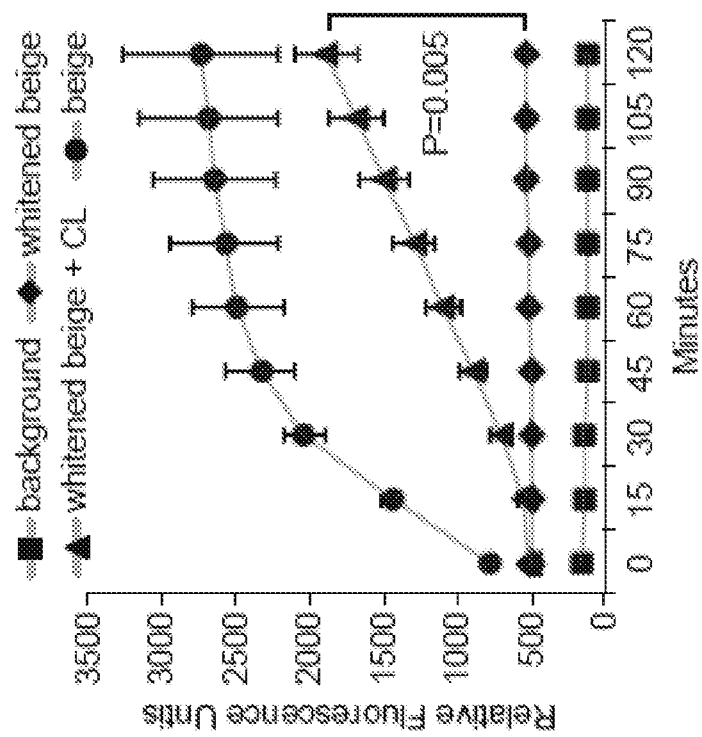
Figure 5K:
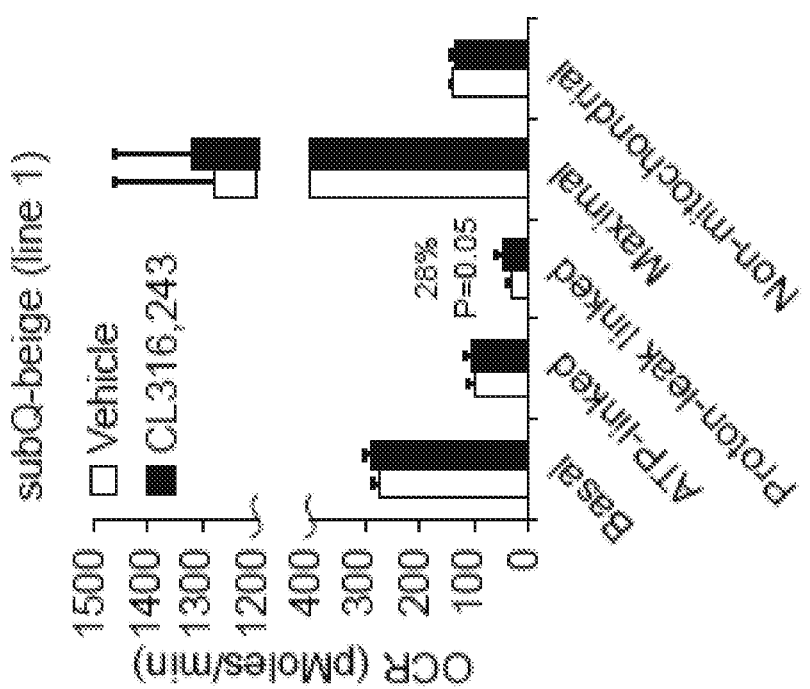

A hallmark feature of beige adipocytes is their ability to increase thermogenesis and respiration in response to b-adrenergic agonists, although the response in humans is known to be weaker than that observed in rodent adipocytes (Liu et al., 2017). iPSC-beige adipocytes expressed both β1- and β3-adrenergic receptors and increased expression of UCP1 upon stimulation with the β3-adrenergic agonist CL316,243 in a manner comparable to primary subcutaneous adipocytes (FIGS. 5F and 5G). CL316,243 also increased UCP1 expression during the initial differentiation of iPSC-beige adipocytes, but the effect was masked or inhibitory in the presence of rosiglitazone, possibly due to overstimulation of the cells (FIG. 5H). Mature iPSC-beige adipocytes whitened in the absence of rosiglitazone for 4 days (as determined by a loss of UCP1) and then treated with CL316,243 for 4 hr increased overall respiration and proton leak to a greater extent than subcutaneous-derived beige adipocytes (FIG. 5I-5K).

Finally, iPSC-beige adipocytes that were whitened during a period of 6 days in the absence of rosiglitazone increased fatty acid (FA) uptake after treatment with CL316,243 (FIG. 5K), suggesting that exogenous fatty acids may represent a major energy substrate for thermogenesis in these cells. These results demonstrated that iPSC-beige adipocytes possess the necessary cellular machinery required for increased thermogenesis in response to (3-adrenergic stimuli.

Developmental Reprogramming in a Patient with Compromised Beige Adipogenesis

Figure 11:
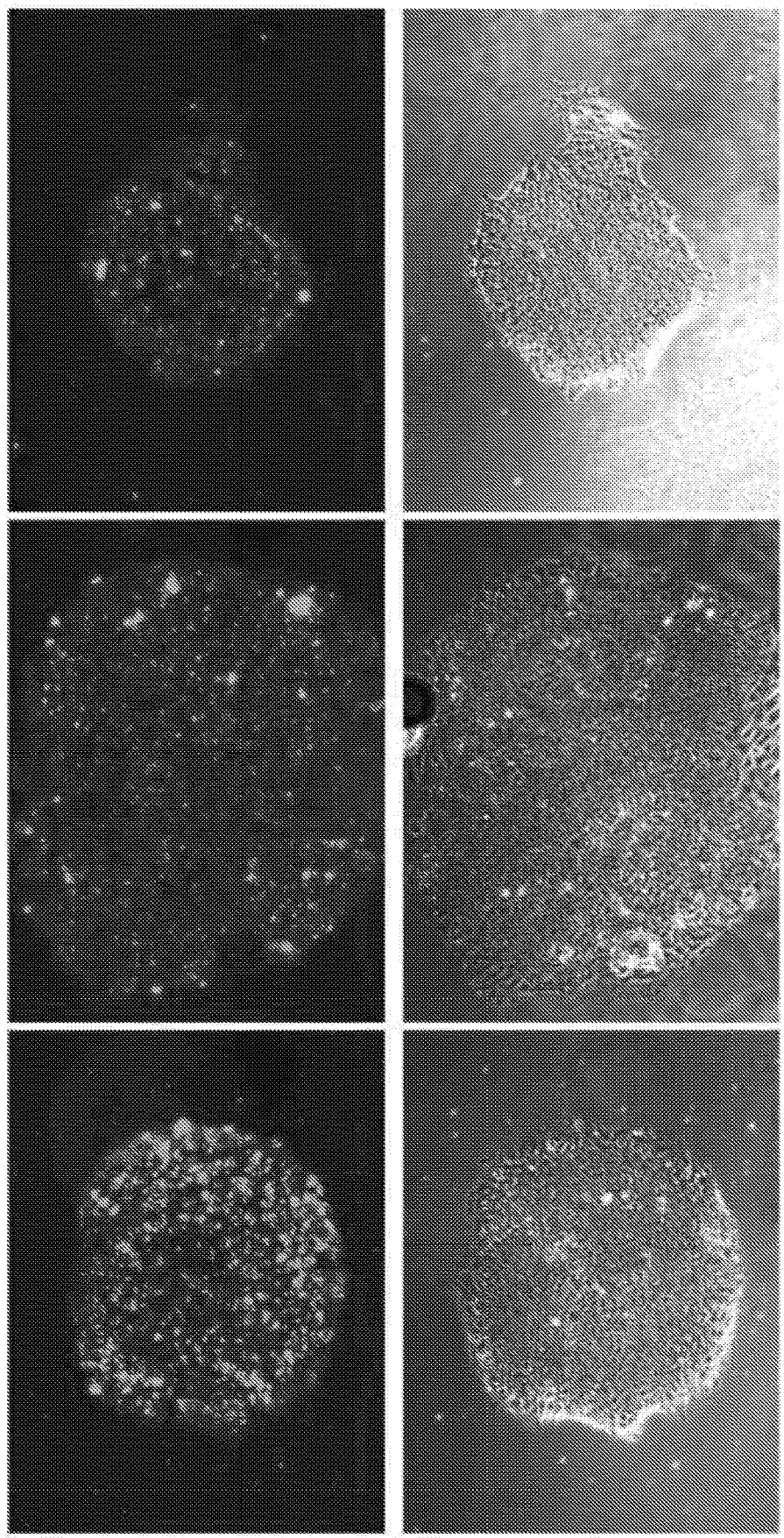
FIG. 11 shows images depicting Tra-1-60+ live cell staining (upper panel) and phase contrast (lower panel) of representative iPSC colonies generated from type 2 diabetic subcutaneous apidogenic precursors.
Figure 12:
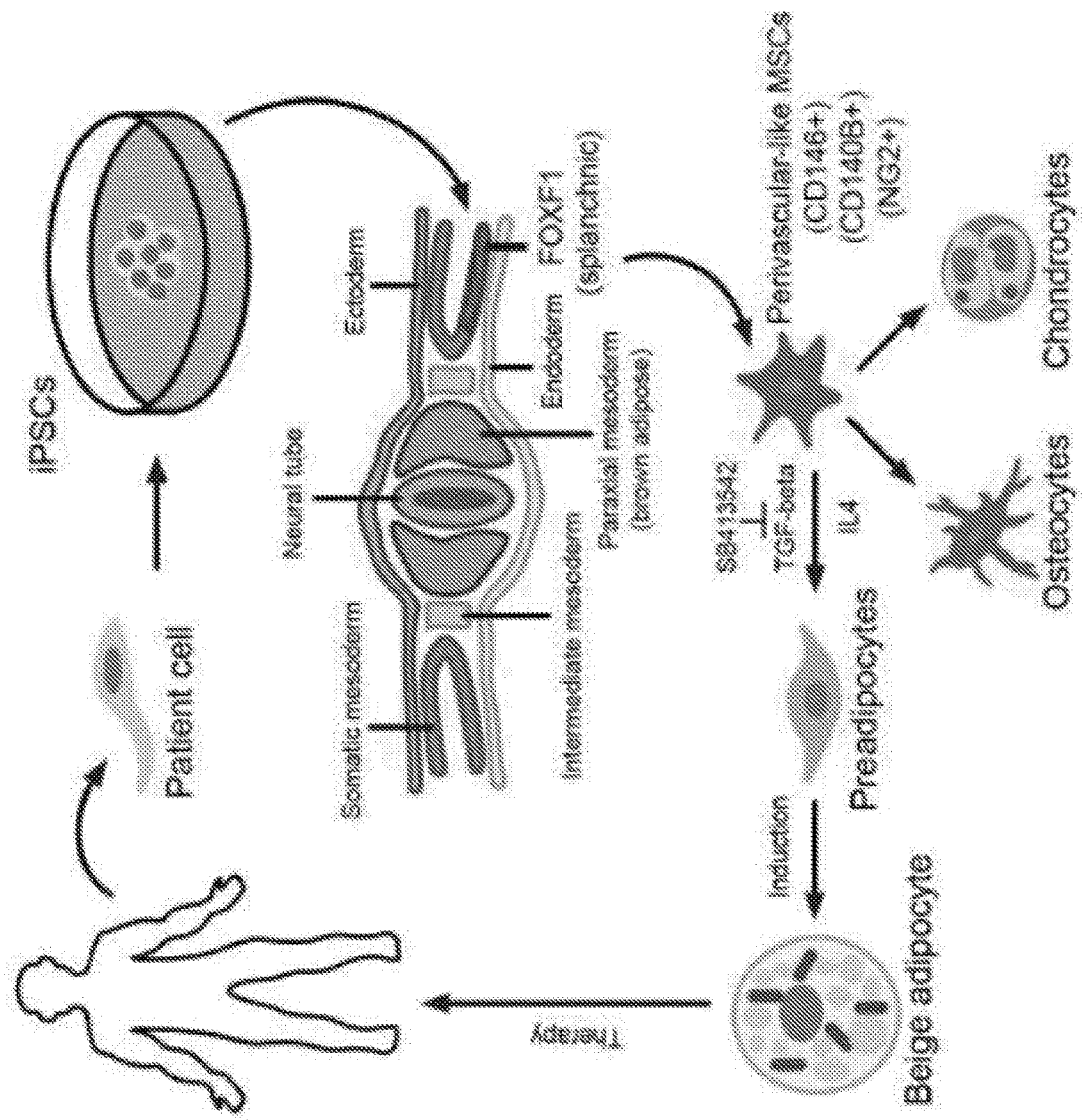
FIG. 12 is a schematic depicting the development of a robust method for derivation of human beige adipocytes from PSCs for therapies to treat a metabolic disease (e.g., obesity and/or diabetes). Beige adipocytes can be derived from FOXF1+ splanchnic mesoderm. Inhibition of TGFβ signaling and treatment with IL-4 primes FOXF1-derived MSCs to form an adipogenic precursor population. Dysfunctional adipogenic precursors can be reprogrammed into beige adipocytes that secrete anti-diabetic factors and improve insulin sensitivity and glucose uptake. Cells or secreted factors derived from these cells may be used to treat metabolic disease.
Figure 13:
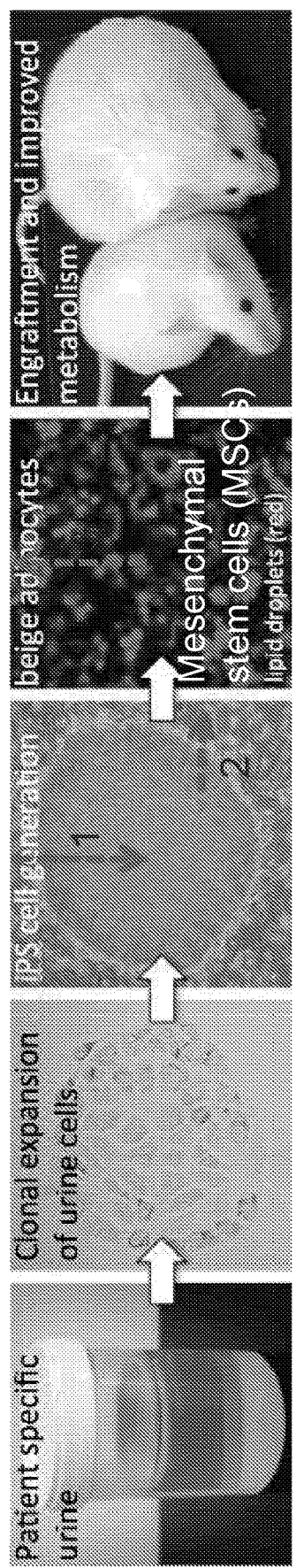
FIG. 13 is a schematic depicting a non-limiting example of a strategy to generate human beige adipocytes from iPSCs.

As a proof of principle to determine whether the method could be used to generate a source of syngeneic beige adipocytes from patients that lack beige adipogenic potential, subcutaneous adipogenic precursors from a 76-year old type 2 diabetic patient were reprogrammed and differentiated. Patient derived preadipocytes were reprogrammed with a non-integrating mRNA cocktail of pluripotent transcription factors to form Tra-1-60+ iPSCs that were differentiated into FD-adipogenic precursors (FIG. 11)[41].

Figure 6A:
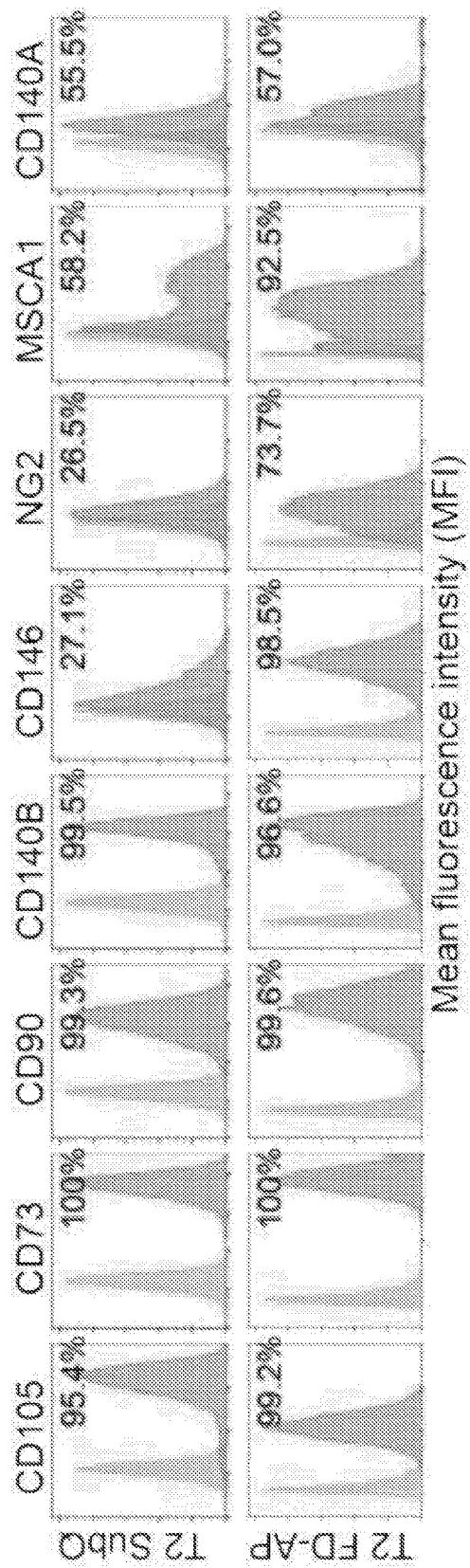
FIGS. 6A-6L depict reprogramming of dysfunctional pre-adipocytes into functional FD-beige adipocytes.
Figure 6B:
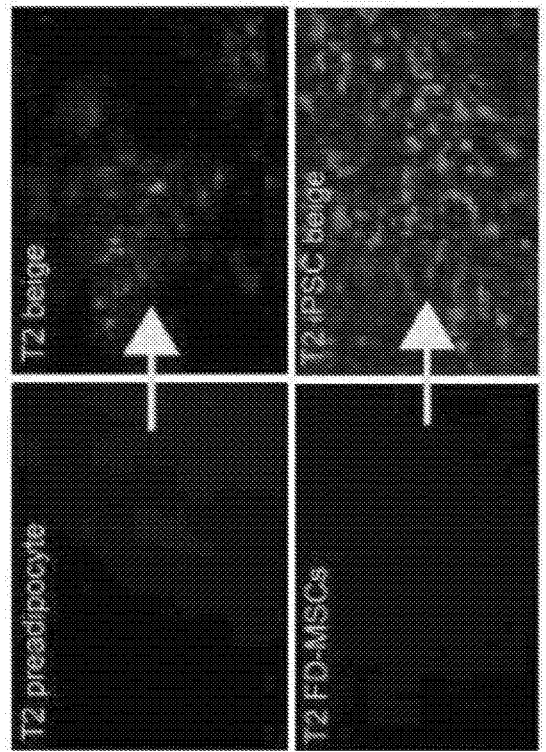
Figure 6C:
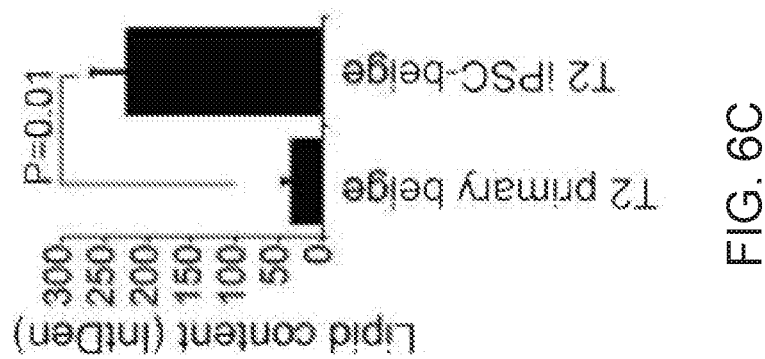

Compared to primary adipogenic precursors, FD-adipogenic precursors displayed similar expression of CD105, CD73, CD90 and PDGFRβ. FD-adipogenic precursors also displayed increased surface expression of the pericyte markers CD146 and NG2 and the adipogenic precursor markers MSCA1 and PDGFRα (FIG. 6A). FD-beige adipocytes exhibited a greater than 6-fold increase in lipid content compared to primary adipocytes (FIG. 6B and FIG. 6C).

Figure 6D:
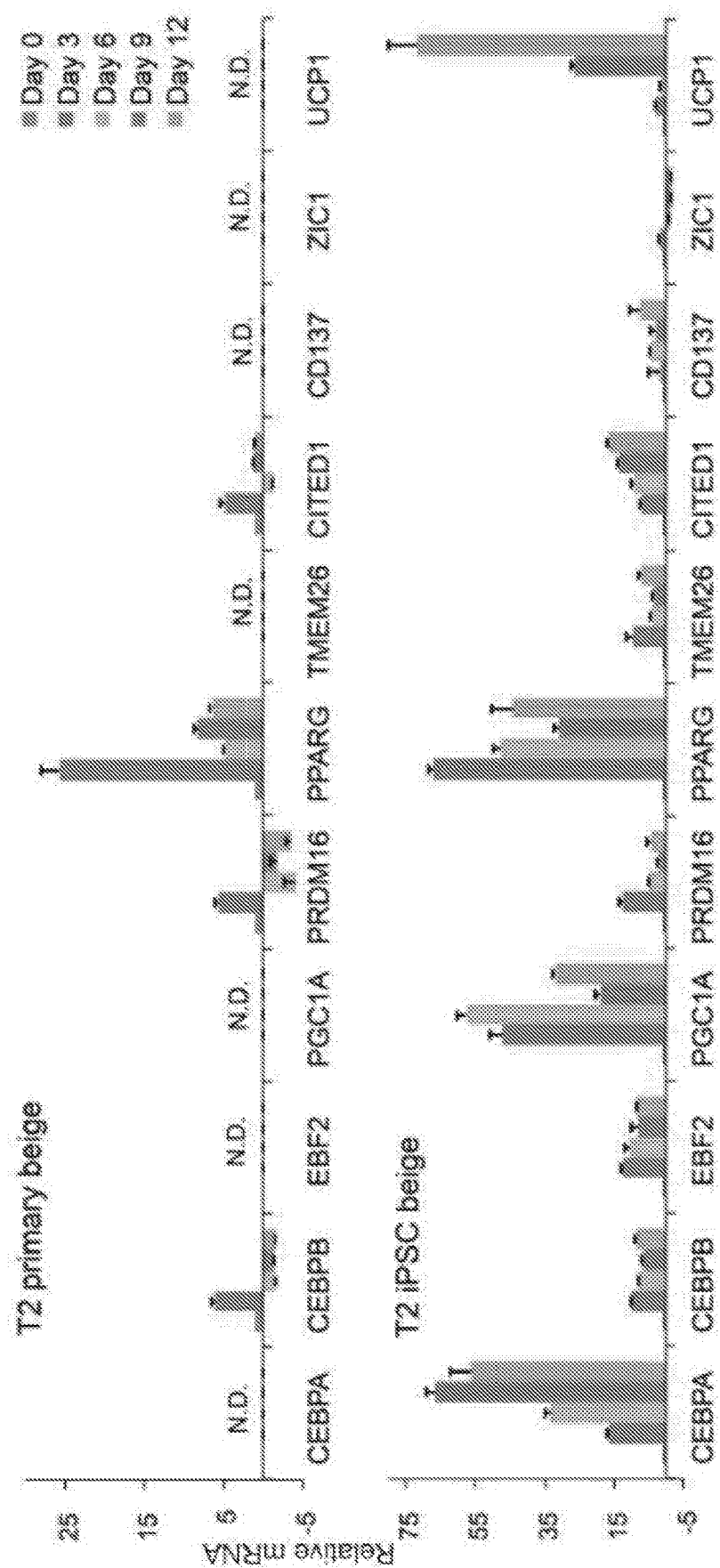
Figure 6E:
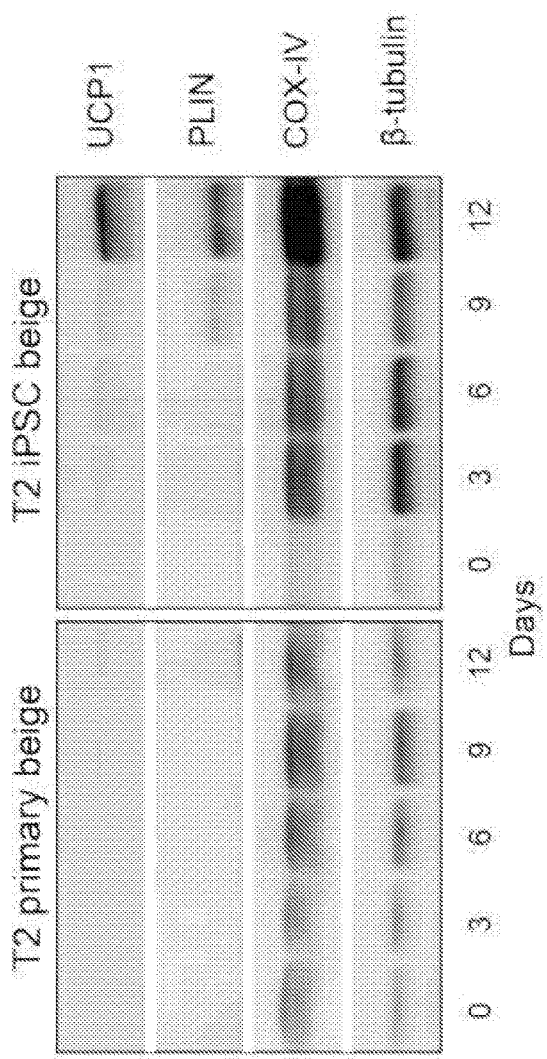
Figure 6F:
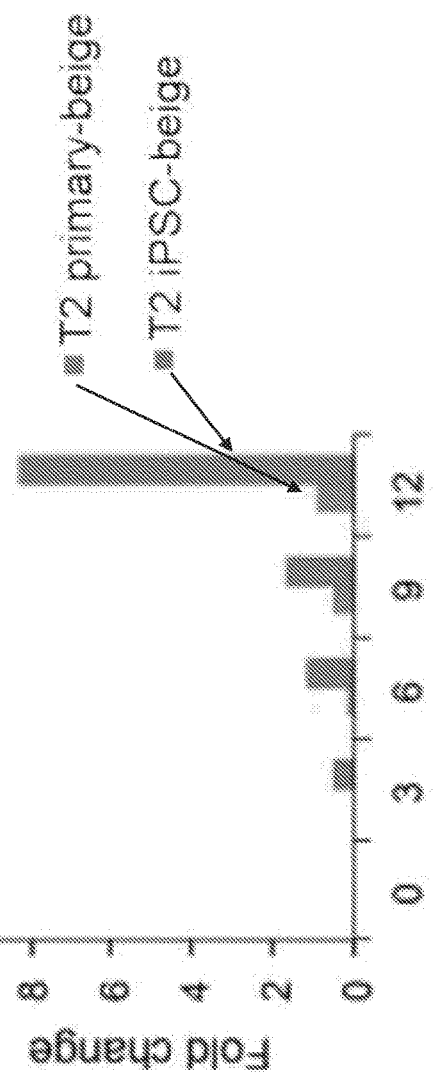
Figure 6H:
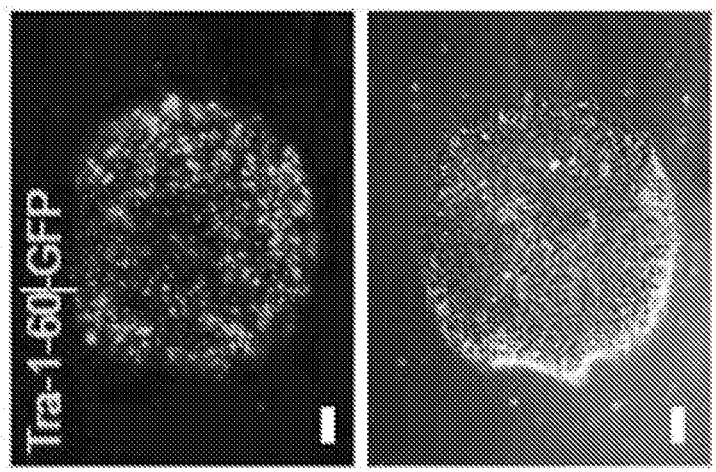
Figure 6G:
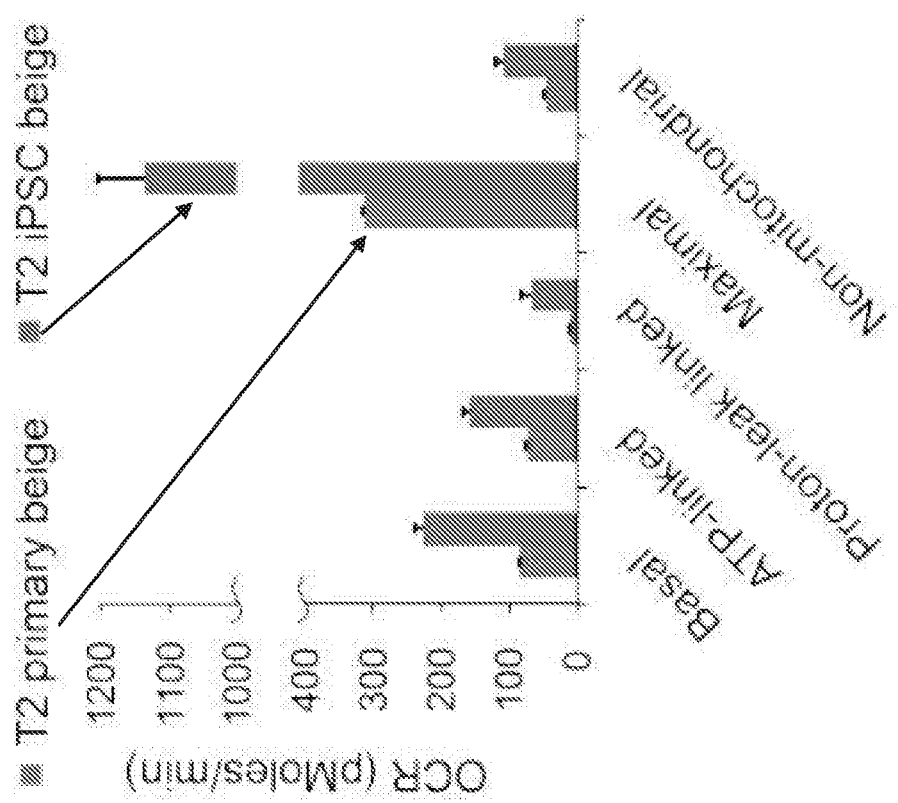

Primary cultures failed to display a transcriptional profile consistent with formation of beige adipocytes, whereas their reprogrammed counterparts displayed to full complement of beige and brown adipogenic biomarkers (FIG. 6D). Reprogrammed beige adipocytes also showed higher protein levels of PLIN, COXIV and UCP1, and increased metabolic activity including increased basal, ATP-linked, proton leak-linked, maximal and non-mitochondrial respiration (FIG. 6E, FIG. 6F and FIG. 6G).

Figure 6I:
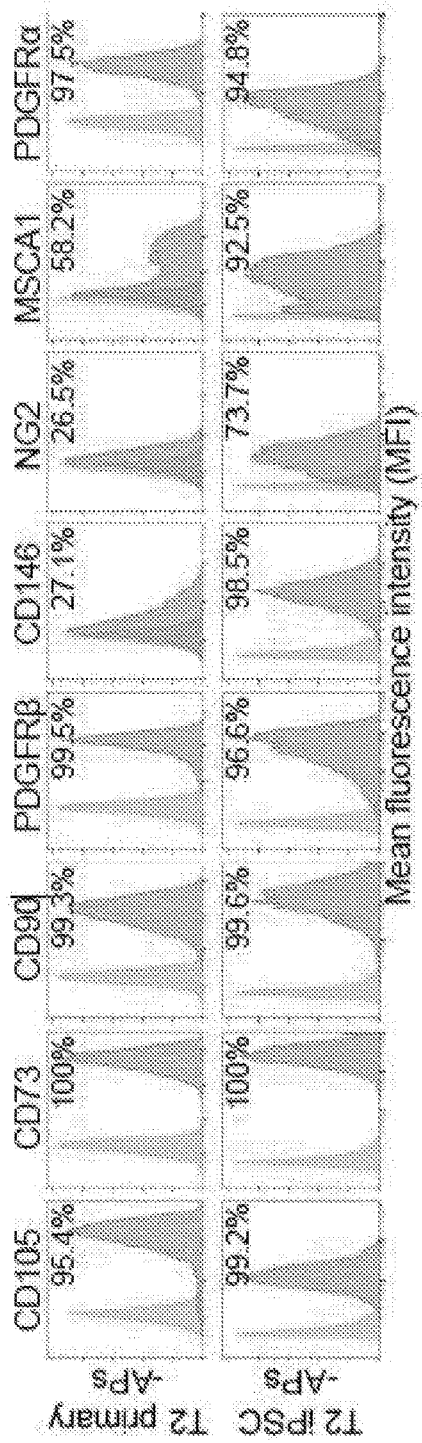

To test whether reprogrammed beige adipocytes secrete anti-diabetic factors that can be used in a syngeneic manner, primary adipocyte cultures from the same patient were treated with FD-beige adipocyte conditioned medium for 3 days prior to insulin challenge. Treatment with FD-beige adipocyte conditioned medium resulted in an approximate 3-fold increase in insulin sensitivity as determined by phosphorylation of AKT, a downstream signaling component of insulin receptor signaling (FIG. 6H and FIG. 6I).

Figure 6L:
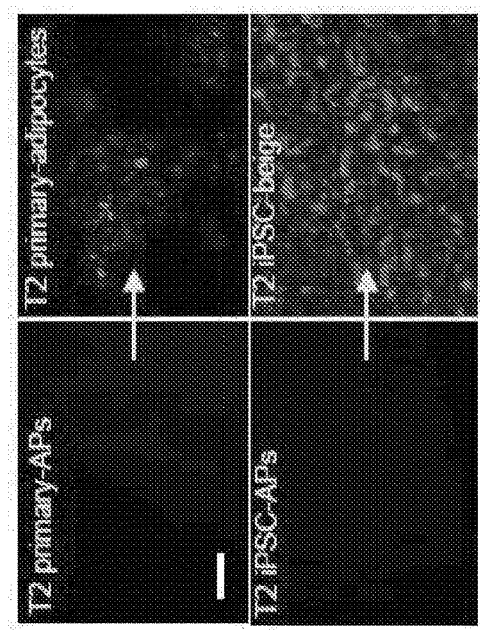
Figure 6K:
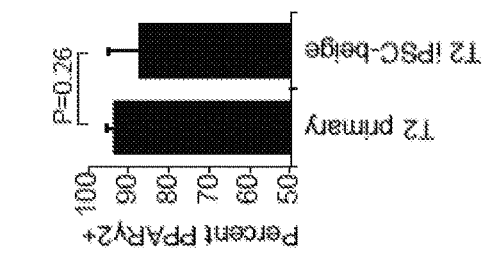
Figure 6J:
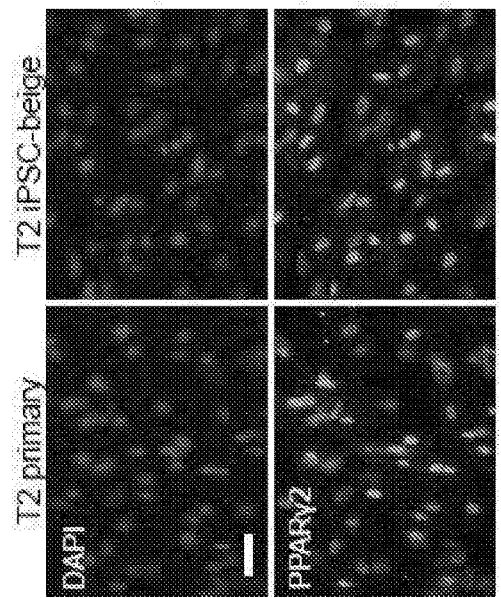

Furthermore, FD-beige adipocyte conditioned medium resulted in a significant increase in glucose uptake of the primary cell cultures at insulin concentrations in the 0.02-2.0 nanomolar range (FIG. 6J). Overall, these results indicated that adipogenic precursors with an inherently low beige adipogenic potential can be reprogrammed and differentiated with the method to produce beige adipocytes with increased thermogenic and anti-diabetic potential.

Figure 7A:
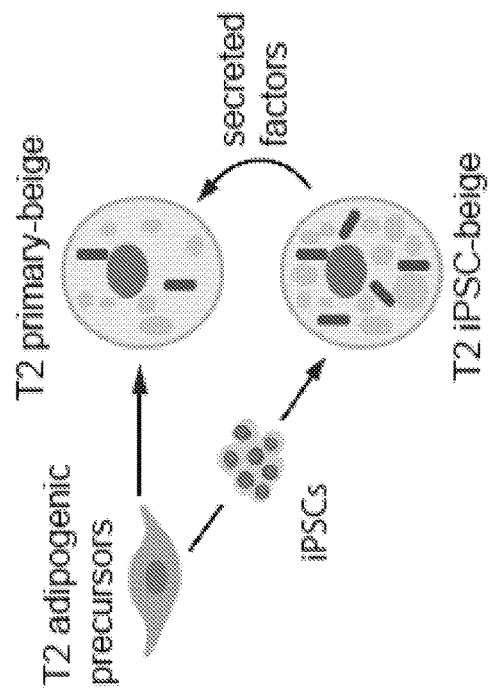
FIGS. 7A-7D show that iPSC-derived beige adipocytes secreted factors that improved insulin sensitivity and glucose uptake.
Figure 7B:
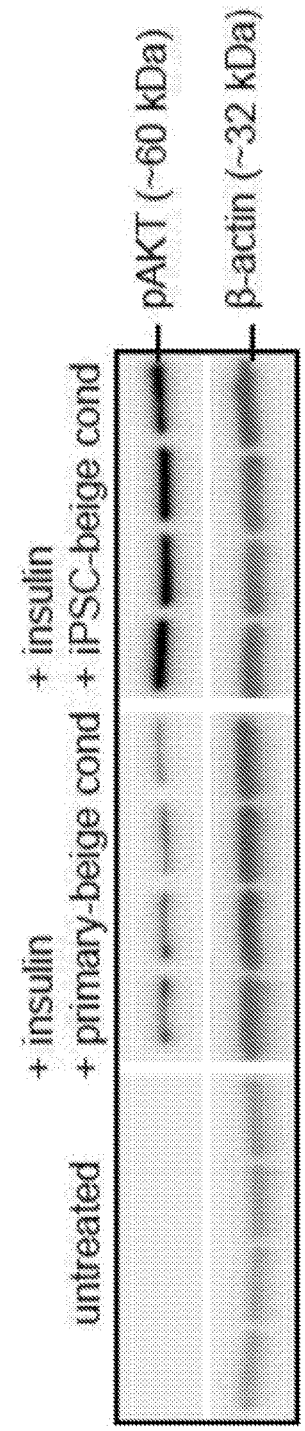
Figure 7D:
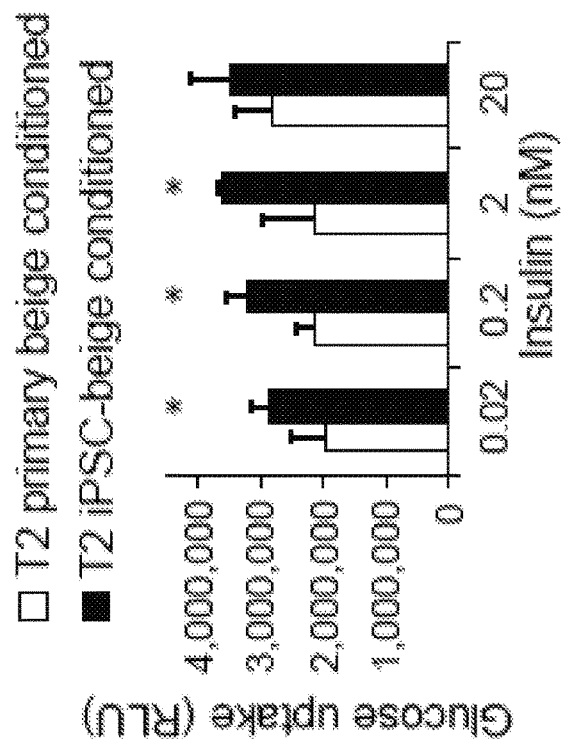
Figure 7C:
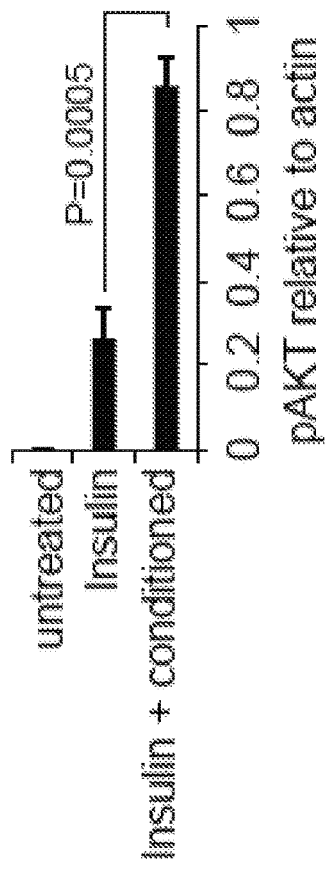
Figure 14A:
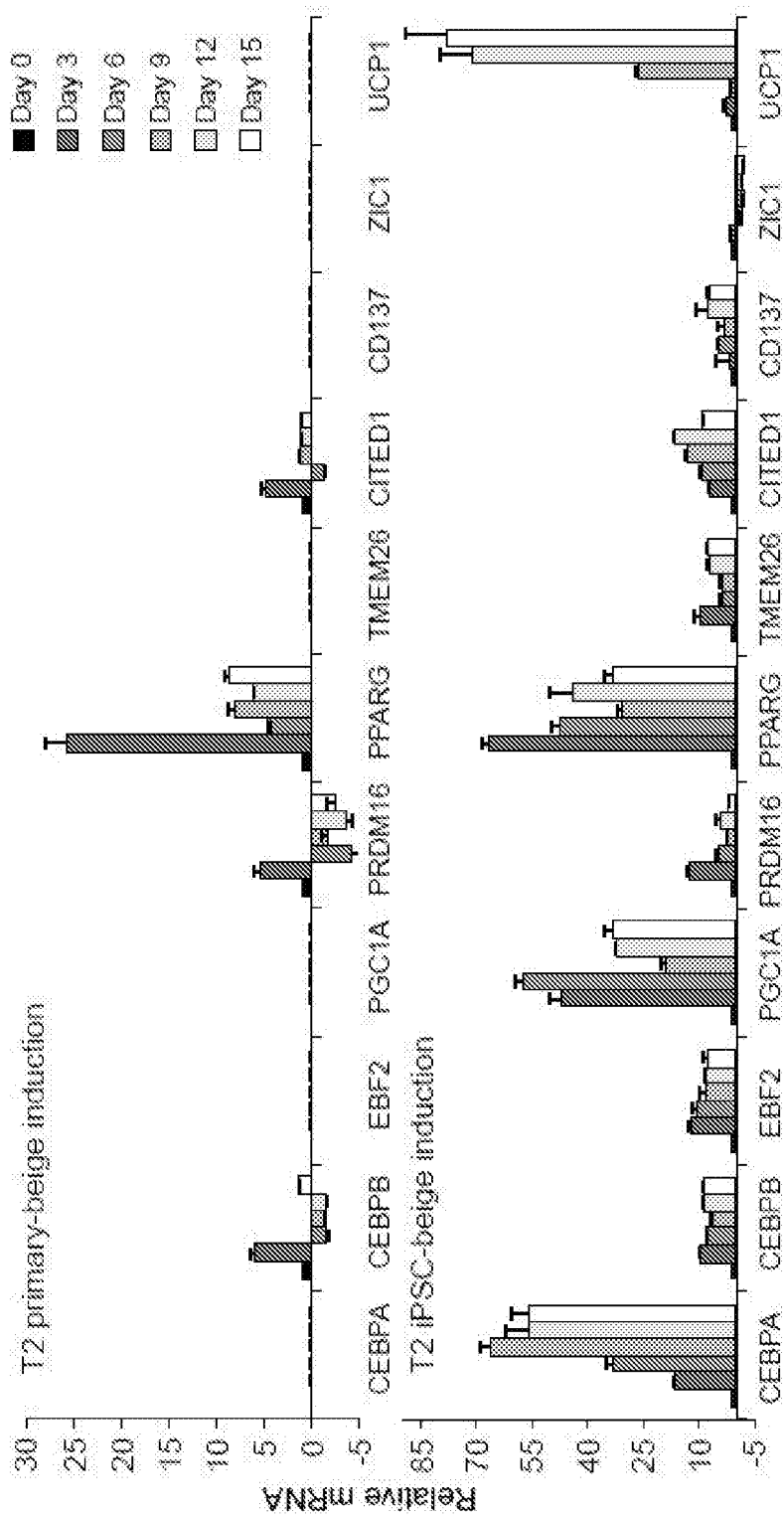
FIGS. 14A and 14B show generation of iPSC-beige adipocytes from type 2 diabetic adipogenic precursors (76 years old).
Figure 14B:
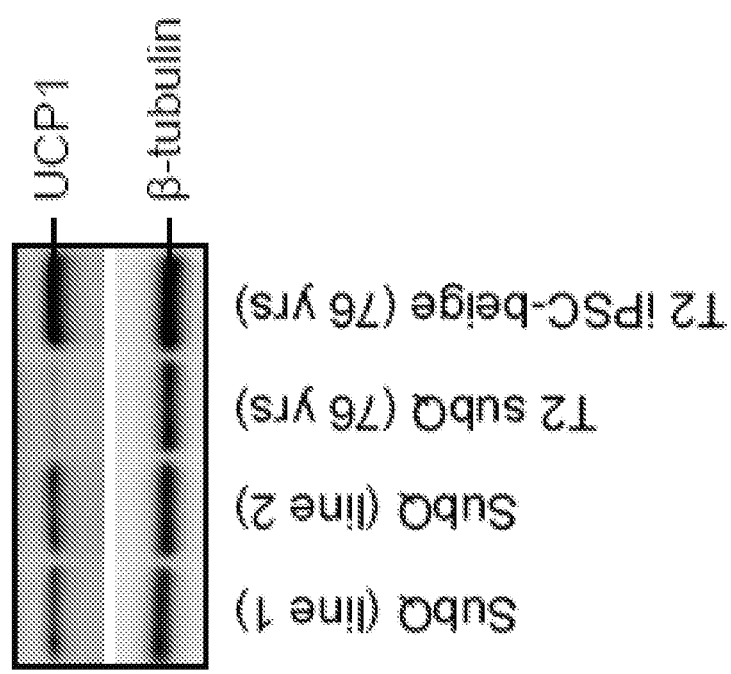
Figures 15A, 15B, 15C:
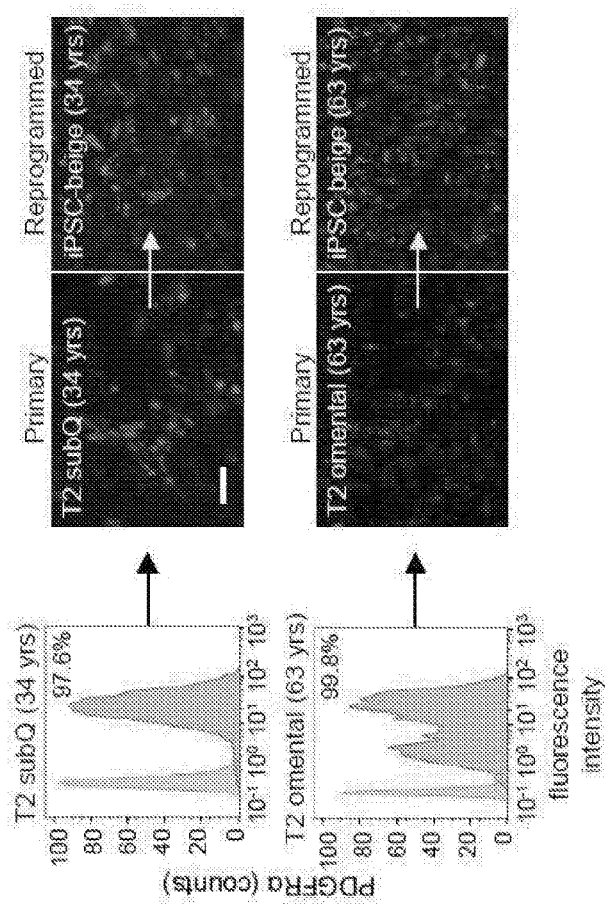
FIGS. 15A-15J show generation of iPSC-beige adipocytes from type 2 diabetic adipogenic precursors.
Figure 15F:
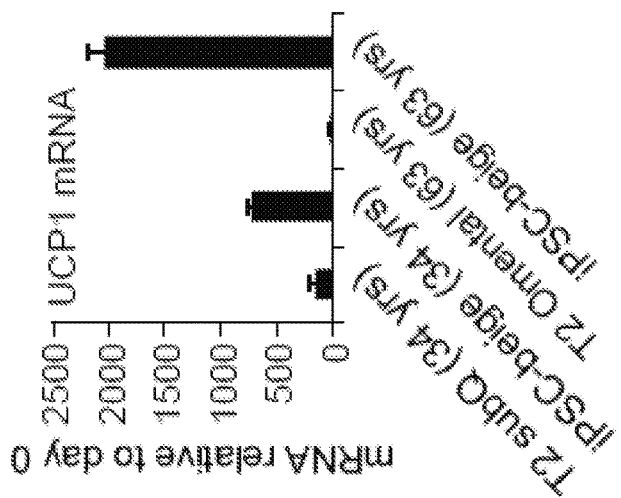
Figure 15E:
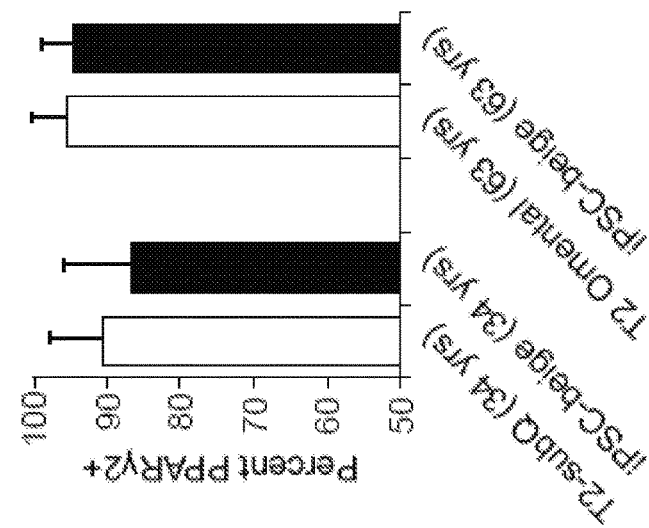
Figure 15D:
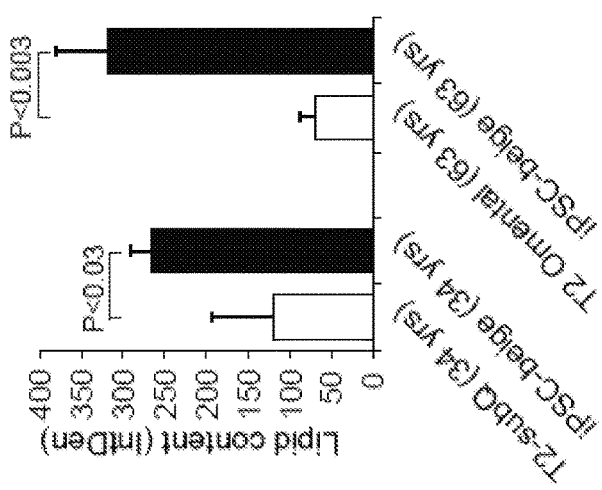
Figure 15H:
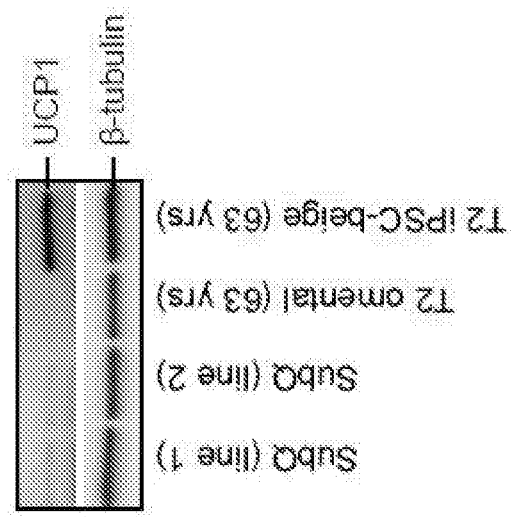
Figure 15G:
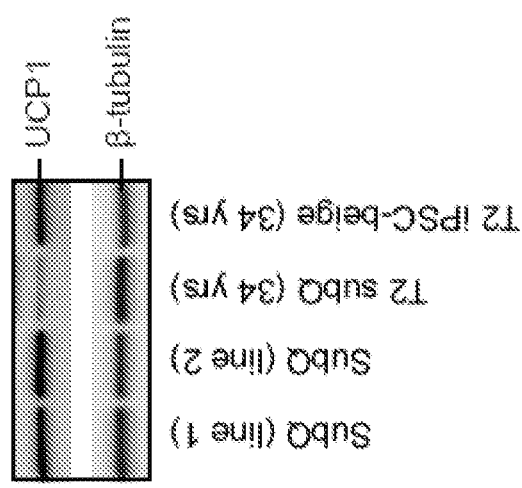
Figure 15J:
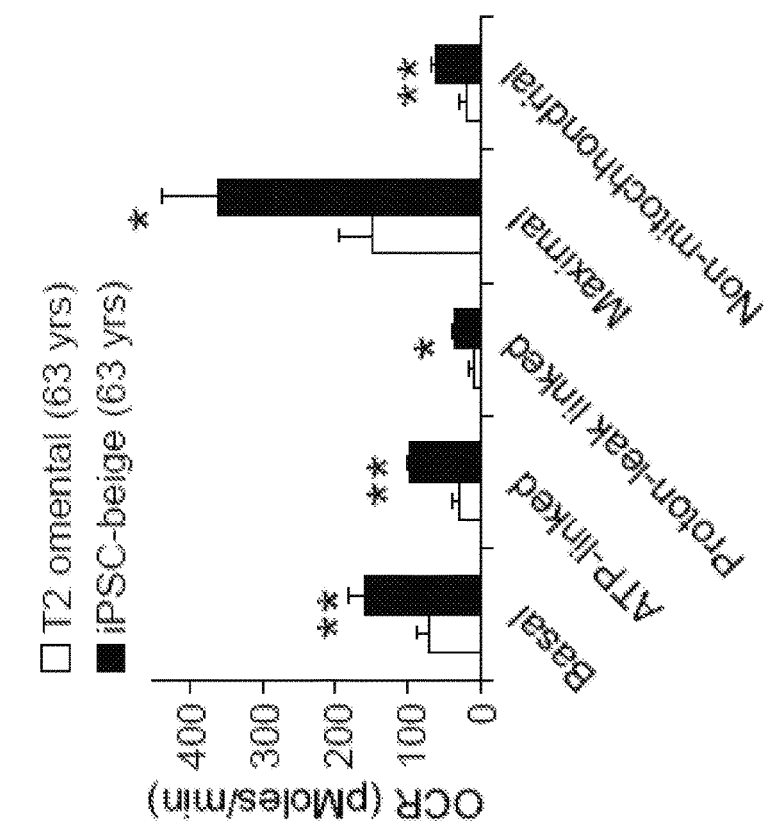
Figure 15I:
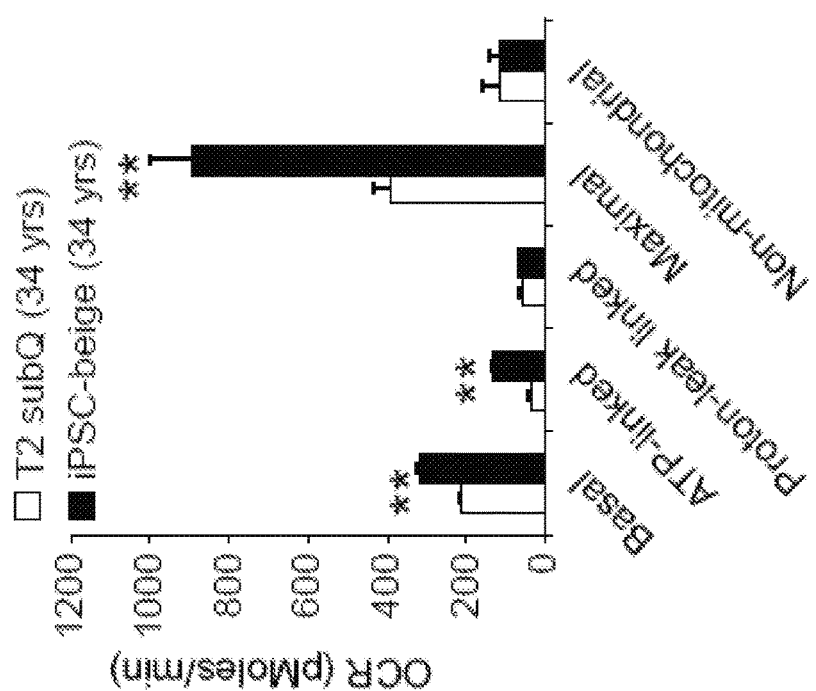

Compared to T2 primary-adipogenic precursors, T2 iPSC-adipogenic precursors displayed a similar expression of CD105, CD73, CD90, PDGFRβ, and PDGFRα. T2 iPSC-adipogenic precursors also displayed increased surface expression of the mural cell markers CD146 and NG2 and the adipogenic precursor marker MSCA1 (FIG. 6I). After beige induction of adipogenic precursors, T2 primary and iPSC-beige adipocytes both exhibited similar percentages of total PPARγ2 nuclear staining that were not significantly different from each other (FIGS. 6J and 6K). However, T2 iPSC-beige adipocytes displayed a >6-fold increase in lipid accumulation as compared to T2 primary adipocytes (FIGS. 6L and 6C). Upon differentiation, T2 primary-adipogenic precursors failed to display a transcriptional profile consistent with the formation of beige adipocytes, whereas their reprogrammed T2 iPSC-beige adipocyte counterparts displayed the full complement of beige adipogenic biomarkers (FIG. 14A). T2 iPSC-beige adipocytes also exhibit higher protein levels of UCP1, PLIN, and COX-IV and increased metabolic activity, including increased basal, ATP-linked, proton leak-linked, maximal, and non-mitochondrial respiration (FIG. 6E-6G). T2 iPSC-beige adipocytes also expressed comparable UCP1 protein expression to that of non-diabetic and young primary subcutaneous beige adipocytes (FIG. 14B). Similar results were observed with reprogrammed beige adipocytes that were generated from subcutaneous and omental fat depots of 34- and 63-year-old patients with T2 diabetes, respectively (FIG. 15A-15J), all donor characteristics summarized in FIG. 15A), including increased lipid droplet formation, elevated UCP1 expression, and increased metabolic activity (FIG. 15B-15H). To test whether T2 iPSC-beige adipocytes secrete anti-diabetic factors that can be used to increase insulin sensitivity, T2 subcutaneous primary adipocyte cultures from the 76-year-old patient were treated with T2 iPSC-beige adipocyte conditioned medium for 4 days before insulin challenge (FIG. 7A). Conditioned medium from T2 iPSC-beige adipocytes resulted in an approximately 3-fold increase in insulin sensitivity, as determined by phosphorylation of AKT, a downstream signaling component of insulin receptor signaling (FIGS. 7B and 7C). Furthermore, T2 iPSC-beige adipocyte conditioned medium treatment resulted in a significant increase in glucose uptake in the T2 primary adipocytes upon insulin challenge (FIG. 7D). Similar results were observed with subcutaneous primary adipocytes treated with conditioned medium from autologous iPSC-beige adipocytes generated from the 34-year-old T2 diabetes patient (FIG. 16A-16C).

Overall, these results indicate that adipogenic precursors with an inherently low beige adipogenic potential can be reprogrammed and differentiated with our method to produce iPSC-derived beige adipocytes with increased thermogenic and anti-diabetic potential.

Beige Adipocytes from a Larger Cohort of Patients

Beige adipocytes from a larger cohort of patents with metabolic dysfunction are tested to determine the overall efficacy of using this approach.

Methods

Cell Culture

PSCs were cultured in monolayer on hESC-qualified Matrigel-coated plates (Corning) and expanded in NutriStem hPSC XF Medium (Stemgent) and passaged with ReLeSR passaging reagent (STEMCELL Technologies). For mesoderm induction (Day 0), PSC colonies was dissociated with TrypLE cell dissociation reagent (Thermofisher) and plated on Matrigel coated plates in NutriStem medium containing 10 μM Y-27632 Rho kinase inhibitor (Calbiochem). The following day (Day 1), NutriStem medium was replaced with STEMdiff Mesoderm Induction Medium (MIM) (STEMCELL Technologies) and changed each day until day 5.

On day 5, MIM was replaced with MesenCult-ACF Medium (STEMCELL Technologies) and replaced each day until day 12. On day 12, cells were dissociated with 1 ml ACF Enzymatic Dissociation Solution (STEMCELL Technologies) and neutralized with 1 ml ACF Enzyme Inhibition Solution (STEMCELL Technologies). Cells were further suspended in 2 ml of PBS containing 2 mM EDTA and 0.5% BSA and centrifuged at 300 g for 5 minutes. Cells were re-suspended in MesenCult™-ACF Medium and passaged 1:2 to 6 well plates coated with MesenCult-ACF Attachment Substrate (STEMCELL Technologies). Culture medium was changed every day. After reaching 90% confluence, cells were passaged 1:2 until they were >95% positive for CD105, CD73, CD90, CD146 and PDGFRβ cell surface markers by flow cytometry (Days 20-30). After full maturation to the MSC phenotype, as determined by flow cytometry, cells were passaged at lower densities (1:4-1:6 split).

All assays were performed between 7 and 15 passages. For osteocyte differentiation, mature MSCs were grown in 24 well culture plates to 100% confluency in MesenCult-ACF and induced to differentiate in OsteoLife Complete Osteogenesis Medium (Lifeline Cell Technology) for 21 days prior to staining with Lifeline Alizarin Red Stain to visualize calcium deposition. For chondrocyte differentiation. For beige adipogenic precursor generation, cells were grown in 24 well culture plates to 90% confluence and treated with 5 uM SB413542 (Sigma) and 10 nM human IL-4 (Peprotech) for 2 days. For beige adipogenic induction, adipogenic precursors are differentiated for 3 days with adipogenic medium consisting of T3 (2 nM), insulin (170 nM), rosiglitazone (1 µM), SB413542 (5 uM), IBMX (0.5 mM), dexamethasone (5 µM) and indomethacin (125 µM) in EGM-2 medium (Lonza) supplemented with the BulletKit minus FGF2 (modified from[33]). Thereafter, cells are maintained in adipogenic medium without IBMX, dexamethasone and indomethacin. The medium was changed every 3 days and adipocytes were fully differentiated by 9-12 days as determined by lipid accumulation and peak expression of UCP1.

Medium Conditioning and Glucose Uptake

For conditioned medium experiments, mature adipocytes (day 12) were changed from adipogenic medium to high glucose DMEM (4500 g/L) supplemented with 2% FBS and 10 mM HEPES. During conditioning, cultures consisted of 50% fresh medium and 50% conditioned medium from either reprogrammed beige adipocytes or primary adipocyte cultures, which was replaced each day for 3 days. During the last 24 hours, conditioned medium was generated using serum-free high glucose DMEM (4500 g/L) supplemented with 0.5% BSA and 10 mM HEPES. One hour prior to sample harvest, cells were washed with PBS and medium was switched to no glucose and serum-free DMEM with insulin (0.02 to 20 nM) for 1 hour prior to sample harvest for glucose uptake analysis with the Glucose Uptake-Glo Assay Kit (Promega). Samples from 4 replicates per treatment were analyzed on a GloMax luminometer (Promega). Protein lysates were additionally harvested for western blot analysis and probed with an anti-phospho-AKT antibody (Cell Signaling Technology, #4060).

Oxygen Consumption Rate (OCR) Assay

FD-MSCs were cultured with Mesencult-ACF to confluence and differentiated in 24-well Seahorse V7 culture plates (Agilent Seahorse catalog #100777-004) with 100 µl of beige adipogenic medium for 15 days (see Methods, Cell Culture). Adipocyte cultures were assayed in XF DMEM (containing 2 mM glutamine, Agilent Seahorse catalog #102365-100) supplemented with 10 mM pyruvate and 25 mM glucose. OCR was measured with a Seahorse XF24 analyzer and addition of small molecule inhibitors were made through the injection ports. The following concentrations of the inhibitors were used: 1.25 µM oligomycin, 1 µM FCCP and 2 µM each of antimycin A and rotenone. Basal, uncoupled and maximal respiration rates were calculated upon subtraction of the non-mitochondrial oxygen consumption obtained at the end of each assay by the addition of antimycin A and rotenone. The values obtained were normalized to total µg protein per well as measured by BioRad Protein assay reagent (catalog #500-0114).

Primary Cells

All primary cell lines isolated from WAT were generated from outgrowth of the stromal vascular fraction and purchased from commercial vendors. All cell lines were validated to be at least 95% positive for adipogenic precursors as determined by flow cytometry for PDGFRα. Human white preadipocytes (HWP-c) cells, purchased from PromoCell (C-12730), were isolated from subcutaneous adipose tissue of a 27-year old Caucasian male with a BMI of 28. Normal human preadipocytes, purchased from Lonza (PT-5020), were isolated from subcutaneous adipose tissue of a 37 year old black female with a BMI of 21. Type 2 diabetic human preadipocytes, purchased from Lonza (PT-5022), were isolated from subcutaneous adipose tissue of a 76 year old black female with a BMI of 42.1. Type 2 diabetic human preadipocytes, purchased from Zenbio (OPD-F-3), were isolated from omental adipose tissue of a 63 year old white female with a BMI of 38.6. Type 2 diabetic human preadipocytes, purchased from Zenbio (SPD-F-3), were isolated from subcutaneous adipose tissue of a 34 year old black female with a BMI of 53.5. Cryopreserved cells were thawed and seeded in a 100×20 mm TC dish and treated as passage 0. Primary adipogenic precursors were expanded in DMEM containing 10% fetal bovine serum. Medium was changed daily and cells were cultured at 37° C. in a 5% $CO_2$ incubator. Upon 80% confluence, cells are split and passaged at a ratio of 1:6 (Passage 1). At 100% confluence, cells were induced to differentiate in beige adipogenic medium as was performed for generating FD-beige adipocytes.

Induced Pluripotent Stem Cell (iPSC) Lines

Integration-free iPSCs, purchased from Applied StemCell (ASE-9202), were derived from human skin fibroblasts. Integration free iPSCs, purchased from GIBCO (A18945), were derived from cord blood-derived CD34+ progenitors. Cryopreserved cells were thawed and seeded as a monolayer on hESC-qualified Matrigel-coated plates and treated as passage 0. iPSCs were expanded in NutriStem hPSC XF Medium and, upon reaching 80% confluence, were passaged with ReLeSR passaging reagent. Medium was changed daily and cells were cultured at 37° C. in a 5% $CO_2$ incubator. Cell lines were authenticated by confirming expression of Oct4, Sox2, SSEA4 and TRA-1-60.

Reprogrammed iPS Cell Lines

Integration- and xeno-free iPSCs were generated from urine-derived cells obtained from a de-identified 60-year old female patient (with patient informed consent) with no history of cancer through the Maine Medical Center BioBank via the MMC BioBank's IRB approved protocol (#2526). These cells were expanded and reprogrammed using the integration-free StemRNA-NM_Reprogramming kit and protocol for urine-derived cells following the manufacturers' instructions. iPSCs were also generated from passage 1 subcutaneous white adipose adipogenic precursors (Lonza PT-5022, Zenbio OPD-F-3, Zenbio SPD-F-3) using the StemRNA NM reprogramming kit following the manufacturers' instructions for the fibroblast protocol to generate integration- and xeno-free iPSCs. iPSCs generated in house were live cell-stained to evaluate pluripotency with anti-TRA-1-60-Vio488 Live Cell Stain following the manufacturers' instructions and imaged with an epifluorescence microscope (Leica).

Human Tissue

Human fetal interscapular brown adipose tissue (huFe iBAT) from 18-week gestation was obtained from the University of Pittsburgh Health Sciences Tissue Bank through an honest broker system after approval from the University of Pittsburgh Institutional Review Board (IRB number: 0702050) and in accordance with the University of Pittsburgh anatomical tissue procurement guidelines. Adipose tissue was dissociated using the Adipose Tissue Dissociation Kit enzyme digest cocktail. Isolated cells were seeded in a 100×20 mm dish in DMEM containing L-glutamine and 10% FBS for expansion. Medium was changed daily and cells were maintained at 37° C. in a 5% $CO_2$ incubator.

Generation of Chondrocytes

Figure 18:
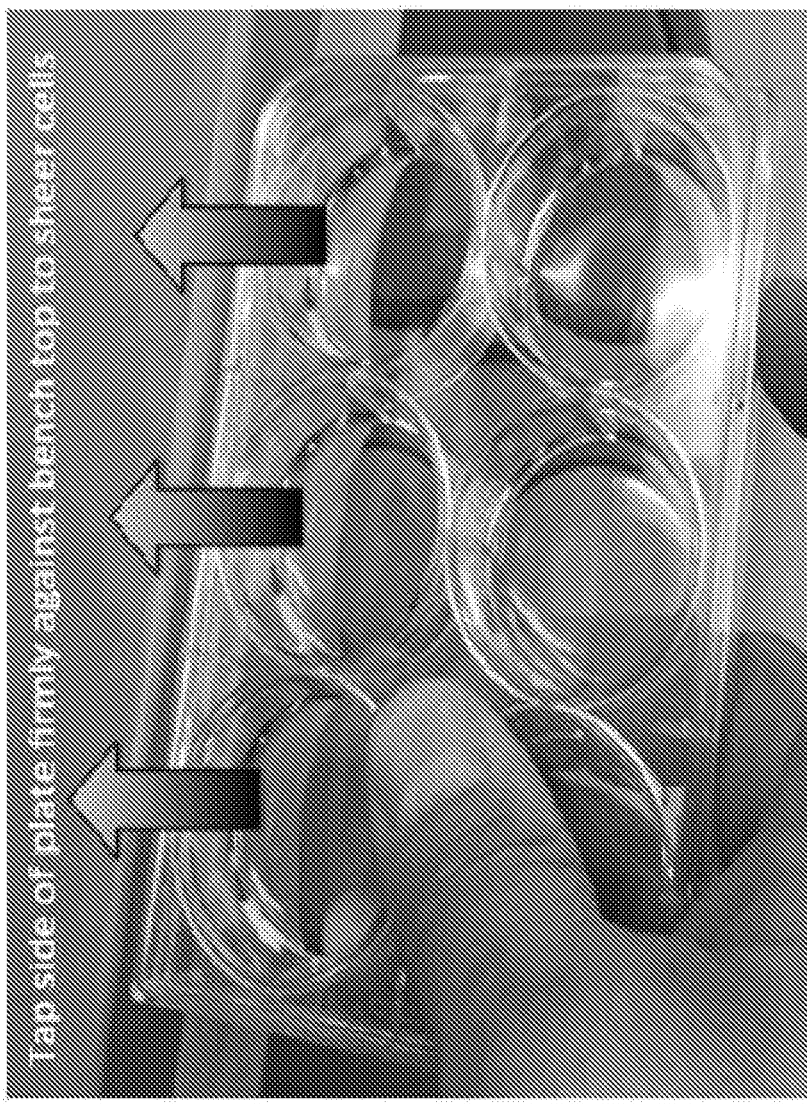
FIG. 18 depicts an image showing the strategy to release attached MSCs from culture plate.

1. Expand MSCs in a 6 well plate to 90% confluence. Conduct cell chondrocyte differentiation in a laminar flow cabinet.
2. Warm up cell wash buffer, ACF enzymatic dissociation solution, and Chondrogenesis Differentiation Medium to room temperature.
3. Aspirate MesenCult-ACF Plus medium from cell culture wells and wash once with PBS without calcium or magnesium. Remove PBS and replace with 500 mL/well ACF enzymatic dissociation solution.
4. Place cell culture plate in a 37° C. incubator for 5 minutes and tap side of plate firmly on hard surface several times to sheer cells from plate surface (FIG. 18). Check that cells have dislodged from the plate under a light microscope. If not, extend incubation time in 1-minute increments until noticeable detachment.
5. Add 500 mL of ACF enzymatic inhibition solution to each well of a 6 well plate. Further suspend cells in 2 mL of cell wash buffer and gently remove cells from the plate by washing with a pipette. Transfer cell suspension to a 15 mL centrifuge tube and centrifuge at 300 g for 5 minutes. Check for the appearance of a cell pellet at the bottom of the tube.
6. Remove the supernatant and re-suspend pelleted cells in 2 mL of Chondrogenesis Differentiation Medium. Centrifuge tube at 300 g for 5 minutes to pellet cells.

Generation of Osteoblasts
1. Prior to osteoblast differentiation, MSCs grown in well culture plates must be at 100% confluence. Conduct osteoblast differentiation in a laminar flow cabinet.
2. Aspirate MesenCult-ACF Plus medium and wash once with PBS without calcium or magnesium.
3. Remove PBS and replace with OsteoLife Complete Osteogenesis Medium in the following amounts based upon well size.
   96 well plate—100 ml/well
   24 well plate—500 ml/well
   6 well plate—2000 ml/well
4. Change 100% of the medium every 3 days for 21 days.

Isolation and Culture of Primary Preadipocytes
Recipe for Differentiation Mediums

TABLE 1

Beige adipocyte induction medium:

| Factor | stock concentration | working concentration | for 10 ml pf medium |
|---|---|---|---|
| DMEM | 1X | 1X | 9 ml |
| FBS | 10X | 1X | 1 ml |
| Insulin | (10 μg/ml = 1.7 mM) | 170 nM | 1 μl |
| T3 | 1 μM | 2 nM | 20 μl |
| Rosiglitazone | 5 mM | 1 μM | 2 μl |
| SB | 10 mM | 5 μM | 5 μl |
| IBMX | 500 mM | 0.5 μM | 10 μl |
| Dexamethasone | 5 mM | 5 μM | 10 μl |
| Indomethacin | 125 mM | 125 μM | 10 μl |
| AA2P | 50 mg/ml | 50 μg/ml | 10 μl |

TABLE 2

Beige adipocyte maintenance medium:

| Factor | stock concentration | working concentration | for 10 ml pf medium |
|---|---|---|---|
| DMEM | 1X | 1X | 9 ml |
| FBS | 10X | 1X | 1 ml |
| Insulin | 1.7 mM | 170 nM | 1 μl |
| T3 | 1 μM | 2 nM | 20 μl |
| Rosiglitazone | 5 mM | 1 μM | 2 μl |
| SB | 10 mM | 5 μM | 5 μl |
| AA2P | 50 mg/ml | 50 μg/ml | 10 μl |

Cell Isolation, Expansion and Differentiation of Interscapular Brown Adipose Tissue Preadipocytes
1. Prior to adipose cell isolation, warm DMEM, FBS and cell wash buffer to room temperature.
2. In a laminar flow cabinet for cell culture, place 5 g of adipose tissue on a 100×20 mm dish. Suspend tissue in 1 mL of Adipose Tissue Dissociation Kit enzyme digest cocktail and finely mince with a razorblade.
3. Transfer cell suspension slurry to a 5 mL polystyrene round bottom tube and add an additional 1.5 mL of enzyme digest cocktail to tube.
4. Incubate tube at 37° C. on a rotating nutator for 30 minutes. During incubation period, briefly vortex sample for 5 s in 10-minute intervals.
5. Transfer cells to a 15 mL tube and add 5 mL of DMEM. Filter cell suspension through a 100 μm strainer into a new 15 mL tube and centrifuge at 300 g for 5 minutes to form a pellet.
6. Remove supernatant and leave behind <100 mL of DMEM. Resuspend cell pellet in 10 mL of DMEM containing 10% FBS and plate in a 100×20 mm dish for expansion. Agitate plate to spread cells evenly on well surface and incubate plate at 37° C. in a 5% CO$_2$ incubator undisturbed. Change 100% of medium every day.
7. Upon 80% confluence, split and passage cells at a ratio of 1:6.
8. Prepare for passage by warming cell wash buffer and cell culture medium (DMEM containing 10% FBS) to room temperature. Warm TrypLE dissociation reagent to 37° C.
9. Aspirate cell culture medium from wells and wash once with PBS. Remove PBS and add 500 μL of pre-warmed TrypLE reagent to each well of a 6 well plate. Scale TrypLE amount for larger tissue culture plates accordingly.
10. Incubate culture plate at 37° C. for 5 minutes. Check that most cells have been dislodged from the plate surface with a light microscope. If not, extend incubation time in 1-minute increments until noticeable cell detachment.
11. Add cell wash buffer to each well and gently re-suspend cells from the plate by washing with a pipette. Check that most cells have been dislodged from the plate with a light microscope. If not, pipette up and down as needed.
12. Transfer cells to an appropriate tube and centrifuge at 300 g for 5 minutes. Check for the appearance of a cell pellet at the bottom of the tube.
13. Remove the supernatant and re-suspend cells in an appropriate amount of DMEM containing 10% FBS. Plate cells at a ratio of 1:6 by adding 2 mL of cell suspension to each well of a 6 well plate. Agitate to spread cells evenly on well surface. Incubate plate at 37° C. in a 5% CO$_2$ incubator undisturbed. Change 100% of medium every 2 days.
14. Differentiation can be performed when cells reach 100% confluence.
15. Aspirate DMEM containing 10% FBS and wash once with PBS. Remove PBS and replace with beige adipocyte induction medium in the following amounts based upon well size.
    96 well plates—150 ml/well
    24 well plates—1000 ml/well
    6 well plates—3000 ml/well
16. After 72 hours of induction treatment, aspirate beige adipocyte induction medium from wells and replace with beige adipocyte maintenance medium in the following amounts based upon well size.
    96 well plates—150 ml/well
    24 well plates—1000 ml/well
    6 well plates—3000 ml/well 17. Change 100% of beige adipocyte maintenance medium every 48 hours for 4 days. Note: huFe iBAT-derived beige adipocytes often times reach full maturity following only 7 days of differentiation.

Cell Expansion and Differentiation of Commercial Preadipocytes Isolated from Subcutaneous or Omental Adipose Tissue 1. Thaw and plate preadipocytes isolated from subcutaneous or omental adipose tissue following the manufacturers' recommendations in a laminar flow cabinet for cell culture.
2. Upon 80% confluence, split and passage cells at a ratio of 1:6 (see Cell isolation, expansion and differentiation of interscapular BAT preadipocytes above).
3. Differentiation can be performed when cells reach 100% confluence (see Cell isolation, expansion and differentiation of interscapular BAT preadipocytes above).
4. Change 100% of beige adipocyte maintenance medium every 72 hours for 9 days. Note: commercial preadipocytes-derived beige adipocytes often reach full maturity between 9 and 12 days of differentiation.

Medium Conditioning and Glucose Uptake
Conditioning Medium

1. Prior to conditioned medium experiments, iPSC-derived beige adipocytes and type 2 diabetic subcutaneous adipocytes must be differentiated to full maturity (day 12) (see Generation of beige adipocytes and Culture differentiation of commercial preadipocytes isolated from subcutaneous or omental adipose tissue above). Differentiate iPSC-derived beige adipocytes in 24 well plates (experimental medium conditioning) and type 2 diabetic subcutaneous adipocytes in both 24 well plates (control medium conditioning) and 96 well plates (for glucose uptake).
2. Use iPSC-derived beige adipocytes and type 2 diabetic adipocytes in 24 well plates to generate conditioned medium. Aspirate beige maintenance medium from wells of 24-well plates and wash once with PBS without calcium or magnesium. Remove PBS and replace with 500 mL of high glucose DMEM (4500 mg/l) supplemented with 2% FBS and 10 mM HEPES per well. Allow medium to be conditioned for 24 hours prior to use.
3. Time 0: After 24 hours collect conditioned medium from 24 well plates and replace with 500 µl fresh medium. Prior to use, centrifuge conditioned medium at 300 g for 5 minutes and then transfer supernatant to new tubes. To condition type 2 diabetic subcutaneous adipocytes with conditioned medium, remove medium from wells of 96 well plate and wash once with PBS. Remove PBS and replace with 100 mL of a 50/50 mixture of fresh medium and conditioned medium per well (iPSC-beige or type diabetic for controls). Fresh medium consists of high glucose DMEM (4500 mg/l) supplemented with 2% FBS and 10 mM HEPES.
4. Time 24 hours: Repeat step 3 above.
5. Time 48 hours: Repeat step 3 above, but replace fresh medium on 24 well plates with 500 µl DMEM (4500 mg/l) supplemented with 0.5% BSA and 10 mM HEPES per well for conditioning.
6. Time 72 hours. Remove 100% of medium from 96 well plates and replace with 100 mL of 50% conditioned medium and 50% DMEM (4500 mg/l) supplemented with 0.5% BSA and 10 mM HEPES per well. In this way, medium conditioning for the last 24 hours will be FBS free.

Glucose Uptake

1. Time 96 hours: Remove 100% of medium and wash once with PBS. Remove PBS and replace with no glucose and serum-free DMEM with insulin (0.02 to 20 nM with four replicates each) for one hour prior to glucose uptake tests.
2. Glucose uptake analysis was performed using the Glucose Uptake-Glo Assay Kit and analyzed on a GloMax luminometer following the manufacturer's instructions.

Medium Conditioning and Phospho-AKT Assay

1. Repeat exactly as for glucose uptake assay, but with type 2 diabetic cells grown in 24 well-plate for protein harvest with a 50/50 mixture of fresh medium (250 ml) and conditioned medium (250 ml) per well. At 96 hours, treat with 20 nM insulin for 10 minutes and harvest cells 80 mL RIPA buffer with protease and phosphatase inhibitor cocktail to each well. Dislodge the cells by gently scrapping and washing the surface of the wells with a 200 mL pipet tip. Transfer protein lysate to 1.7 mL eppendorf tubes and centrifuge at 14,000 rpm for 5 minutes to pellet cell debris.
2. Run samples through a western blot analysis using an anti-phospho-AKT antibody (see protein extraction and immunoblotting for western blot)

Oxygen Consumption Rate Assay
Assay Preparation

1. Expand and culture FD-MSCs to confluence and plate in a 24-well Seahorse V7 culture plate (see Generation of mesenchymal stem cells above).
2. Once FD-MSCs are 90% confluence, differentiate with 100 ml of beige adipogenic medium for 14 days (see Generation of beige adipocytes above).
3. Prior to OCR assay, aspirate beige maintenance medium and replace with 180 ml of Seahorse XF assay medium (containing 2 mM glutamine) supplemented with 10 mM pyruvate and 25 mM glucose.

Conducting Assay and Analyzing Results

1. With a Seahorse XF24 analyzer, measure OCR with small molecule inhibitors added through the injection ports. The following concentrations of the inhibitors were used: 1.25 mM oligomycin, 1 mM FCCP and 2 mM each of antimycin A and rotenone.
2. Basal, uncoupled and maximal respiration rates can be calculated upon subtraction of the non-mitochondrial oxygen consumption obtained at the end of each assay by the addition of antimycin A and rotenone. The values obtained can be normalized to total mg protein per well as measured by BioRad Protein assay reagent. Note: For β3-adrenergic response assay, remove rosiglitazone from maintenance medium at day 12 and culture adipocytes for an additional 4 days to whiten. Treat cells with CL316,243 (1 mM) for 4 hours prior to Seahorse XF analysis.

Flow Cytometry
Cell Preparation

1. Prior to antibody staining, cells must be dissociated from cell culture plates and pelleted in cell wash buffer (see 1.4: Cell passaging and 2.5: Generation of mesenchymal stem cells above).
2. In a laminar flow cabinet, remove supernatant and re-suspend cells in an appropriate amount of cell wash buffer. For example, when staining with 3 PE/APC pairs, re-suspend cell pellet from one well of a 24 well plate in 100 mL of cell wash buffer and split suspension into 4 microcentrifuge tubes, 25 mL each. Label tubes with their respective PE/APC antibody pairs. Separate one tube as an unstained control.
3. Dilute primary conjugated antibodies 1:10 for staining. Mix cell suspension by gently pipetting. Allow cells to stain undisturbed at 4° C. for 15 minutes in the dark.
4. Following 15 minutes, add 900 mL of cell wash buffer to each sample tube and centrifuge at 300 g for 5 minutes to pellet cells.
5. Gently remove supernatant and leave behind cell pellet. Resuspend cell in 250 mL of cell wash buffer and transfer to a 5 mL Polystyrene round-bottom tube for flow cytometry analysis and quantification with MACSQuantify.
6. For TGFBR1 and TGFBR2, fix cells with paraformaldehyde for 10 minutes and permeabilize with methanol for 30 minutes on ice prior to staining. To stain, dilute antibodies 1:10 in 25 mL cell wash buffer for 30 minutes at 4° C.

Immuno- and BODIPY Staining
BODIPY Staining
1. Prior to staining, expand and grow adipocytes to full maturity (day 12) (see Generation of beige adipocytes and Cell expansion and differentiation of commercial preadipocytes isolated from subcutaneous or omental adipose tissue above).
2. Remove culture medium and stain cells with BODIPY diluted 1:2000 in fresh culture medium for 30 minutes at 37° C.
3. Following 30 minutes, remove culture medium with BODIPY and gently wash once with PBS. Remove PBS and replace with fresh cell culture medium prior to imaging on an EVOS Fluorescence Microscope.
4. Quantitate lipid accumulation via the integrated density function with ImageJ software.

Immunofluorescence Staining
1. Prior to staining, expand and grow beige adipocytes to full maturity (day 12) (see Generation of beige adipocytes and Cell expansion and differentiation of commercial preadipocytes isolated from subcutaneous or omental adipose tissue above).
2. Wash cells with PBS and fix cells for 10 minutes by gently pipetting 4% paraformaldehyde down the side of the wells.
3. After 10 minutes, remove paraformaldehyde and wash once with PBS. Remove PBS and permeabilize cells with 0.3% Triton X-100 in PBS for 15 minutes at room temperature.
4. After 15 minutes, remove 0.3% Triton X-100 in PBS and add blocking buffer (10% donkey serum diluted in PBS) for 1 hour at room temperature.
5. Remove blocking buffer and stain with the following primary antibodies diluted 1:100 in blocking buffer for 24 hours at 4° C.: anti-FOXF1, anti-SMA, anti-SM22 alpha, anti-COX-IV, anti-UCP1, anti-PLIN, and anti-EBF2. To avoid evaporation, wrap plate in parafilm during the 24 hour period.
6. After 24 hours, remove antibodies in blocking buffer and gently wash wells 3 times with PBS.
7. Prepare appropriate secondary antibodies diluted 1:200 in blocking buffer and add to wells. Allow plate to sit undisturbed for 1 hour at room temperature in the dark.
8. Remove secondary antibodies in blocking buffer and wash wells 3 times with PBS. Remove and replace with fresh PBS prior to imaging with an epifluorescence microscope (Leica).

Quantitative PCR
Sample Preparation
1. Aspirate medium from wells and add RLT lysis buffer as provided by RNeasy Micro Kit. Gently scrape and wash wells with the RLT lysis buffer using an appropriately sized pipette.
2. Transfer cell lysate to a microcentrifuge tube. If not immediately used, cell lysate can be stored at −70° C.
3. Complete manual or automated RNA extraction procedure according to manufacturers' instructions.
4. Generate cDNA from 250 ng of RNA with qScript cDNA SuperMix.
5. For qPCR, amplify gene-specific cDNA transcripts in triplicate with iQ SYBR Green Supermix in a CFX384 Touch Real-Time PCR Detection System.
6. Normalize data to b-actin expression using the DDCT method. Fold changes will be relative to the vehicle control.

JC-1 Assay
Assay Preparation
1. Prepare a 2 mM working solution of JC-1 dye by diluting stock solution in HBSS with 20 mM HEPES buffer. Heat solution on a rotating nutator in a 37° C. incubator to facilitate dissolution. Conduct JC-1 assay preparation in a laminar flow cabinet for cell culture.
2. Aspirate medium from cell cultures and add JC-1 dye solution. Incubate in a 37° C., 5% CO2 incubator for 30 minutes.
3. Remove and replace working solution with HBSS prior to imaging. Image for fluorescence change at Ex/Em=490/525 nm and 540/595 nm with an epifluorescence microscope.
4. Calculate subsequent ratio analysis from images using ImageJ software.

Mass Spectrometry
Preparation
1. Prior to preparation, expand and grow beige or brown adipocytes to full maturity in a monolayer culture in 6 well plates (day 12) (see Generation of beige adipocytes and Cell expansion and differentiation of commercial preadipocytes isolated from subcutaneous or omental adipose tissue above).
2. Dissociate cells from plate with 0.5 mM EDTA solution, pellet, and extract cells using the Qproteome Mammalian Protein Prep Kit according to manufacturers' instructions.

Additionally, add two magnetic beads and homogenize sample with an Autodisruptor at maximum speed for 60 s during the cell lysis step.

3. Digest protein samples by adding trypsin as provided by the ProteoExtract digestion kit.
4. Separate peptides with an Ultimate RSLC system 3000 nanoscale liquid chromatograph and then infuse onto a 5600 TripleTOF mass spectrometer.
5. Profile protein samples using the SWATH data-independent acquisition method.
6. Spectra processing and database searching of an ion library consisting of 4091 proteins was performed with ProteinPilot software (Sciex). SWATH runs were extracted and analyzed using PeakView software and MarkerView software was utilized to find statistically relevant relationships through t test comparisons.

Protein Extraction and Immunoblotting
Protein Extraction
1. Aspirate cell culture medium and add RIPA buffer supplemented with Halt Protease & Phosphatase Inhibitor Cocktail according to manufacturers' instructions.
2. Gently scrape well surface while washing with lysis buffer with an appropriately sized pipette. Transfer cell suspension to 1.7 mL Eppendorf tubes and centrifuge at 15,000 rpm for 5 minutes to pellet cells. Collect the supernatant to new Eppendorf tubes.
3. Determine protein concentration using the Pierce BCA Protein Assay Kit following manufacturers' instructions.

Immunoblotting
1. Denature protein lysates by heating at 90° C. for 5 min
2. Separate protein with a Criterion™ TGX gels and then transfer onto PVDF membranes.
3. Incubate membrane in 1× Detector Block Solution for 1 hour at room temperature or overnight at 4° C. Following 1 hour, add primary antibodies diluted at a ratio of 1:1000~2000 in TBS with Tween 20 and 0.2× Detector Block Solution and incubate overnight at 4° C.
4. Remove solution and wash 3 times with TBS with Tween 20 (5 minutes per wash).
Following washes, add secondary antibody diluted at a ratio of 1:1200 and incubate 2 hours at room temperature.
5. Remove secondary antibody solution and wash 3 times with TBS with Tween 20 (5 minutes per wash).
6. Develop membrane with Clarity™ Western ECL Substrate and detect using a Bio-Rad ChemiDoc Touch Imaging System.
7. Quantitation of protein was performed using Image Lab software (Bio-Rad).

Fatty Acid Uptake Assay
Preparation
1. Expand and grow iPSC-beige and whitened iPSC-beige adipocytes to full maturity in a 96 well plate (day 12) (see Generation of beige adipocytes above). To whiten iPSC-beige adipocytes for this assay, induce iPSC-MSCs for three days in the induction cocktail as described in the differentiation protocol (see Generation of beige adipocytes above). Following three days of induction, replace beige induction medium with DMEM containing 10% FBS and insulin (1.7 mM). Change 100% of medium every 3 days until full maturity (day 12).
2. On day 12, replace culture medium with DMEM containing 10% FBS. Change 100% of medium every 2 days for 6 days.
3. Following 6 days of rest, remove culture medium and replace with 90 ml of serum free DMEM containing 0.2% BSA. Incubate the plate at 37° C. in a 5% CO2 incubator for 1 hour.
4. After 1 hour, add CL316,243 (1 mM) to designated wells. Allow cells to incubate for 2 hours.
5. Prepare loading buffer according to manufacturers' instructions. Following 2 hours of incubation, add 100 ml of 1× loading buffer and immediately analyze with Flexstation 3 (Molecular devices).
6. Analyze data with SoftMax Pro 7 software continuously for two hours. Set software to record points in 30 s intervals.

Quantification and Statistical Analysis
P values were calculated in Microsoft Excel and derived using a two-tailed homo- or heteroscedastic Student's t test, which can be found in the individual figure panels and figure legends. In the case of multiple comparisons, Bonferroni correction was used to adjust P values after one-way ANOVA analysis. Significance was defined as p<0.05. Cell culture experiments were performed with an n≥3 and are indicated in the figure legends in the case of immunofluorescence quantitations. Error bars in graphs are defined in the figure legends and represent the mean±SD (standard deviation). The mean±SEM (standard error of mean), which reflects the variability of the mean values, was used in cases where experimental readings were repeated a large number of times (ex. Fatty Acid Uptake assay).

TABLE 3

Oligonucleotide sequences used for qPCR in the study, Related to STAR Methods
Oligonucleotides

| Gene | Forward (5' to 3') | Reverse (5' to 3') |
| --- | --- | --- |
| UCP1 | AGTTCCTCACCGCAGGGAAAGA | GTAGCGAGGTTTGATTCCGTGG |
| CEBPA | AGGAGGATGAAGCCAAGCAGCT | AGTGCGCGATCTGGAACTGCAG |
| CEBPB | AGAAGACCGTGGACAAGCACAG | CTCCAGGACCTTGTGCTGCGT |
| EBF2 | GAGCAAGAAGGCTTGACCCATC | CCAAACACAACCTGGAGACCATC |
| PGC1α | CCAAAGGATGCGCTCTCGTTCA | CGGTGTCTGTAGTGGCTTGACT |
| PRDM16 | CAGCCAATCTCACCAGACACCT | GTGGCACTTGAAAGGCTTCTCC |
| PPARγ | CGAGGACACCGGAGAGGG | TGTGGTTTAGTGTTGGCTTCTT |
| TMEM26 | GCAGTTTCCACTTGACCTGGCA | GAAGACGCTGATTCCGATGTTCC |
| CITED1 | CCACTAGCTCCTCTGGATCG | AGCCCCTTGGTACTGGCTAT |
| CD137 | TCTTCCTCACGCTCCGTTTCTC | TGGAAATCGGCAGCTACAGCCA |
| ZIC1 | GATGTGCGACAAGTCCTACACG | TGGAGGATTCGTAGCCAGAGCT |
| PDGFRα | GACTTTCGCCAAAGTGGAGGAG | AGCCACCGTGAGTTCAGAACGC |

TABLE 3-continued

Oligonucleotide sequences used for qPCR in the study, Related to STAR Methods
Oligonucleotides

| Gene | Forward (5' to 3') | Reverse (5' to 3') |
|---|---|---|
| PPARγ1 | CGAGGACACCGGAGAGGG | TGTGGTTTAGTGTTGGCTTCTT |
| PPARγ2 | TTTTAACGGATTGATCTTTTGC | AGGAGTGGGAGTGGTCTTCC |
| PPARγ3 | TTCTGCTTAATTCCCTTTCC | AGGAGTGGGAGTGGTCTTCC |
| BAPX1 | CCGCTTCCAAAGACCTAGAGGA | ACCGTCGTCCTCGGTCCTTGG |
| HOX11 | TGTGCCAGGCTCTTCTGGAAGG | CTCCGCACCTGCTGGGACTTC |
| FOXF1 | AGCAGCCGTATCTGCACCAGAA | CTCCTTTCGGTCACACATGCTG |
| IRX3 | CTCCGCACCTGCTGGGACTTC | CTCCACTTCCAAGGCACTACAG |
| T (brachyury) | CCTTCAGCAAAGTCAAGCTCACC | TGAACTGGGTCTCAGGGAAGCA |
| MIXL1 | CCCGACATCCACTTGCGCGAG | GGAAGGATTTCCCACTCTGACG |
| SOX1 | GAGTGGAAGGTCATGTCCGAGG | CCTTCTTGAGCAGCGTCTTGGT |
| SOX17 | ACGCTTTCATGGTGTGGGCTAAG | GTCAGCGCCTTCCACGACTTG |
| VEGFR2 | GGAACCTCACTATCCGCAGAGT | CCAAGTTCGTCTTTTCCTGGGC |
| OSR1 | CCTACACCTGTGACATCTGCCA | GTGAGTGTAGCGTCTTGTGGAC |
| ACTA1 | AGGTCATCACCATCGGCAACGA | GCTGTTGTAGGTGGTCTCGTGA |
| αSMA | CTATGCCTCTGGACGCACAACT | CAGATCCAGACGCATGATGGCA |
| SM22α | TCCAGGTCTGGCTGAAGAATGG | CTGCTCCATCTGCTTGAAGACC |
| TGFβ1 | TACCTGAACCCGTGTTGCTCTC | GTTGCTGAGGTATCGCCAGGAA |
| TGFβ2 | AAGAAGCGTGCTTTGGATGCGG | ATGCTCCAGCACAGAAGTTGGC |
| TGFβ3 | CTAAGCGGAATGAGCAGAGGATC | TCTCAACAGCCACTCACGCACA |
| TGFβR1 | GACAACGTCAGGTTCTGGCTCA | CCGCCACTTTCCTCTCCAAACT |
| TGFβR2 | GTCTGTGGATGACCTGGCTAAC | GACATCGGTCTGCTTGAAGGAC |
| FGF21 | CTGCAGCTGAAAGCCTTGAAGC | GTATCCGTCCTCAAGAAGCAGC |
| NRG4 | TGTGGCATTGGCGGTCCTAGTA | ACTGCTCGTCTCTACCAGGTTG |
| IL6 | AGACAGCCACTCACCTCTTCAG | TTCTGCCAGTGCCTCTTTGCTG |
| ADIPOQ | CAGGCCGTGATGGCAGAGATG | GGTTTCACCGATGTCTCCCTTAG |

Culture of iPSCs, Mesoderm Induction, Generation of iPSC-Derived MSCs and Differentiation of MSCs into Beige Adipocytes. Related to Methods Details in the STAR Methods.

Culture of iPSCs
Cell Plating and Culture
1. Thaw ES cell qualified Matrigel on ice, dilute 1:25 in cold RPMI and coat plates prior to cell seeding. Coat each well of a 6 well plate with 1 ml of Matrigel. Distribute the Matrigel over the entire surface of the well and allow plate to sit covered and undisturbed in a laminar flow cabinet for cell culture for at least 1 hour.
2. Prior to cell plating, remove Matrigel from wells using a sterile pipette tip connected to a vacuum aspirator. Immediately wash well surface with PBS without calcium or magnesium. Aspirate PBS and add desired volume of cell colonies suspended in 2 ml of NutriStem hPSC XF Medium containing 10 µM Y-27632 Rho-kinase inhibitor to each well. Agitate plate to spread cell colonies evenly on well surface. Incubate plate at 37° C. in a 5% $CO_2$ incubator for expansion.

Note: Only use Y-27632 stock solutions that have been resuspended in DMSO. We have found that water based versions lose significant inhibitor activity. Conduct Mesoderm induction of iPSC in a laminar flow cabinet.

3. Expand cells in NutriStem hPSC XF Medium overnight and change 100% of the medium without Y-27632 every 24 hours in a laminar flow cabinet for cell culture. When changing media, tilt plate up and allow media to pool at the bottom of wells. Aspirate the pooled medium without touching the surface of the plate. Replace with medium warmed to room temperature by pipetting 2 ml down the side of the wells.

Cell Passaging
1. Expand cell colonies until they have reached 70-80% confluence in high-density areas of the wells. High-density accumulation can occur along the edges of the well as well as the middle. Cells permitted to reach high density will lose their potential for differentiation after multiple passages.
2. Prior to cell passage, warm cell wash buffer and NutriStem hPSC XF Medium to room temperature. Conduct cell passage in a laminar flow cabinet.
3. Aspirate NutriStem hPSC XF Medium from wells with vacuum aspirator and wash with PBS without calcium or magnesium. Remove PBS and add 1 ml of ReLeSR reagent to side of well. Agitate plate to allow ReLeSR reagent to spread evenly on the surface.
4. Aspirate ReLeSR reagent with vacuum aspirator after 30 seconds, which will leave behind a thin film of liquid. Incubate plate at 37° C. for 5-8 minutes undisturbed.
5. Add fresh NutriStem hPSC XF Medium to wells and gently remove the cell colonies from the plate. Check that most cells have been dislodged from the plate surface with a light microscope. If not, rewash with more medium as needed.
6. Transfer cell colony suspension in NutriStem hPSC XF Medium to Matrigel coated culture plates for further expansion (see Cell plating and culture above).

Figure 17:
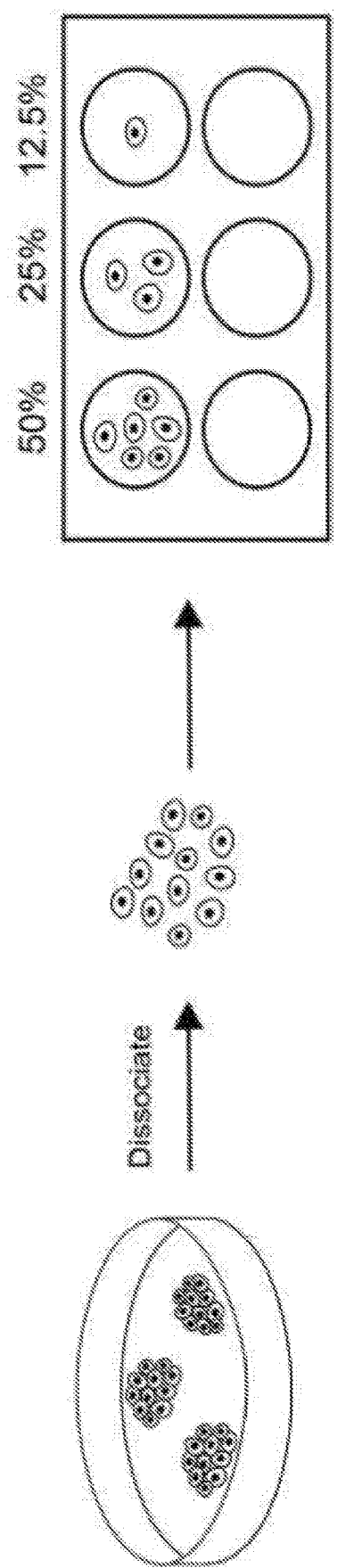
FIG. 17 depicts an image showing strategy to ensure the appropriate cell density for mesoderm induction.

Generation of iPSC Derived MSCs
Mesoderm Induction of iPSC
1. When iPSCs have reached 70-80% confluence, they will need to be passaged as single cells rather than colonies prior to mesoderm induction (day 0).
2. Prepare for passage by warming cell wash buffer and NutriStem hPSC XF medium to room temperature and add Y-27632 Rho kinase inhibitor to medium at a final concentration of 10 µM. Heat TrypLE cell dissociation reagent to 37° C.
3. Aspirate NutriStem hPSC XF medium from wells and wash once with PBS. Remove PBS and add 500 µl of pre-warmed TrypLE reagent to each well of a 6 well plate.
4. Incubate culture plate at 37° C. for 5 minutes. Check that most cells have been dislodged from the plate surface with a light microscope. If not, extend incubation time in 1-minute increments until noticeable cell detachment.
5. Add cell wash buffer to each well and gently resuspend cells from the plate by washing with a pipette. Check that most cells have been dislodged from the plate and that colonies are dissociated to small clusters of cells (≈5 cells per cluster) with a light microscope. If not, pipette up and down as needed.
6. Transfer cells to an appropriate tube and centrifuge at 300 g for 5 minutes. Check for the appearance of a cell pellet at the bottom of the tube.
7. Remove the supernatant and resuspend cells in an appropriate amount of NutriStem hPSC XF Medium containing 10 µM Y-27632 Rho kinase inhibitor. Plate cells on Matrigel coated culture plates (see Cell plating and culture above). Note: Because different lines of iPSCs proliferate at different rates, it is best to titrate one 6 well worth of iPSCs across 3 wells of a 6 well plate (ex. 1:2 (50%), 1:4 (25%), 1:8 (12.5%) for mesoderm induction (FIG. 17). This will ensure that at least 1 well will have the appropriate cell density after the mesoderm induction period.
8. Twenty-four hours after cell plating (day 1), aspirate NutriStem hPSC XF medium containing 10 Mm Y-27632 Rho kinase inhibitor and wash once with PBS. Remove PBS and add 2 ml of STEMdiff Mesoderm Induction Medium (MIM) to each well of a 6 well plate. Change 100% of the medium each day until day 5.

Generation of MSCs from Mesoderm
1. On day 5 of mesoderm induction (see Mesoderm induction of iPSC above), choose wells from the dilution series that are approximately 25-50% confluent, aspirate MIM and wash once with PBS. Remove PBS and replace with 2 ml of MesenCult-ACF Plus medium by gently pipetting down the side of the wells. Change media 100% every day until 100% confluent (usually between day 7 and 12). On day 7-12, cells must be passaged for further expansion and characterization. Cells passaged before growth for at least 2 days in MesenCult-ACF Plus medium will adhere poorly after plating.
2. Prior to passage, coat plates with MesenCult-ACF attachment substrate. Dilute MesenCult-ACF attachment substrate 1:300 in PBS without calcium or magnesium and add 1 ml/well for 6 well plates. Agitate plate to ensure that the coating is distributed over the entire surface of the wells. Allow plate to sit covered and undisturbed in a laminar flow cabinet for cell culture for at least 2 hours at room temperature.
3. To passage, warm cell wash buffer, ACF enzymatic dissociation solution, ACF enzymatic inhibition solution, and MesenCult-ACF Plus medium to room temperature.
4. Aspirate MesenCult-ACF Plus medium from cell culture plates and wash once with PBS. Remove PBS and add 500 µl of ACF enzymatic dissociation solution to each well of a 6 well plate. Note: Other enzymatic dissociation solutions such as trypsin, EDTA or TrypLE will not work as well for harvesting cells.
5. Place cell culture plate in a 37° C. incubator for 5 minutes undisturbed. Following 5 minutes, remove plate from incubator and tap side of plate firmly on hard surface several times such as bench countertop to sheer cells from plate surface (FIG. 18). Check that cells have dislodged from the well surface under a light microscope. If not, extend incubation time in 1-minute increments and tap again until noticeable detachment.
6. Add 500 µl of ACF enzymatic inhibition solution to each well of a 6 well plate.
7. Further suspend cells in 2 ml of cell wash buffer and gently remove cells from the plate by washing with a pipette. Check that most cells have been dislodged from the plate surface with a light microscope. If not, rewash with more cell wash buffer as needed.
8. Transfer cell suspension to an appropriate tube and centrifuge at 300 g for 5 minutes. Check for the appearance of a cell pellet at the bottom of the tube.
9. Remove the supernatant and resuspend pelleted cells in an appropriate amount of MesenCult-ACF Plus medium (4 ml per each well passaged). Cells will be passaged 1:2.
10. Prior to cell plating, aspirate MesenCult-ACF attachment substrate in PBS without calcium or magnesium from wells. Wash once with PBS and add cells suspended in MesenCult-ACF Plus medium (2 ml each well) to wells coated with MesenCult-ACF attachment substrate. Agitate plate to spread cells evenly on well surface and incubate plate at 37° C. in a 5% CO2 incubator undisturbed.
11. Change 100% of the culture medium daily. After reaching 90% confluence, continue to passage cells 1:2 for further expansion until they are >95% positive for CD105, CD73, CD90, CD146, and PDGFRβ cell surface markers as determined by flow cytometry. This usually occurs between 20 and 30 days. After full maturation of the MSC phenotype as determined by flow cytometry, cells can be passaged at lower densities (1:4-1:6 split). After their maturation, cells should be split when the high-density regions in the wells reach approximately 80% confluence. Growing MSCs to higher densities results in decreased differentiation potential over time.

Differentiation of MSCs into Mature Cells
Recipe for Beige Differentiation Mediums

TABLE 4

| Factor | stock concentration | working concentration | for 10 ml of medium |
|---|---|---|---|
| Beige adipogenic precursor induction medium: | | | |
| MesenCult-ACF | 1X | 1X | 10 ml |
| SB431542 | 10 mM | 5 µM | 5 µl |
| IL-4 | 10 µM | 10 nM | 10 µl |
| Beige adipocyte induction medium: | | | |
| EGM-2 | 1X | 1X | 10 ml |
| Insulin | (10 µg/ml = 1.7 mM) | 170 nM | 1 µl |
| T3 | 1 µM | 2 nM | 20 µl |
| Rosiglitazone | 5 mM | 1 µM | 2 µl |
| SB431542 | 10 mM | 5 µM | 5 µl |
| IBMX | 500 mM | 0.5 mM | 10 µl |
| Dexamethasone | 5 mM | 5 µM | 10 µl |
| Indomethacin | 125 mM | 125 µM | 10 µl |
| Beige adipocyte maintenance medium: | | | |
| EGM-2 | 1X | 1X | 10 ml |
| Insulin | 1.7 mM | 170 nM | 1 µl |
| T3 | 1 µM | 2 nM | 20 µl |
| Rosiglitazone | 5 mM | 1 µM | 2 µl |
| SB431542 | 10 mM | 5 µM | 5 µl |

Note: EGM-2 medium can be replaced with DMEM containing 10% FBS for both beige induction and beige maintenance medium. It is often better to use DMEM containing 10% FBS when comparing iPSC-derived beige cells directly to primary cells, since primary cells will not differentiate properly in EGM2 medium.

Generation of Beige Adipocytes
1. Prior to beige adipogenic precursor induction, MSCs grown in culture plates must be at approximately 90-100% confluence. Conduct beige adipogenic induction in a laminar flow cabinet.
2. Aspirate MesenCult-ACF Plus medium and replace with MesenCult-ACF Plus medium containing SB431542 (5 µM) and IL-4 (10 nM) in the following amounts based upon well size.
   96 well plates—100 µl/well
   24 well plates—500 µl/well
   6 well plates—2000 µl/well
Allow cells to stay in MesenCult-ACF Plus medium containing SB431542 and IL-4 for 48 hours.
3. Following 48 hours (cells should now be 100% confluent), aspirate MesenCult-ACF Plus medium containing SB431542 and IL-4 and wash once with PBS without calcium or magnesium. Remove PBS and replace with beige adipocyte induction medium in the following amounts based upon well size.
   96 well plate—150 µl/well
   24 well plates—1000 µl/well
   6 well plates—3000 µl/well
4. After 72 hours of induction treatment, aspirate beige adipocyte induction medium from wells and replace with beige adipocyte maintenance medium in the following amounts based upon well size.
   96 well plate—150 µl/well
   24 well plates—1000 µl/well
   6 well plates—3000 µl/well
5. Change 100% of beige adipocyte maintenance medium every 72 hours for 9 days.

DISCUSSION

A Renewable Source of Human Beige Adipocytes for Metabolic Disorders

An increased understanding of the development and regulation of beige adipose has the potential to enhance metabolic health and can be used to generate new treatments for metabolic syndrome. Primary beige adipogenic precursors isolated from humans require invasive methods for their procurement and the cells have limited renewability, hampering their use in cellular-based therapies. Direct reprogramming of adult cells into iPSCs has raised the possibility of producing an unlimited number of patient matched beige adipocytes for their study and use in cellular therapies.

The methods described herein demonstrated that human beige adipocytes can be generated from PSCs using a defined, multi-stage culture system (PSC=>mesoderm=>MSC=>adipogenic precursor=>beige adipocyte). FOXF1+ splanchnic mesoderm was identified as a developmental source of beige adipocytes. Culture of FOXF1+ splanchnic mesoderm in MSC medium generates mural-like MSCs that can be expanded through multiple passages to produce adipocytes with molecular and metabolic profiles consistent with beige adipocytes, including expression of UCP1 and increased mitochondrial content and proton-leak linked respiration. Inhibition of SMAD2/3 signaling and treatment with IL-4 further enhanced the differentiation of FOXF1-derived MSCs into beige adipocytes.

Furthermore, it was shown that human beige adipocytes can be generated from iPSCs using a defined, multistage culture system (iPSC≥mesoderm≥MSC≥adipogenic precursor≥beige adipocyte). In addition, FOXF1+ mesodermal precursor cells were identified as a developmental source of beige adipocytes. Culture of FOXF1+ precursors in MSC medium generates mural-like MSCs that can be expanded through multiple passages to produce adipocytes with molecular and metabolic profiles that are consistent with beige adipocytes, including expression of UCP1 and proton leak-linked respiration.

In addition, the iPSC reprogramming process in conjunction with the method described herein can greatly increase the browning potential of primary adipogenic precursors that possess an inherently low adipogenic capacity, to form a more robust, renewable and metabolically active source of beige adipocytes with anti-diabetic potential. This method opens the door to discover specific molecular or epigenetic signatures that may result in dysfunctional beige adipogenesis due to aging or type 2 diabetes.

Mesodermal Origins of Brown/Beige Adipocytes Generated from PSCs

The developmental origins of adipocytes are not well defined, yet this information may shed light on the distribution of distinct adipose tissue depots, help determine insights into their metabolic differences, and be used to develop strategies to engineer different types of adipose tissue for cellular therapies (Sanchez-Gurmaches et al., 2016). Along these lines, methods that generate adipocytes from iPSCs without the exogenous transfer of adipogenic genes can be exploited to determine the developmental origins of specific adipose tissue depots that arise in humans. A few studies have focused on the development of beigeand brown adipocytes.

PSC-derived classical brown adipocytes have been generated using a two stage hematopoietic growth factor cocktail that includes BMP4 and BMP7[21]. PSCs appear to differentiate through paraxial mesoderm and subsequently myoblast lineages as determined by transcript analysis[21]. The generation of PSC-derived beige adipocytes has also been reported[22]. With this method hematopoietic cell medium supplemented BMP4 and Activin-A was used to generate mesoderm that was directly induced into adipocytes that produce a beige molecular signature, however, the mesodermal lineage was not characterized.

Mature adipocytes normally arise through commitment of MSCs to adipogenic precursors and their terminal differentiation[42]. While the two above mentioned methods produce mature brown or beige adipocytes from PSCs rapidly (12 and 20 days, respectively), natural development through a multipotent and expandable MSC precursor is absent and the renewability of these methods is provided only at the level of the PSCs. In another study, embryoid bodies from PSCs were formed on non-adherent plates in the presence of transient retinoic acid treatment with subsequent outgrowth on adherent plates to generate an expanding population of MSCs[32,33].

Interestingly, these MSCs differentiate into adipocytes with a molecular profile indicative of both brown and beige characteristics. While their mesodermal origin is unknown, it is suggested that these cells may derive from either PAX3+ neural crest or myogenic lineages[32]. Fate mapping studies in mice have demonstrated that classical brown adipocytes derive from Myf5+/Pax7+ precursors that arise from the dermomyotomel. Other lineage tracing studies in mice have demonstrated that a significant portion of visceral adipocytes derives from a Wt1+ precursor population that arise from the lateral plate mesoderm, which is distinct from the origins of subcutaneous adipocytes[43]. Thus far, a precursor population that can be used to lineage trace the origin of beige adipocytes during embryonic development has remained elusive. White adipocytes arise from precursors that reside in the mural cell compartment of the adipose vasculature, and it has been speculated that they originate from a Myf5-precursor originating from the lateral plate mesoderm[19, 40]. Because cells isolated from the subcutaneous WAT vasculature can also form mature beige adipocytes, the possibility exists that beige adipocytes may also originate from within the lateral plate mesoderm.

Indeed, the method described herein demonstrates that beige adipocytes can be generated from a homogenous population of FOXF1+ cells. During embryonic development Foxf1 is expressed initially throughout the lateral plate mesoderm and becomes restricted to and required for separation of the splanchnic mesoderm through repression of somatically expressed Irx3[44]. Generation of a Foxf1 reporter mouse line and lineage tracing may shed more light onto the developmental origins of beige adipocytes that arise within distinct subcutaneous WAT depots.

Differentiation of FD-MSCs Toward Beige Adipogenic Precursors

Studies in mice have shown that inhibition of TGF-β signaling can result in increased browning of WAT and improved metabolic function[36]. In addition, PSC-derived MSCs show vastly increased adipogenic potential in the presence of the TGF-β inhibitor SB413542[33].

This result was confirmed and demonstrated that MSCs generated with the method described herein expressed TGF-β ligands, receptors and constitutively active TGF-β signaling via phosphorylated SMAD2. In addition to increasing beige adipogenesis, SB413542 alone directed differentiation of FD-MSCs toward an adipogenic precursor phenotype, including increased expression of PDGFRα, MSCA1, PPARG and EBF2, a transcription factor specific to brown and beige adipogenic precursors[45]. When induced with an adipogenic cocktail of factors, these precursors displayed an enhanced ability to form UCP1 expressing beige adipocytes.

Cold exposure in mice leads to activation of type 2 immune cells, including eosinophils, which secrete IL-4 and IL-13 to alternatively activate macrophages toward a polarized M2 fate[46]. This anti-inflammatory subset of macrophages in turn induces thermogenesis in adipose tissue through secretion of catecholamines (reviewed in[47]). In addition to macrophages, IL-4 can act directly on PDGFRα+ adipogenic precursors isolated from subcutaneous WAT and commit these precursors to a beige rather than WAT molecular phenotype[39]. Treatment of PDGFRα+ precursors with IL-4 in this study also enhanced the capacity for beige adipogenesis, as assessed by the expression of UCP1. A more recent study calls into question whether M2 macrophages secrete significant amounts of catecholamines and suggest that IL-4 plays no role in adaptive thermogenesis of adipose tissue[48]. Whether IL-4 promotes beige adipogenesis at the level of the adipogenic precursor or the macrophage in mice remains elusive. It could depend on the environmental history of the animal or the length of cold induction, which may influence whether beige adipogenesis results from browning of preexisting mature adipocytes or from de novo differentiation of adipogenic precursors[18]. In mice, long-term cold exposure appears to favor de novo beige formation from PDGFRI3+ mural cell adipogenic precursors[49]. Along these lines, the study indicates that IL-4 can significantly enhance differentiation of mural-like FD-MSCs (PDGFRI3+) into committed beige adipogenic precursors with increased expression of PDGFRα+, MSCA1, PPARG and EBF2. Differentiation of these precursors display enhanced beige adipogenesis, including earlier induction and increased expression of UCP1. Thus, IL-4 may exert its effects by promoting commitment of the PDGFRI3+ mural cell lineage to beige adipocytes during chronic cold exposure.

Advantages of FD-MSCs for Generation of Beige Adipocytes

The method described herein has several advantages over other existing methods to produce large numbers of thermogenically active adipocytes. While the method takes longer than others to generate beige adipocytes from PSCs, once obtained, FD-MSCs are highly expandable (>15 passages), and require only 12 days of adipogenic differentiation to form fully mature beige adipocytes. Thus the method herein is renewable at both the PSC and MSC stages.

In addition, FD-MSCs are multipotent and can be used to study formation of other terminally differentiated cell types that arise from the splanchnic mesoderm compartment, including osteocytes and chondrocytes. PSCs derived from patients with diseases that affect bone, cartilage and adipocytes can be studied using this method.

In this study, it was shown that reprogramming can increase the beige adipogenic potential of dysfunctional adipogenic precursors isolated from an elderly type 2 diabetic patient. While other primary cell types from patients with metabolic abnormalities may provide a better source of iPSCs for the generation of beige adipocytes, reprogramming primary adipogenic precursors may be used to find important epigenetic changes that result in metabolic defects by comparing epigenetic signatures before and after reprogramming.

In summary, a new method to generate metabolically active beige adipocytes from PSCs was identified that serves as a model to study beige cell development and regulation. The scalability of this method provides a platform to generate copious numbers of beige adipocytes for high throughput drug screening, transplantation directed therapies and discovery and isolation of secreted factors that may aid in reducing pathophysiologies associated with metabolic syndrome.

REFERENCES

1. Harms M and Seale P. Brown and beige fat: development, function and therapeutic potential. *Nature medicine.* 2013; 19:1252-63.
2. Malik V S. et al. Global obesity: trends, risk factors and policy implications. *Nat Rev Endocrinol.* 2013; 9:13-27.
3. Ochner C N, et al. Treating obesity seriously: when recommendations for lifestyle change confront biological adaptations. *Lancet Diabetes Endocrinol.* 2015; 3:232-4.
4. Seale P and Lazar M A. Brown fat in humans: turning up the heat on obesity. *Diabetes.* 2009; 58:1482-4.
5. Lumeng C N and Saltiel A R. Inflammatory links between obesity and metabolic disease. *J Glin Invest.* 2011; 121: 2111-7.
6. Cannon B and Nedergaard J. Brown adipose tissue: function and physiological significance. *Physiological reviews.* 2004; 84:277-359.
7. Ravussin Y, et al. L. Effect of intermittent cold exposure on brown fat activation, obesity, and energy homeostasis in mice. *PLoS One.* 2014; 9:e85876.
8. Xiao C, et al. Anti-obesity and metabolic efficacy of the beta3-adrenergic agonist, CL316243, in mice at thermoneutrality compared to 22 degrees C. *Obesity (Silver Spring).* 2015; 23:1450-9.
9. Cao W, et al. p38 mitogen-activated protein kinase is the central regulator of cyclic AMP-dependent transcription of the brown fat uncoupling protein 1 gene. *Mol Cell Biol.* 2004; 24:3057-67.
10. Cypess A M, et al. Identification and importance of brown adipose tissue in adult humans. *N Engl J Med.* 2009; 360:1509-17.
11. Wang G X, et al. The brown fat secretome: metabolic functions beyond thermogenesis. *Trends Endocrinol Metab.* 2015; 26:231-7.
12. Cypess A M, et al. Activation of human brown adipose tissue by a beta3-adrenergic receptor agonist. *Cell metabolism.* 2015; 21:33-8.
13. Liu X, et al. Brown adipose tissue transplantation improves whole-body energy metabolism. *Cell Res.* 2013; 23:851-4.
14. Graja A and Schulz T J. Mechanisms of aging-related impairment of brown adipocyte development and function. *Gerontology.* 2015; 61:211-7.
15. Wang Q, et al. Brown adipose tissue activation is inversely related to central obesity and metabolic parameters in adult human. *PLoS One.* 2015; 10:e0123795.
16. Patel P and Abate N. Role of subcutaneous adipose tissue in the pathogenesis of insulin resistance. *J Obes.* 2013; 2013:489187.
17. Chung K J, et al. A self-sustained loop of inflammation-driven inhibition of beige adipogenesis in obesity. *Nat Immunol.* 2017; 18:654-664.
18. Wang W and Seale P. Control of brown and beige fat development. *Nat Rev Mol Cell Biol.* 2016; 17:691-702.
19. Hassan M, et al. Adipose tissue: friend or foe? *Nat Rev Cardiol.* 2012; 9:689-702.
20. Lidell M E, et al. Two types of brown adipose tissue in humans. *Adipocyte.* 2014; 3:63-6.
21. Nishio M, et al. Production of functional classical brown adipocytes from human pluripotent stem cells using specific hemopoietin cocktail without gene transfer. *Cell metabolism.* 2012; 16:394-406.
22. Guenantin A C, et al. Functional Human Beige Adipocytes from Induced Pluripotent Stem Cells. *Diabetes.* 2017.
23. Luzzani C D and Miriuka S G. Pluripotent Stem Cells as a Robust Source of Mesenchymal Stem Cells. *Stem Cell Rev.* 2017; 13:68-78.
24. Tan J Y, et al. Efficient derivation of lateral plate and paraxial mesoderm subtypes from human embryonic stem cells through GSKi-mediated differentiation. *Stem Cells Dev.* 2013; 22:1893-906.
25. Dressler G R. Advances in early kidney specification, development and patterning. *Development.* 2009; 136: 3863-74.
26. Mahlapuu M, et al. Haploinsufficiency of the forkhead gene Foxf1, a target for sonic hedgehog signaling, causes lung and foregut malformations. *Development.* 2001; 128: 2397-406.
27. Wasteson P, et al. Developmental origin of smooth muscle cells in the descending aorta in mice. *Development.* 2008; 135:1823-32.
28. Tribioli C, Frasch M and Lufkin T. Bapx1: an evolutionary conserved homologue of the *Drosophila* bagpipe homeobox gene is expressed in splanchnic mesoderm and the embryonic skeleton. *Mech Dev.* 1997; 65:145-62.
29. Roberts C W, et al. Development expression of Hox11 and specification of splenic cell fate. *The American journal of pathology.* 1995; 146:1089101.
30. Hafner A L and Dani C. Human induced pluripotent stem cells: A new source for brown and white adipocytes. *World J Stem Cells.* 2014; 6:467-72.
31. Crisan M, et al. A perivascular origin for mesenchymal stem cells in multiple human organs. *Cell Stem Cell.* 2008; 3:301-13.
32. Mohsen-Kanson T, et al. Differentiation of human induced pluripotent stem cells into brown and white adipocytes: role of Pax3. *Stem cells.* 2014; 32:1459-67.
33. Hafner A L, et al. Brown-like adipose progenitors derived from human induced pluripotent stem cells: Identification of critical pathways governing their adipogenic capacity. *Sci Rep.* 2016; 6:32490.
34. Lee Y H, et al. In vivo identification of bipotential adipocyte progenitors recruited by beta3-adrenoceptor activation and high-fat feeding. *Cell metabolism.* 2012; 15:480-91.
35. Esteve D, et al. Human white and brite adipogenesis is supported by MSCA1 and is impaired by immune cells. *Stem cells.* 2015; 33:1277-91.
36. Yadav H and Rane S G. TGF-beta/Smad3 Signaling Regulates Brown Adipocyte Induction in White Adipose Tissue. *Frontiers in endocrinology.* 2012; 3:35.
37. Berry D C, Stenesen D, Zeve D and Graff J M. The developmental origins of adipose tissue. Development. 2013; 140:3939-49.

38. Timmons J A, et al. Myogenic gene expression signature establishes that brown and white adipocytes originate from distinct cell lineages. *Proceedings of the National Academy of Sciences of the United States of America.* 2007; 104:4401-6.
40. Lee M W, et al. Activated type 2 *innate lymphoid cells* regulate beige fat biogenesis. *Cell.* 2015; 160:74-87.
41. Tang W, et al. White fat progenitor cells reside in the adipose vasculature. *Science.* 2008; 322:583-6.
42. Poleganov M A, et al. Efficient Reprogramming of Human Fibroblasts and Blood-Derived Endothelial Progenitor Cells Using Nonmodified RNA for Reprogramming and Immune Evasion. *Hum Gene Ther.* 2015; 26:751-66.
43. Cristancho A G and Lazar M A. Forming functional fat: a growing understanding of adipocyte differentiation. *Nat Rev Mol Cell Biol.* 2011; 12:722-34.
44. Chau Y Y, et al. Visceral and subcutaneous fat have different origins and evidence supports a mesothelial source. *Nat Cell Biol.* 2014; 16:367-75.
45. Mahlapuu M, et al. The forkhead transcription factor Foxf1 is required for differentiation of extra-embryonic and lateral plate mesoderm. *Development.* 2001; 128:155-66.
46. Wang W, et al. Ebf2 is a selective marker of brown and beige adipogenic precursor cells. *Proceedings of the National Academy of Sciences of the United States of America.* 2014; 111:14466-71.
47. Qiu Y, et al. Eosinophils and type 2 cytokine signaling in macrophages orchestrate development of functional beige fat. *Cell.* 2014; 157:1292-308.
48. van den Berg S M, et al. Immune Modulation of Brown(ing) Adipose Tissue in Obesity. *Endocr Rev.* 2017; 38:46-68.
49. Fischer K, et al. Alternatively activated macrophages do not synthesize catecholamines or contribute to adipose tissue adaptive thermogenesis. *Nature medicine.* 2017; 23:623-630.
50. Vishvanath L, et al. Pdgfrbeta+ Mural Preadipocytes Contribute to Adipocyte Hyperplasia Induced by High-Fat-Diet Feeding and Prolonged Cold Exposure in Adult Mice. *Cell metabolism.* 2016; 23:350-9.

What is claimed is:

1. A method of treating obesity in a subject in need thereof, the method comprising administering to the subject an effective amount of a population of beige adipocytes, or a factor obtained from the population of beige adipocytes, wherein the population of beige adipocytes are produced by contacting a mesenchymal stem cell (MSC) population with an effective amount of
   (i) interleukin 4 (IL-4); and
   (ii) a transforming growth factor beta (TGF-β) inhibitor.

2. The method of claim 1, wherein the MSC population is contacted with the IL-4 and the TGF-β inhibitor concurrently.

3. The method of claim 1, comprising culturing the MSC population in a cell culture medium that comprises the IL-4 and the TGF-β inhibitor.

4. The method of claim 1, wherein the TGF-β inhibitor is a small molecule, an antibody or a fragment thereof, an oligonucleotide, an aptamer, or a peptide.

5. The method of claim 1, wherein the TGF-β inhibitor is lerdelimumab, metelimumab, fresolimumab, LY2382770, trabedersen, lucanix, disitertide, galunisertib, TEW-7197, PF-03446962, LY3022859, or SB431542.

6. The method of claim 1, further comprising contacting the MSC population with an adipogenic differentiation compound.

7. The method of claim 6, wherein the MSC population is contacted with the TGF β inhibitor and the IL-4 to produce a preadipocyte population, and the preadipocyte population is contacted with the adipogenic differentiation compound.

8. The method of claim 6, wherein the adipogenic differentiation compound comprises a PPARγ activator.

9. The method of claim 6, wherein the adipogenic differentiation compound comprises 3,3',5-Triiodo-L-thyronine (T3), insulin, rosiglitazone, 3-isobutyl-1-methylxanthine (IBMX), or dexamethasone.

10. The method of claim 6, wherein the adipogenic differentiation compound comprises a compound that induces or increases adipogenesis.

11. The method of claim 1, wherein cells of the beige adipocyte population express uncoupling protein 1 (UCP1).

12. The method of claim 1, wherein cells of the beige adipocyte population secrete an anti-diabetic factor.

13. The method of claim 12, wherein the anti-diabetic factor is fibroblast growth factor 21 (FGF21), neuregulin 4 (NRG4), interleukin 6 (IL6), or Adiponectin, C1Q and Collagen Domain Containing (ADIPOQ) protein.

14. A method of treating obesity in a subject in need thereof, the method comprising administering to the subject an effective amount of IL-4 and a TGF-B inhibitor.

15. The method of claim 14, wherein the IL-4 and the TGF-β inhibitor are injected into adipose tissue of the subject.

16. A method of increasing the level of a beige adipocyte population in a subject in need thereof, the method comprising administering to the subject an effective amount of IL-4 and a TGF-β inhibitor.

17. The method of claim 16, wherein the IL-4 and the TGF-β inhibitor are injected into adipose tissue of the subject.

* * * * *